United States Patent
Oyelere et al.

(10) Patent No.: US 12,324,803 B2
(45) Date of Patent: *Jun. 10, 2025

(54) 3-(HYDROXY)-PYRIDIN-4(1H)-ONE COMPOUNDS AND METHODS OF MAKING AND USING THE SAME

(71) Applicant: Georgia Tech Research Corporation, Atlanta, GA (US)

(72) Inventors: Adegboyega K. Oyelere, Atlanta, GA (US); Verjine Khodaverdian, Atlanta, GA (US); Subhasish Tapadar, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/297,974

(22) Filed: Apr. 10, 2023

(65) Prior Publication Data

US 2023/0255950 A1    Aug. 17, 2023

Related U.S. Application Data

(63) Continuation of application No. 16/982,559, filed as application No. PCT/US2019/023127 on Mar. 20, 2019, now Pat. No. 11,654,137.

(60) Provisional application No. 62/645,302, filed on Mar. 20, 2018.

(51) Int. Cl.
*A61K 31/4439* (2006.01)
*A61K 45/06* (2006.01)
*A61P 35/00* (2006.01)
*C07D 401/06* (2006.01)

(52) U.S. Cl.
CPC .......... *A61K 31/4439* (2013.01); *A61K 45/06* (2013.01); *A61P 35/00* (2018.01); *C07D 401/06* (2013.01)

(58) Field of Classification Search
None
See application file for complete search history.

(56) References Cited

U.S. PATENT DOCUMENTS 11,654,137 B2 *  5/2023  Oyelere ............. A61K 31/4439
                                                         514/340

FOREIGN PATENT DOCUMENTS

AT         503733  A1    12/2007

OTHER PUBLICATIONS

Report from EP Application No. 19771611,1 dated Jul. 18, 2022.
Santos, et al., Journal of Biological Inorganic Chemistry (2005), 10(5) pp. 564-580.
Silva, et al., "Microwave-Assisted Synthesis of 3-hydroxy-4-pyridinone/naphthalene Conjugates Structural Characterization and Selection of a Fluorescent Ion Sensor," Tetrahedron (2010), 66(44), pp. 8544-8550.
Gehrke, et al., Bioorganic & Medicinal Chemistry (2013), 21(3), pp. 805-813.
Hiremathad, et al., "Hydroxypyridinone-benzofuran Hybrids with Potential Protective Roles for Alzheimer's Disease Therapy," Journal of Inorganic Biochemistry (2018) 179, pp. 82-96.
Nunes, et al., "Multifunctional Iron-chelators with Protective Roles Against Neurodegenerative Diseases," Dalton Transactions (2013), 42(17), pp. 6058-6073.
Supplementary Search Report and Written Opinion from Application No. EP19771611 dated Nov. 22, 2021.
International Preliminary Report on Patentability for Application No. PCT/US2019/023127 dated Sep. 22, 2020.
International Search Report and Written Opinion from Application No. PCT/US2019/023127 dated Jun. 27, 2019.
Mendoza-Ferri, et al., "Influence of the Arene Ligand, the Number, and the Type of Metal Centers, and the Leaving Group on the in Vitro Antitumor activity of Polynuclear Organometalic Compounds," Organometallics, 2009, 28(21), pp. 6260-6265.
Mendoza-Ferri, et al., "Influence of the Spacer Length on the in Vitro Anticancer Activity of Dinuclear Ruthenium-Arene Compounds," Organometallics, 2008, 27(11), pp. 2405-2407.
Mendoza-Ferri, et al., "Transferring the Concept of Multinuclearity to Ruthenium Complexes for Improvement of Anticancer Activity," Journal of Medicinal Chemistry, 2009, 52(4), pp. 916-925.
Nelson, et al., "Physical and Structural Studies of N-Substituted-3-hydroxy-2-methyl-4-(1H)-pyridinones," Canadian Journal of Chemistry, 1998, 66(1), pp. 123-131.
Sheppard, et al., "Comparative Iron Binding studies of bis- and tris(3-hydorxy-2-methylpyrid-4-ones) and Desferrioxamine," Inorganica. Chimica. Acta., 1991, 188(2), pp. 177-183.

* cited by examiner

*Primary Examiner* — Brian J Davis
(74) *Attorney, Agent, or Firm* — Troutman Pepper Locke LLP; Ryan A. Schneider; Tanya Leavy

(57)    ABSTRACT

Compositions and methods for inhibiting histone lysine demethylases are provided. Several new DFP-based KDM inhibitors which alter the velocity of HP1-mediated heterochromatin gene repression are provided.

21 Claims, 6 Drawing Sheets

--Prior Art--

3-hydoxy-1,2-
dimethylpyridine-4(1*H*)-one
(Deferiprone)

3-hydroxypyridin-
2(1*H*)-one 3-hydroxypyridine
4(1*H*)-one 3-hydroxypyridine
2(1*H*)-one 3-hydroxypyridine
4(1*H*)-thione 1-hydroxypyridine
2(1*H*)-one

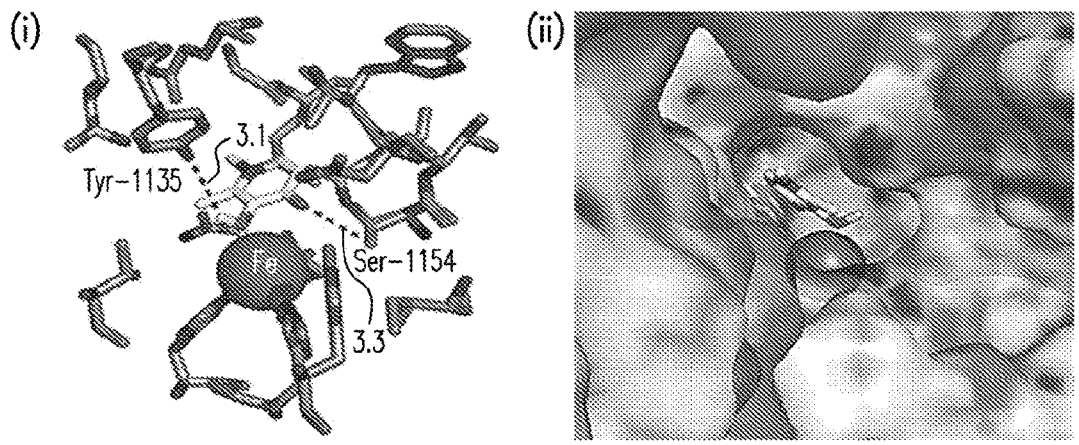
FIG.2A
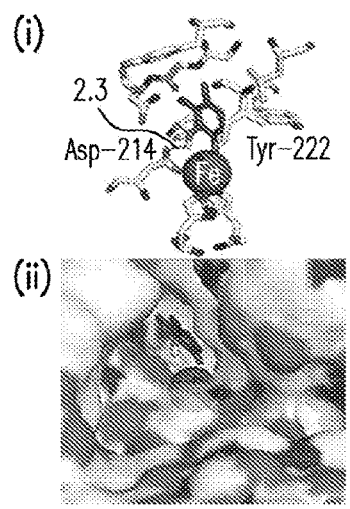 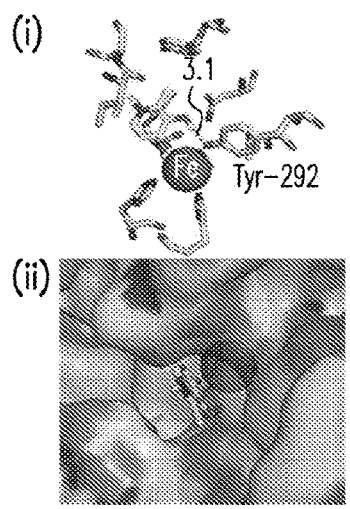 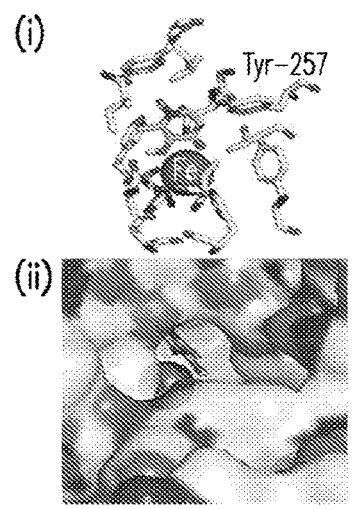
FIG.2B  FIG.2C  FIG.2D

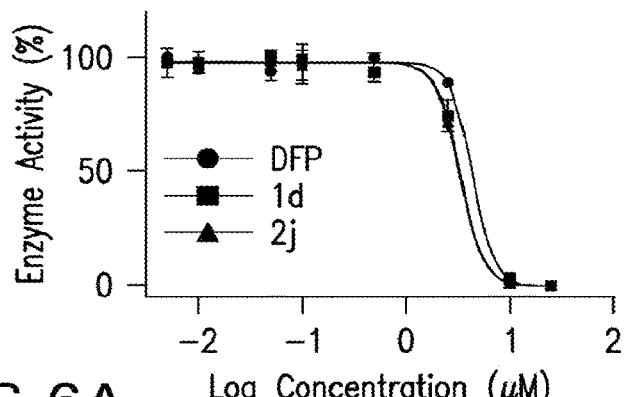
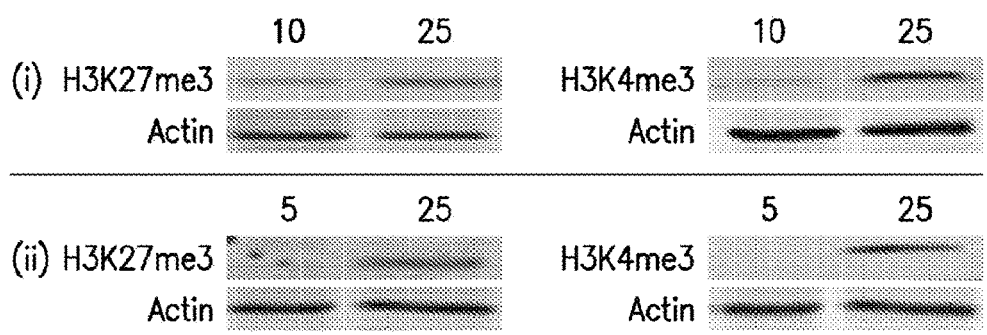
FIG.6A
FIG.6B

3-(HYDROXY)-PYRIDIN-4(1H)-ONE COMPOUNDS AND METHODS OF MAKING AND USING THE SAME

CROSS REFERENCE TO RELATED APPLICATIONS

This application is a continuation application of U.S. patent application Ser. No. 16/982,559, filed on Sep. 19, 2020, which is a national stage application, filed under 35 U.S.C. § 371, of International Patent Application No. PCT/US2019/023127 filed on Mar. 20, 2019, which claims benefit of and priority to U.S. Provisional Patent Application No. 62/645,302 filed on Mar. 20, 2018, which are incorporated herein by reference in their entirety.

STATEMENT REGARDING FEDERALLY SPONSORED RESEARCH

This invention was made with Government support under grant No. R21CA185690. The government has certain rights in the invention.

TECHNICAL FIELD OF THE INVENTION

This application is generally directed to compounds that inhibit histone lysine demethylase and methods of use thereof.

BACKGROUND OF THE INVENTION

Dysfunction in the activities of KDMs have been implicated in the development and sustenance of several tumor types [(a) Hoffmann, I.; Roatsch, M.; Schmitt, M. L.; Carlino, L.; Pippel, M.; Sippl, W.; Jung, M. The role of histone demethylases in cancer therapy. Mol. Oncology 2012, 6, 683-703. (b) Kaniskan, H. Ü; Martini, M. L.; Jin, J. Inhibitors of Protein Methyltransferases and Demethylases. Chem Rev 2018, 118, 989z1068.], suggesting the broad and significant roles of KDMs in the etiology of human cancers. Specifically, literature reports have identified specific members or isoforms of the amino oxidase and Jumonji family of histone lysine demethylases (KDMs) as essential in supporting proliferation of several cancer cells, including but not limiting to hormone positive breast and prostate cancer cells, lung cancer cells, liver cancer cells [(a) Shi, L.; Sun, L.; Li, Q.; Liang, J.; Yu, W.; Yi, X.; Yang, X.; et al. Histone demethylase JMJD2B coordinates H3K4/H3K9 methylation and promotes hormonally responsive breast carcinogenesis. Proc Natl Acad Sci USA 2011, 108, 7541-7546. (b) Duan, L.; Rai, G.; Roggero, C.; Zhang, Q-J.; et al. KDM4/JMJD2 histone demethylase inhibitors block prostate tumor growth by suppressing the expression of AR and BMYB-regulated genes. Chem Biol. 2015, 22, 1185-1196. (c) Dalvi, M. P.; Wang, L.; Zhong, R.; Kollipara, R. K.; Park, H.; et al Taxane-Platin-Resistant Lung Cancers Co-develop Hypersensitivity to JumonjiC Demethylase Inhibitors. Cell Reports 2017, 19, 1669-1684. (d) Wang, D.; Han, S.; Peng, R.; Jiao, C.; et al. Depletion of histone demethylase KDM5B inhibits cell proliferation of hepatocellular carcinoma by regulation of cell cycle checkpoint proteins p15 and p27 J Exp Clin Cancer Res. 2016, 35, 37.]. Among these epigenetic modifiers, KDM1A, KDM3A, KDM5A, KDM5B and could be ideal targets for unrevealing new insights KDM1 is a Flavin dependent monoamine oxidase which demethylate histone H3 lysines 4 and 9 (H3K4 and H3K9) while members of the KDM5 and KDM6 families are 2-oxoglutarate- and $Fe^{2+}$-dependent oxygenases that act as specific H3K4 and H3K27me3 demethylases respectively [Dante Rotili, Antonello Mai. Targeting Histone Demethylases: A New Avenue for the Fight against Cancer. Genes Cancer 2011, 2, 663-679.] The activities of these KDMs regulate cell proliferation, differentiation, and modulates epigenetic changes via interactions with ER co-regulator protein PELP1 [(a) Perillo, B.; Ombra, M. N.; Bertoni, A.; Cuozzo, C.; Sacchetti, S.; Sasso, A.; Chiariotti, L.; Malorni, A.; Abbondanza, C.; Avvedimento, E. V. DNA oxidation as triggered by H3K9me2 demethylation drives estrogen-induced gene expression. Science 2008, 319, 202-206. (b) Cortez, V.; Mann, M.; Tekmal, S.; Suzuki, T.; Miyata, N.; Rodriguez-Aguayo, C.; Lopez-Berestein, G.; Sood, A. K.; Vadlamudi, R. K. Targeting the PELP1-KDM1 axis as a potential therapeutic strategy for breast cancer. Breast Cancer Research 2012, 14, R108]. KDM5A and KDM5B are oncogenes that are overexpressed mostly in BCas and other tumors as well.

KDM5A positively regulates many metastasis-related genes which are required for BCa metastatic colonization in the lungs [Cao, J.; Liu, Z.; Cheung, W. K. C.; Zhao, M.; Chen, S. Y.; Chan, S. W.; Booth, C. J.; Nguyen, D. X.; Yan, Q. Histone Demethylase RBP2 Is Critical for Breast Cancer Progression and Metastasis. Cell Reports 2014, 6, 868-877.]. KDM5B is BCa, functioning as luminal lineage-driving oncogene and poor prognosis predictor [Yamamoto, S.; Wu, Z.; Russnes, H. G.; Takagi, S.; Peluffo, G.; Vaske, C.; Zhao, X.; et al. JARID1B is a luminal lineage-driving oncogene in breast cancer. Cancer Cell. 2014, 25, 762-777.]. Similarly, KDM6A positively regulates gene expression programs associated with BCa proliferation and invasion [Kim, J. H.; Sharma, A.; Dhar, S. S.; Lee, S. H.; Gu, B.; Chan, C. H.; Lin, H. K.; Lee, M. G. UTX and MLL4 coordinately regulate transcriptional programs for cell proliferation and invasiveness in breast cancer cells. Cancer Res. 2014, 74, 1705-1717.]. Multi-drug-resistant lung cancer cells overexpress several KDMs, have altered histone methylation, and are hypersensitive to KDM inhibitors in vitro and in vivo [Dalvi, M. P.; Wang, L.; Zhong, R.; Kollipara, R. K.; Park, H.; et al Taxane-Platin-Resistant Lung Cancers Co-develop Hypersensitivity to JumonjiC Demethylase Inhibitors. Cell Reports 2017, 19, 1669-1684.]. KDMs, KDM1A, KDM2A, KDM3A-B, KDM4A, KDM4D and KDM5B have been shown to be vital for lung cancer cell viability. Expression profiling of human lung cancer specimens revealed a significant correlation of KDM1A overexpression with disease progression and metastasis [Lim, S-Y.; Macheleidt, I.; Dalvi, P.; Schafer, S. C.; Kerick, M.; et al LSD1 modulates the non-canonical integrin signaling pathway in non-small cell lung carcinoma cells. Sci. Reports 2017, 7: 10292. DOI: 10.1038/s41598-017-09554-x]. KDM1A promotes lung cancer cell invasiveness by regulating the non-canonical integrin pathway and the highest expression levels are detected in SCLC which are uniquely sensitive to KDM1A inhibitors [(a) Lim, S-Y.; Macheleidt, I.; Dalvi, P.; Schäfer, S. C.; Kerick, M.; et al LSD1 modulates the non-canonical integrin 3 signaling pathway in non-small cell lung carcinoma cells. Sci. Reports 2017, 7: 10292. DOI:10.1038/s41598-017-09554-x. (b) Mohammad, H. P.; Smitheman, K. N.; Kamat, C. D.; Soong, D.; Federowicz, K. E.; Van Aller, G. S.; Schneck, J. L.; Carson, J. D.; Liu, Y.; Butticello, M.; et al A DNA Hypomethylation Signature Predicts Antitumor Activity of LSD1 Inhibitors in SCLC. Cancer Cell 2015, 28, 57-69.]. KDM2A promotes lung cancer by enhancing ERK1/2 signaling [Wagner, K. W. KDM2A promotes lung tumorigenesis by epigenetically enhancing ERK1/2 signaling. *J Clin Invest.* 2013, 123, 5231-5246.] NSCLC patient tumor cells resistant to neoadjuvant chemotherapy expressed higher KDM3A-B and 4A mRNAs than chemo-naive tumors with KDM3B protein levels showing the largest hazard risk for poor recurrence-free outcome in neoadjuvant-treated NSCLC patients [Dalvi, M. P.; Wang, L.; Zhong, R.; Kollipara, R. K.; Park, H.; et al Taxane-Platin-Resistant Lung Cancers Co-develop Hypersensitivity to JumonjiC Demethylase Inhibitors. *Cell Reports* 2017, 19, 1669-1684.]. KDM3A has been implicated in the facilitation of immune system evasion of lung adenocarcinoma [Li, Y.; Yang, W.; Wu, B.; Liu, Y.; Li, D.; Guo, Y.; Fu, H.; Li, Y. KDM3A promotes inhibitory cytokines secretion by participating in TLR4 regulation of Foxp3 transcription in lung adenocarcinoma cells. *Oncology Lett.* 2017, 13, 3529-3537.]. Nuclear expression of KDM4A and KDM4D plays a significant role in the metastasis of lung carcinomas including lymph node metastases [Soini, Y.; Kosma, V-M.; Pirinen, R. KDM4A, KDM4B and KDM4C in non-small cell lung cancer. Int J Clin Exp Pathol. 2015, 8, 12922-12928].

KDM5B is overexpressed in lung cancers and other tumors, and it stimulates lung cancer cell proliferation and invasion by affecting p53 while its depletion results in the suppression of cell growth through co-regulation of the E2F/RB1 pathway [(a) Scibetta, A. G.; Santangelo, S.; Coleman, J.; Hall, D.; Chaplin, T.; Copier, J.; Catchpole, S.; Burchell, J.; Taylor-Papadimitriou, J. Functional analysis of the transcription repressor PLU-1/JARID1B. *Mol Cell Biol.* 2007, 27, 7220-7235. (b) Shen, X.; Zhuang, Z.; Zhang, Y.; Chen, Z.; Shen, L.; Pu, W.; Chen, L.; Xu, Z. JARID1B modulates lung cancer cell proliferation and invasion by regulating p53 expression. *Tumor Biol.* 2015, 36, 7133-7142.]. Additionally, KDMs have been implicated in the regulation of inflammation [(a) Kruidenier, L.; Chung, C.; Cheng, Z.; Liddle, J.; Che, K.; Joberty, G.; et al. A selective jumonji H3K27 demethylase inhibitor modulates the proinflammatory macrophage response. *Nature* 2012, 488, 404-408. (b) Doñas, C.; Carrasco, M.; Fritz, M.; Prado, C.; Tejón, G.; Osorio-Barrios, F.; Manriquez, V.; Reyes, P.; Pacheco, R.; Bono, M. R.; Loyola, A.; Rosemblatt, M. The histone demethylase inhibitor GSK-J4 limits inflammation through the induction of a tolerogenic phenotype on DCs. *J Autoimmun.* 2016, 75, 105-117. (c) Cribbs, A.; Hookway, E. S.; Wells, G.; Lindow, M.; Obad, S.; et al Inhibition of histone H3K27 demethylase selectively modulates inflammatory phenotypes of natural killer cells. *J. Biol. Chem.* 2018, doi: 10.1074/jbc.RA117.000698].

It is an object of the invention to provide 3-(hydroxy)-pyridin-4(1H)-one-based pan-selective KDM inhibitors with anti-tumor activities and methods of making and using thereof.

SUMMARY OF THE INVENTION

Compositions and methods for inhibiting histone lysine demethylases are provided. Several new DFP-based KDM inhibitors which alter the velocity of HP1-mediated heterochromatin gene repression are provided.

One embodiment provides a compound according to Formula I:

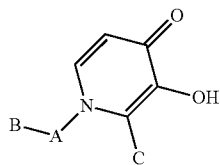

Formula I wherein A is —$(CH_2)_n$— n is 2-8,

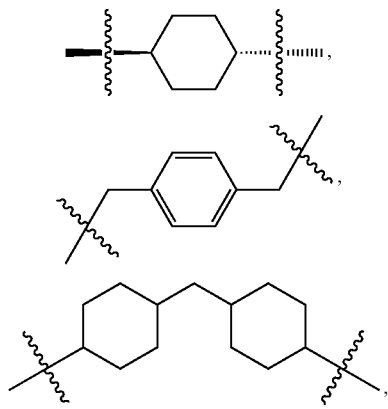

B is AR-AR', wherein AR' is a linking group connecting AR and A selected from the group consisting of

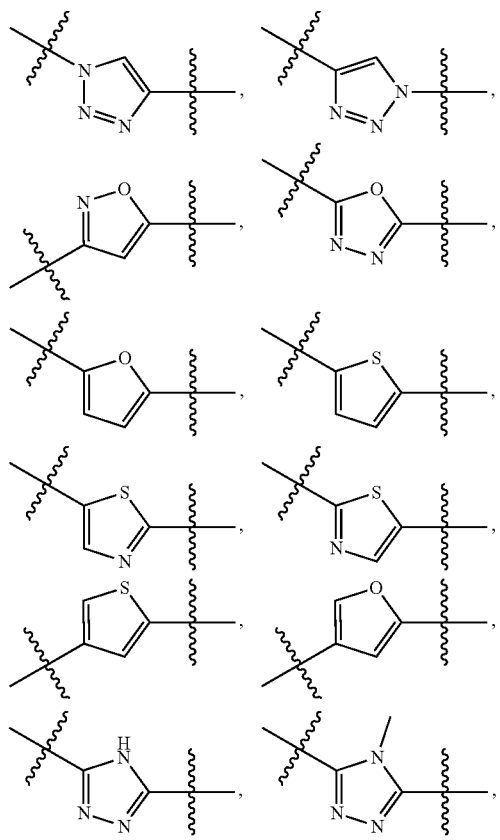

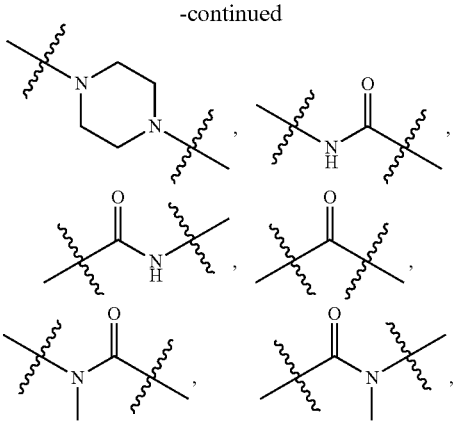

wherein AR is aryl, a 6-membered aromatic, heterocyclic, fused aromatic, fused heterocyclic, biaromatic, or bihetereocyclic ring system, optionally substituted by halogens, alkyl-, alkenyl-, and alkynyl groups,
wherein, when A is:

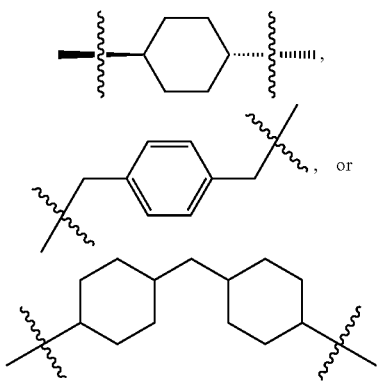

B is

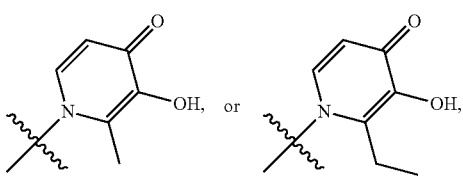

and
wherein C is alkyl, aryl; preferably methyl, ethyl, phenyl and pyridyl groups and the phenyl and pyridiyl groups are optionally substituted at the ortho, meta and para positions.

Another embodiment provides compounds 1a-1f, 2l-2w, 3a-3g, and 36a-36g including hydrates, solvates, isolated isomers thereof, and pharmaceutically acceptable salts thereof. Methods of their use are also provided.

BRIEF DESCRIPTION OF THE DRAWINGS

FIGS. 2A-2D(i) show docked poses of DFP on representative KDMs. (A) DFP binds to the active site of KDM6A (i) through chelation to the active site $Fe^{2+}$ and H-bonding interaction with the phenolic group of Tyr 1135 and OH group of Ser 1154, (ii) adopting docked pose having its N–1 moiety oriented toward the exit channel of the active site. (B) DFP interacts with KDM2A (i) through $Fe^{2+}$ chelation and H-bonding interactions to Tyr 222 and Asp 214, and (ii) with the N–1 moiety oriented away from the exit channel. (C) DFP interacts with KDM7A (i) through Fe2+ chelation and H-bonding to Tyr 292, and (ii) the N–1 moiety adopts a similar orientation as in KDMA6A. (D) DFP interacts with KDM7B docked position with (i) through Fe2+ chelation and (ii) the N–1 group is buried within the active site.

FIG. 5A is 2u. FIG. 5B is 3g. 2u and 3g adopt orientation at the active site of KDM6A that are similar to DFP with their N–1 moiety oriented to the exit channel of the active site. In addition to the interaction with the active site Fe2+, 2u could form additional H-bonding interactions with Asn 1156, Ser 1154, Gln 1003, and Ser 1025 (5C) while 3 g could form additional H-bonding interactions with Asn 1156, Ser 1154, and Trp1239 near active site Fe2+, and guanidine of Arg 1001 and Ser 1192 near the exit tunnel (5D).

FIG. 6A shows the structures and dose response curve for 1d and 2j. FIG. 6B shows autoradiographs indicating that 1 d and 2u cause dose dependent up-regulation of H3K4me and H3K27me in MDA-MB-231 cells.

DETAILED DESCRIPTION

I. Definitions

Figure 1:
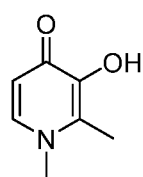
FIG. 1 shows the structures of representative examples of hydroxypyridinone bidentate metal ion chelators.
Figure 1:
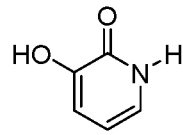
Figure 1:
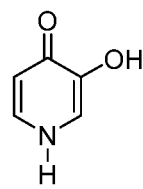
Figure 1:
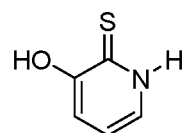
Figure 1:
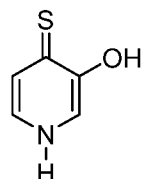
Figure 1:
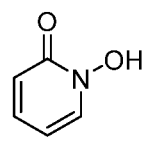

The term "carrier" refers to an organic or inorganic ingredient, natural or synthetic, with which the active ingredient is combined to facilitate the application.

The term "pharmaceutically acceptable" means a nontoxic material that does not interfere with the effectiveness of the biological activity of the active ingredients.

The term "pharmaceutically-acceptable carrier" means one or more compatible solid or liquid fillers, dilutants or encapsulating substances which are suitable for administration to a human or other vertebrate animal.

The term "effective amount" or "therapeutically effective amount" means a dosage sufficient to provide treatment a disorder, disease, or condition being treated, or to otherwise provide a desired pharmacologic and/or physiologic effect. The precise dosage will vary according to a variety of factors such as subject-dependent variables (e.g., age, immune system health, etc.), the disease, and the treatment being effected.

The terms "individual," "individual," "subject," and "patient" are used interchangeably herein, and refer to a mammal, including, but not limited to, humans, rodents, such as mice and rats, and other laboratory animals.

"Alkyl" is a saturated or unsaturated, straight or branched, hydrocarbon chain. In various embodiments, the alkyl group has 1-18 carbon atoms, i.e. is a $C_1$-$C_{18}$ group, or is a $C_1$-$C_{12}$ group, a $C_1$-$C_6$ group, or a $C_1$-$C_4$ group. A lower alkyl group has 1-6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less then 25, 24, 23, 22, 21, 20, 19, 18, 17, 16, 15, 14, 13, 12, 11, 10, 9, 8, or 7 carbons.

"Lower alkyl" means a group having about 1 to about 6 carbon atoms in the chain which chain may be straight or branched. Non-limiting examples of suitable alkyl groups include methyl, ethyl, n-propyl, isopropyl, n-butyl, t-butyl, and n-pentyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aryl" (sometimes abbreviated "Ar") is an aromatic carbocyclic hydrocarbon ring system. The ring system may be monocyclic or fused polycyclic (e.g., bicyclic, tricyclic, etc.). In one embodiment, the aryl group is monocyclic, and is preferably a $C_6$ ring system, i.e., a phenyl ring is a preferred aryl ring, where preferred bicyclic aryl rings are $C_8$-$C_{12}$, or $C_9$-$C_{10}$. A naphthyl ring, which has 10 carbon atoms, is a preferred polycyclic aryl ring. Unless otherwise indicated herein, the term "aryl" as used herein is meant to include aryl rings optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —B(OH)$_2$ or —B(OR)$_2$), carboxy (—C(O)—OH), alkoxycarbonyl (—C(O)—OR), aminocarbonyl (—C(O)—$NH_2$), aminosulfonyl (—S(O)$_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R group is an alkyl group having less than about 12 carbons, preferably where the R group is a lower alkyl group. Non-limiting examples of suitable aryl groups include: phenyl, naphthyl, indenyl, tetrahydronaphthyl, indanyl, anthracenyl, and fluorenyl.

"Arylalkyl" refers to an alkyl group as defined substituted by one or more aryl groups as defined below. Phenyl and naphthyl are preferred aryl groups in an arylalkyl group. A preferred alkyl group is methyl, so that a preferred arylalkyl group is benzyl or benzyl having one or more substituents on the phenyl ring. Unless otherwise indicated, the term "arylalkyl" as used herein is meant to include arylalkyl groups wherein the aryl ring therein is optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —B(OH)$_2$ or —B(OR)$_2$), carboxy (—C(O)—OH), alkoxycarbonyl (—C(O)—OR), aminocarbonyl (—C(O)—$NH_2$), aminosulfonyl (—S(O)$_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R is an alkyl group having less than about 12 carbons, preferably where the R group is a lower alkyl group.

"Arylalkyl" means an aryl-alkyl-group in which the aryl and alkyl are as previously described. Preferred arylalkyls comprise a lower alkyl group. Non-limiting examples of suitable aralkyl groups include benzyl, 2-phenethyl and napthalenylmethyl. The bond to the parent moiety is through the alkyl.

"Aryloxy" means an aryl-O-group in which the aryl group is as previously described. Non-limiting examples of suitable aryloxy groups include phenoxy and naphthoxy. The bond to the parent moiety is through the ether oxygen.

"Carboxyalkyl" means an HOOC-alkyl-group, wherein alkyl is as defined above, bound to the parent moiety through the alkyl group.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. A multicyclic cycloalkyl substituent may include fused, Spiro, or bridged ring structures. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalin, norbornyl, adamantly and the like. Cycloalkyl substituents may be substituted or unsubstituted. In one embodiment, the cycloalkyl is unsubstituted. In another embodiment, the cycloalkyl is substituted with, e.g., 1 substituent (i.e., the cycloalkyl group is mono-substituted), or 1-2 substituents, or 1-3 substituents, or 1-4 substituents, etc. In one embodiment, the substituents that may be present on the cycloalkyl aliphatic ring are selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —B(OH)$_2$ or —B(OR)$_2$), carboxy (—C(O)—OH), alkoxycarbonyl (—C(O)—OR), aminocarbonyl (—C(O)—$NH_2$), aminosulfonyl (—S(O)$_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) In one aspect the R group in the above substituents is an alkyl group having less than about 12 carbons, while in another aspect the R group is a lower alkyl group.

"Cycloalkylalkyl" means a cycloalkyl group bound to the parent moiety through an alkyl group. Non-limiting examples include: cyclopropylmethyl and cyclohexylmethyl.

"Cycloalkylaryl" means a cycloalkyl group bound to the parent moiety through an aryl group. Non-limiting examples include: cyclopropylphenyl and cyclohexylphenyl.

"Fluoroalkoxy" means an alkoxy group as defined above wherein one or more hydrogen atoms on the alkoxy is or are replaced by a fluoro group.

"Fluoroalkyl" means an alkyl group as defined above wherein one or more hydrogen atoms on the alkyl are replaced by a fluoro group.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have 1-2 substituents, or 1-3 substituents, or 1-4 substituents, etc. Exemplary heteroalkyl substituents include esters (—C(O)—O—R) and carbonyls (—C(O)—).

"Heterocyclic" (or "heterocycloalkyl" or "heterocyclyl") refers to a non-aromatic saturated monocyclic or multicyclic ring system comprising 3 to 10 ring atoms (e.g., 3 to 7 ring atoms), or 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of heterocyclics or heterocycloalkyls include rings having 5 to 6 ring atoms. The prefix aza, oxa or thia before the heterocyclic or heterocycloalkyl root name means that at least a nitrogen, oxygen or sulfur atom, respectively, is present as a ring atom. The nitrogen or sulfur atom of the heterocyclic or heterocycloalkyl can be optionally oxidized to the corresponding N-oxide, S-oxide or S,S-dioxide. Any nitrogen atoms may be optionally quaternized. Non-limiting examples of monocyclic heterocyclic or heterocycloalkyl rings include: aziridinyl, piperidyl, pyrrolidinyl, pyrrolidino, piperazinyl, morpholinyl, thiomorpholinyl, thiazolidinyl, 1,3-dioxolanyl, 1,4-dioxanyl, tetrahydrofuranyl, tetrahydrothiophen-yl, and tetrahydrothiopyranyl. The heterocyclyl may be unsubstituted or substituted. In one embodiment, the heterocyclyl is unsubstituted. In another embodiment, the heterocyclyl is substituted. The substituted heterocyclyl ring may contain 1 substituent, or 1-2 substituents, or 1-3 substituents, or 1-4 substituents, etc. In one embodiment, the substituents that may be present on the heterocyclyl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) In one aspect, the R group which is, or is part of the substituent attached to the heterocyclic ring is an alkyl group having less than about 12 carbons, while in another aspect the R group is a lower alkyl group.

"Heterocycloalkylalkyl" means a heterocycloalkyl-alkyl group, wherein said heterocycloalkyl and said alkyl are as defined above, bound to a parent moiety through the alkyl group.

"Heteroaryl" means an aromatic monocyclic or multicyclic ring system comprising 5 to 14 ring atoms, or 5 to 10 ring atoms, in which one or more of the ring atoms is an element other than carbon, for example nitrogen, oxygen or sulfur, alone or in combination. Heteroaryls can contain 5 to 6 ring atoms. The prefix aza, oxa or thio before the heteroaryl root name means that at least a nitrogen, oxygen or sulfur atom respectively, is present as a ring atom. A nitrogen atom of a heteroaryl can be optionally oxidized to the corresponding N-oxide. Any nitrogen atoms may be optionally quaternized. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl. The heteroaryl may be unsubstituted or substituted. In one embodiment, the heteroaryl is unsubstituted. In another embodiment, the heteroaryl is substituted. The substituted heteroaryl ring may contain 1 substituent, or 1-2 substituents, or 1-3 substituents, or 1-4 substituents, etc. In one embodiment, the substituents that may be present on the heteroaryl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$) In one aspect, the R group which is, or is part of the substituent attached to the heteroaryl ring is an alkyl group having less than about 12 carbons, while in another aspect the R group is a lower alkyl group.

"Heteroaralkyl" or "heteroarylalkyl" means a heteroarylalkyl-group, in which the heteroaryl and alkyl are as previously described. Preferred heteroaralkyls can contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is H$_2$O.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "substituted" means substitution with specified groups other than hydrogen, or with one or more groups, moieties or radicals which can be the same or different, with each, for example, being independently selected.

II. Compositions

A comprehensive structure activity relationship study on DFP was conducted. Several new DFP-based KDM inhibitors which alter the velocity of HP1-mediated heterochromatin gene repression are provided.

The disclosed DFP-based KDM inhibitor compounds displayed tumor-selective cytotoxicity against the breast cancer (BCa) cell lines tested, with potency enhancement as high as 65-fold relative to DFP. Intriguingly, these compounds are preferentially more cytotoxic to the triple negative breast cancer (TNBC) cell line MDA-MB-231. Collectively, the data show that clinically approved DFP derives its anti-proliferative activity largely from the inhibition of a sub-set of KDMs. Excitingly the data demonstrate that DFP can serve as a new template for the discovery of tumor-selective KDM inhibitors.

A. New KDM Inhibitors

One embodiment provides a compound according to Formula I:

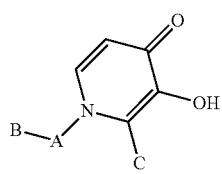

Formula I wherein A is —(CH$_2$)$_n$— n is 2-8,

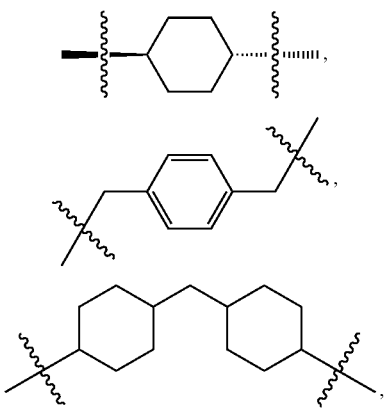

B is AR-AR', wherein AR' is a linking group connecting AR and A selected from the group consisting of

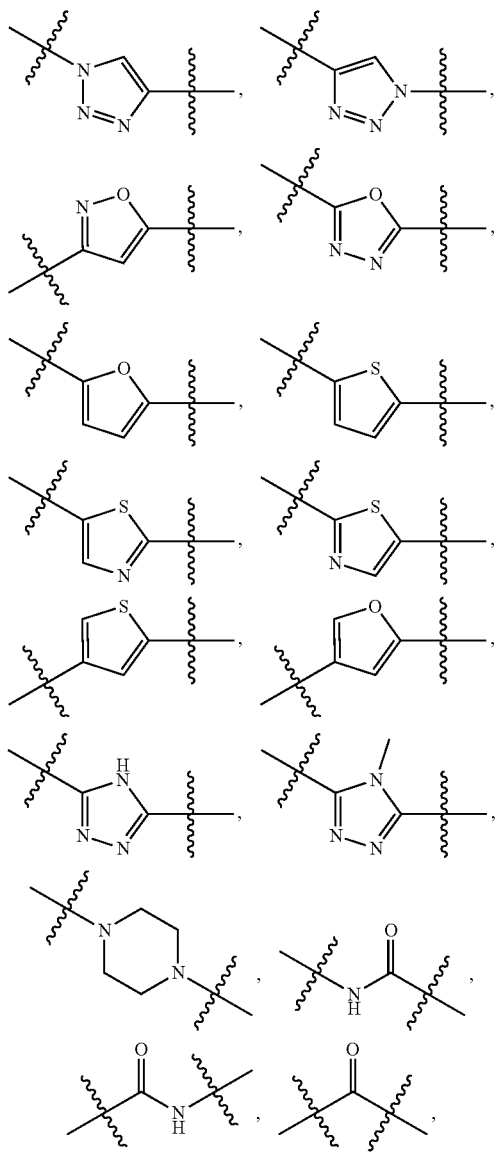

-continued

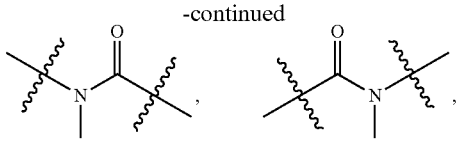

wherein AR is aryl, a 6-membered aromatic, heterocyclic, fused aromatic, fused heterocyclic, biaromatic, or bihetereocyclic ring system, optionally substituted by halogens, alkyl-, alkenyl-, and alkynyl groups,
wherein, when A is:

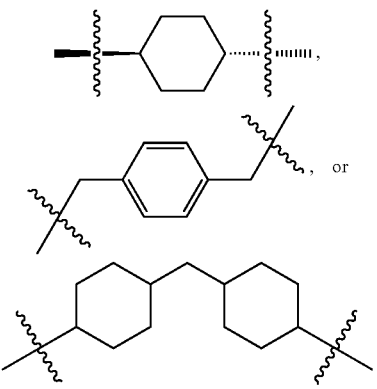

B is

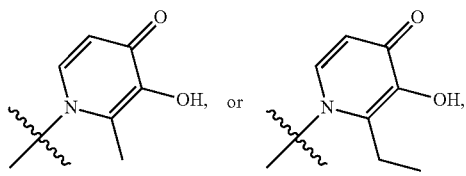

and
wherein C is alkyl, aryl; preferably methyl, ethyl, phenyl and pyridyl groups and the phenyl and pyridiyl groups are optionally substituted at the ortho, meta and para positions.

In one embodiment, "aryl" includes 6 membered single-ring aromatic groups that may include from zero to four heteroatoms, for example, benzene, pyridine, pyrazine, pyridazine and pyrimidine, and the like. Those awl having heteroatoms in the ring structure may also be referred to as "aryl heterocycles" or "heteroaromatics". In some embodiment, the term "aryl" also includes heterocyclic rings, wherein at least two of the rings are aromatic, linked together through tetra substituted alkene moiety or in which two or more carbons are common to two adjoining rings (the rings are "fused rings") wherein at least one of the rings is aromatic, e.g., the other rings can be cycloalkyls, cycloalkenyls, cycloalkynyls, aryls and/or heterocycles. The aromatic ring can be substituted at one or more ring positions with such substituents as described above, for example, halogen, alkyl, aralkyl, alkenyl, alkynyl, cycloalkyl, hydroxyl, alkoxyl, amino, nitro, sulfhydryl, imino, amido, carbonyl, carboxyl, silyl, ether, alkylthio, sulfonyl, sulfonamido, ketone, aldehyde, ester, heterocyclyl, aromatic or heteroaromatic moieties, —CF$_3$, —CN, tetra substituted alkenes, wherein at least two of the rings are aromatic, linked through alkoxylamino moiety or the like.

One embodiment provides the compound 2j named 3-Hydroxy-1-(5-(4-(3-methoxyphenyl)-1H-1,2,3-triazol-1-yl)pentyl)-2-methylpyridin-4(1H)-one, or the hydrate thereof, or the solvate thereof, or the pharmaceutically acceptable salt thereof or the resolved single isomer thereof.

One embodiment provides compound 2t named 3-Hydroxy-2-methyl-1-(5-(4-(4-(pyridin-4-yl)phenyl)-1H-1,2,3-triazol-1-yl)pentyl)pyridin-4(1H)-one or the pharmaceutically acceptable salt thereof or the resolved single isomer thereof. Another embodiment provides a pharmaceutical composition containing compound 2t. In still another embodiment provides a pharmaceutical composition containing an effective amount of compound 2v to inhibit one or more histone lysine demethylases when administered to a subject in need thereof.

One embodiment provides the compound 2v named 1-(6-(4-([1,1}-Biphenyl]-4-yl)-1H-1,2,3-triazol-1-yl)hexyl)-3-hydroxy-2-methylpyridin-4(1H)-one or the pharmaceutically acceptable salt thereof or the resolved single isomer thereof. Another embodiment provides a pharmaceutical composition containing compound 2v. In still another embodiment provides a pharmaceutical composition containing an effective amount of compound 2t to inhibit one or more histone lysine demethylases when administered to a subject in need thereof.

Still another embodiment provides the compound 2w named 3-Hydroxy-1-(6-(4-(6-methoxynaphthalen-2-yl)-1H-1,2,3-triazol-1-yl)hexyl)-2-methylpyridin-4(1H)-one or the pharmaceutically acceptable salt thereof or the resolved single isomer thereof. Another embodiment provides a pharmaceutical composition containing compound 2w. In still another embodiment provides a pharmaceutical composition containing an effective amount of compound 2w to inhibit one or more histone lysine demethylases when administered to a subject in need thereof.

Yet another embodiment provides the compound 3g named 1,1'-(Methylenebis(cyclohexane-4,1-diyl))bis(3-hydroxy-2-methylpyridin-4(1H)-one) or the pharmaceutically acceptable salt thereof or the resolved single isomer thereof. Another embodiment provides a pharmaceutical composition containing compound 3g. In still another embodiment provides a pharmaceutical composition containing an effective amount of compound 3g to inhibit one or more histone lysine demethylases when administered to a subject in need thereof.

Figure 7A:
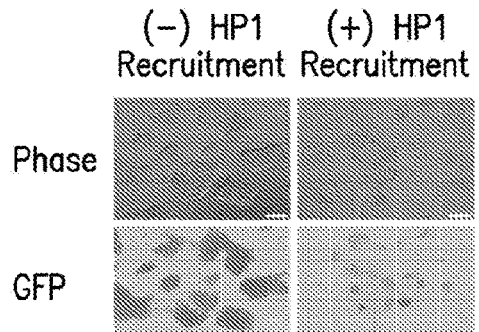
FIG. 7A is panel of microphotographs showing reduction of GFP expression after HP1 recruitment.
Figure 7B:
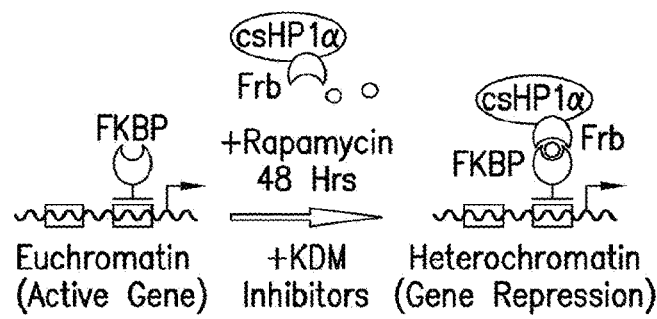
FIG. 7B is a cartoon schematic of the chromatin in vivo assay (CiA) and recruitment of HP1 by CIP-rapamycin addition leads to gene silencing Dose response curves of DFP derivatives after 48 h with (7C) and without (7D) HP1 recruitment at 10000, 5000 2500, 1000, 500, 250, and 0 nM concentrations. Flow cytometry was used to determine the % GFP (+) cells following treatment. n=6.
Figure 7C:
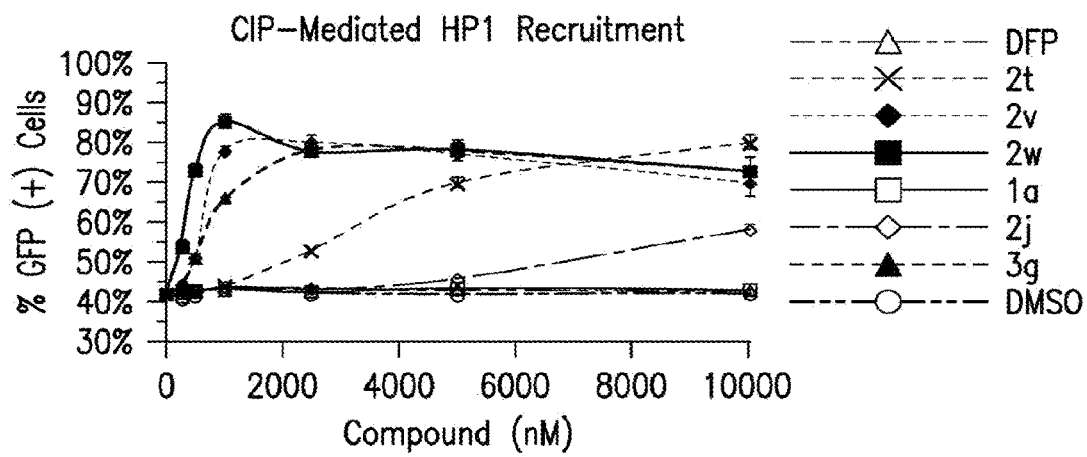
Figure 7D:
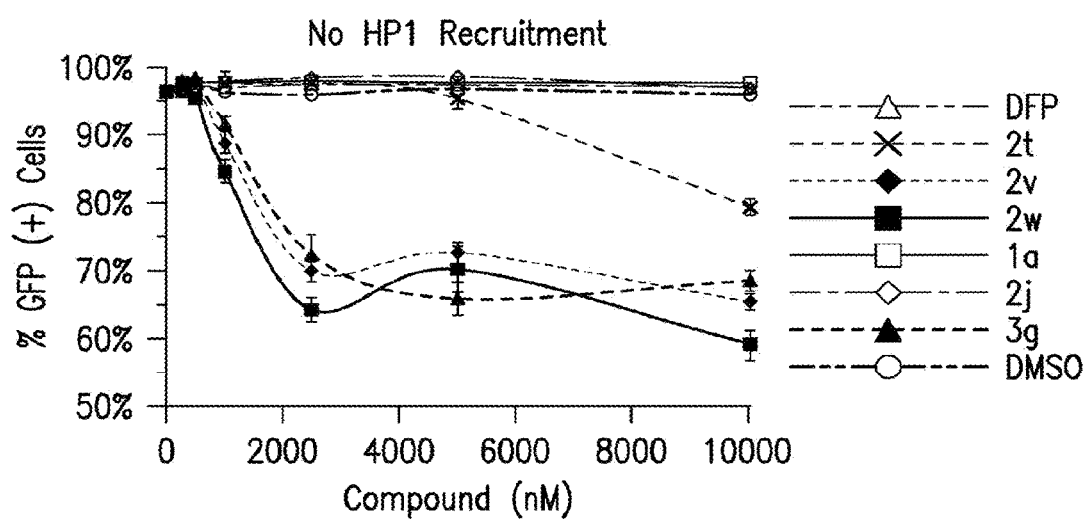

One embodiment provides compounds 1a-14, 2a-2w, and 3a-3g, 36a-g. FIG. 7A is panel of microphotographs showing reduction of GFP expression after HP1 recruitment. FIG. 7B is a cartoon schematic of the chromatin in vivo assay (CiA) and recruitment of HP1 by CIP-rapamycin addition leads to gene silencing Dose response curves of DFP derivatives after 48 h with (7C) and without (7D) HP1 recruitment at 10000, 5000 2500, 1000, 500, 250, and 0 nM concentrations. Flow cytometry was used to determine the % GFP (+) cells following treatment. n=6.

One embodiment provides the following compound:

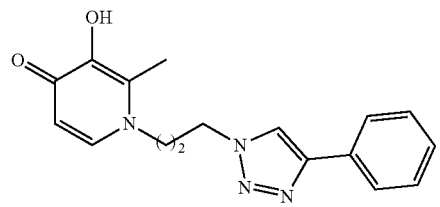 [SMILES: Cc1c(O)c(=O)ccn1CCn1cc(-c2ccccc2)nn1]

or the pharmaceutically acceptable salt thereof or the resolved single isomer thereof.

One embodiment provides the following compound:

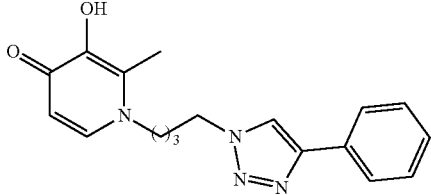 [SMILES: Cc1c(O)c(=O)ccn1CCn1cc(-c2ccccc2)nn1]

or the pharmaceutically acceptable salt thereof or the resolved single isomer thereof.

One embodiment provides the following compound:

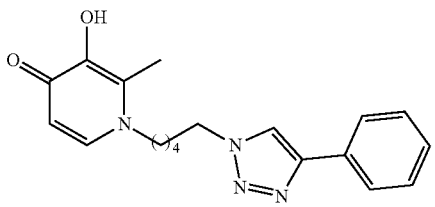 [SMILES: Cc1c(O)c(=O)ccn1CCn1cc(-c2ccccc2)nn1]

or the pharmaceutically acceptable salt thereof or the resolved single isomer thereof.

One embodiment provides the following compound:

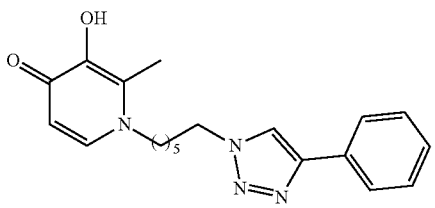

or the pharmaceutically acceptable salt thereof or the resolved single isomer thereof.

One embodiment provides the following compound:

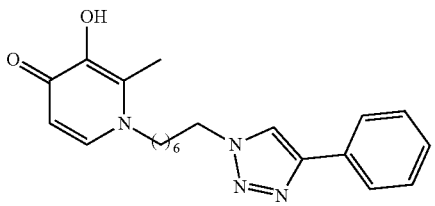 [SMILES: Cc1c(O)c(=O)ccn1CCn1cc(-c2ccccc2)nn1]

or the pharmaceutically acceptable salt thereof or the resolved single isomer thereof.

One embodiment provides the following compound:

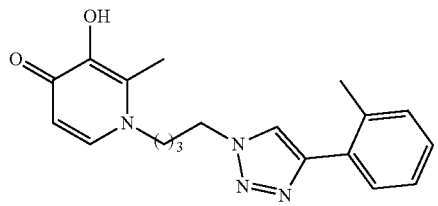

or the pharmaceutically acceptable salt thereof or the resolved single isomer thereof.

One embodiment provides the following compound:

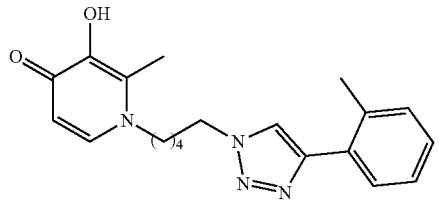 [SMILES: Cc1ccccc1-c1cn(CCn2ccc(=O)c(O)c2C)nn1]

or the pharmaceutically acceptable salt thereof or the resolved single isomer thereof.

One embodiment provides the following compound:

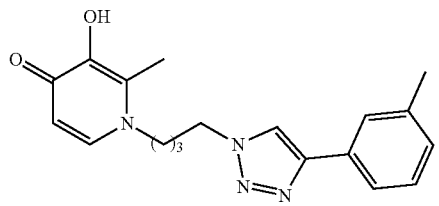

or the pharmaceutically acceptable salt thereof or the resolved single isomer thereof.

One embodiment provides the following compound:

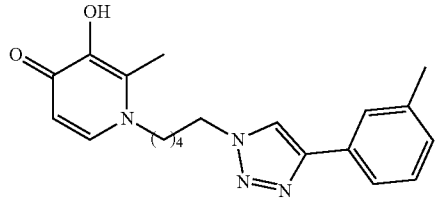

or the pharmaceutically acceptable salt thereof or the resolved single isomer thereof.

One embodiment provides the following compound:

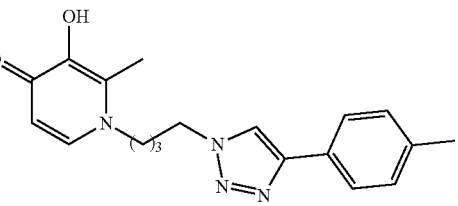

or the pharmaceutically acceptable salt thereof or the resolved single isomer thereof.

One embodiment provides the following compound:

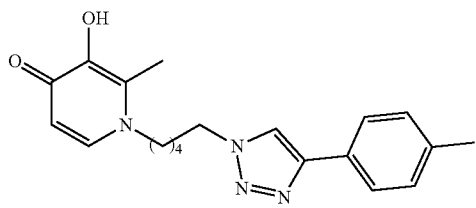

or the pharmaceutically acceptable salt thereof or the resolved single isomer thereof.

One embodiment provides the following compound:

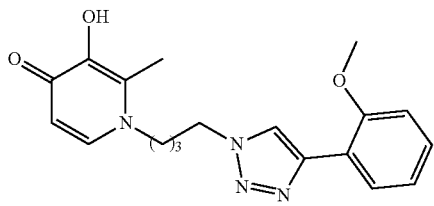

or the pharmaceutically acceptable salt thereof or the resolved single isomer thereof.

One embodiment provides the following compound:

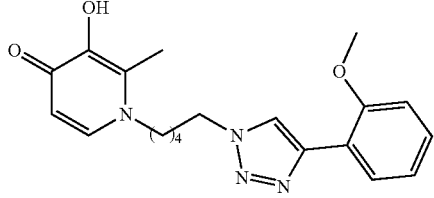

or the pharmaceutically acceptable salt thereof or the resolved single isomer thereof.

One embodiment provides the following compound:

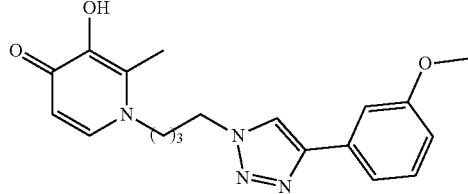

or the pharmaceutically acceptable salt thereof or the resolved single isomer thereof.

One embodiment provides the following compound:

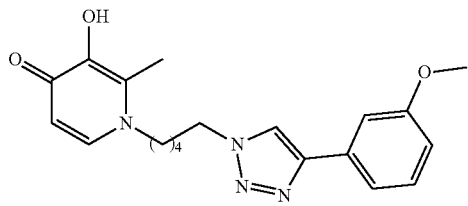

or the pharmaceutically acceptable salt thereof or the resolved single isomer thereof.

One embodiment provides the following compound:

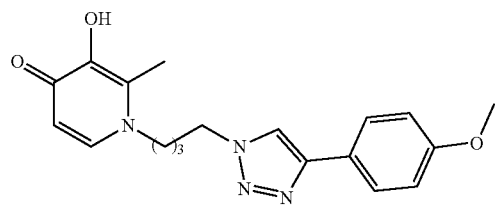

or the pharmaceutically acceptable salt thereof or the resolved single isomer thereof.

One embodiment provides the following compound:

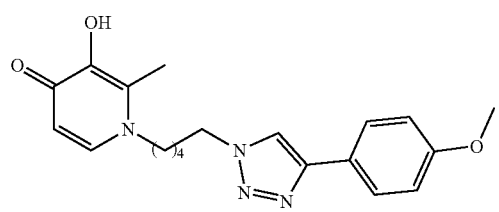

or the pharmaceutically acceptable salt thereof or the resolved single isomer thereof.

One embodiment provides the following compound:

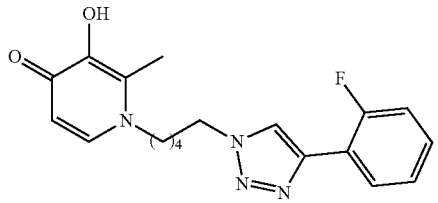

or the pharmaceutically acceptable salt thereof or the resolved single isomer thereof.

One embodiment provides the following compound:

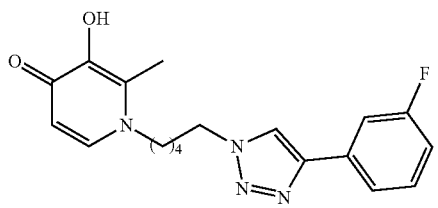

or the pharmaceutically acceptable salt thereof or the resolved single isomer thereof.

One embodiment provides the following compound:

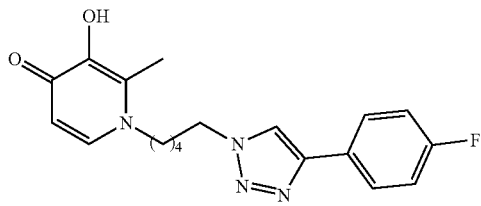

or the pharmaceutically acceptable salt thereof or the resolved single isomer thereof.

One embodiment provides the following compound:

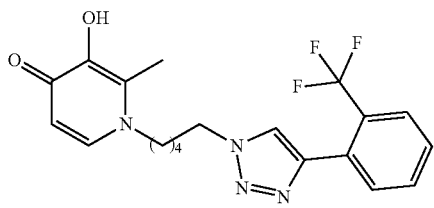

or the pharmaceutically acceptable salt thereof or the resolved single isomer thereof.

One embodiment provides the following compound:

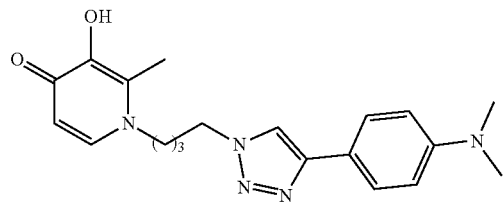

or the pharmaceutically acceptable salt thereof or the resolved single isomer thereof.

One embodiment provides the following compound:

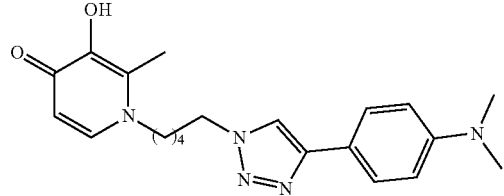

or the pharmaceutically acceptable salt thereof or the resolved single isomer thereof.

One embodiment provides the following compound:

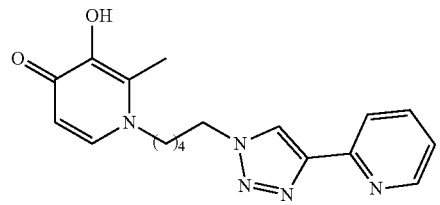

or the pharmaceutically acceptable salt thereof or the resolved single isomer thereof.

One embodiment provides the following compound:

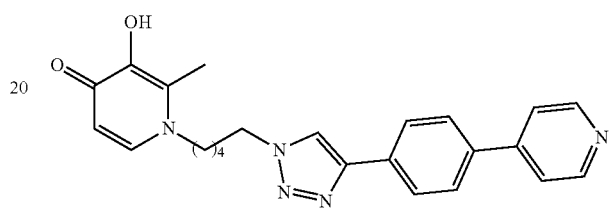

or the pharmaceutically acceptable salt thereof or the resolved single isomer thereof.

One embodiment provides the following compound:

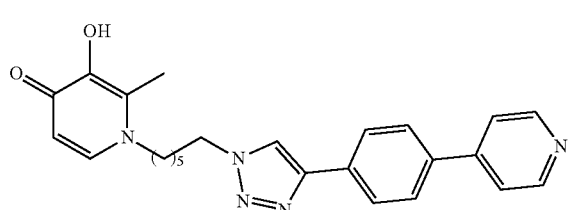

or the pharmaceutically acceptable salt thereof or the resolved single isomer thereof.

One embodiment provides the following compound:

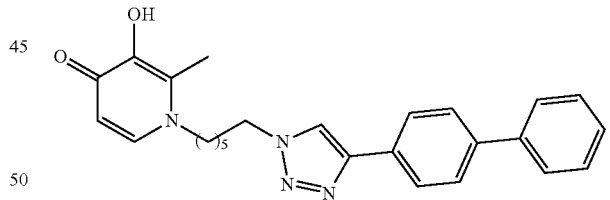

or the pharmaceutically acceptable salt thereof or the resolved single isomer thereof.

One embodiment provides the following compound:

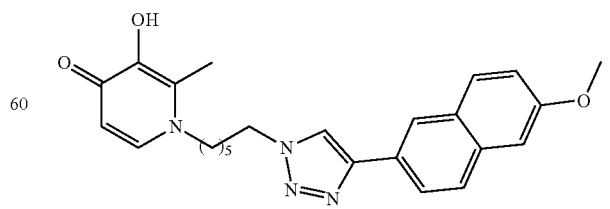

or the pharmaceutically acceptable salt thereof or the resolved single isomer thereof.

One embodiment provides the following compound:

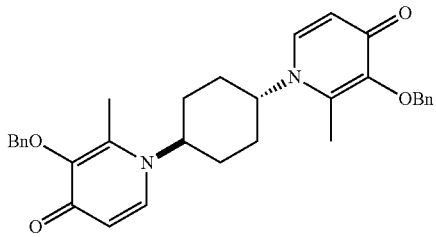

or the pharmaceutically acceptable salt thereof or the resolved single isomer thereof.

One embodiment provides the following compound:

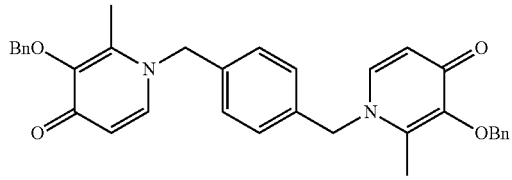 [SMILES: Cc1c(OCc2ccccc2)c(=O)ccn1Cc1ccc(Cn2ccc(=O)c(OCc3ccccc3)c2C)cc1]

or the pharmaceutically acceptable salt thereof or the resolved single isomer thereof.

One embodiment provides the following compound:

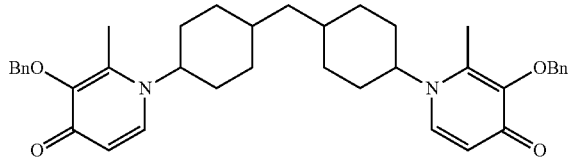 [SMILES: Cc1c(OCc2ccccc2)c(=O)ccn1C1CCC(CC2CCC(n3ccc(=O)c(OCc4ccccc4)c3C)CC2)CC1]

or the pharmaceutically acceptable salt thereof or the resolved single isomer thereof.

One embodiment provides the following compound:

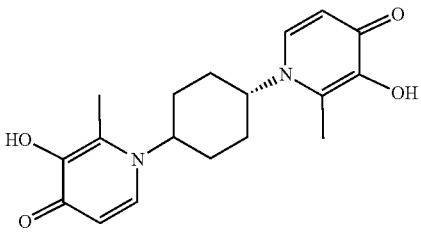

or the pharmaceutically acceptable salt thereof or the resolved single isomer thereof.

One embodiment provides the following compound:

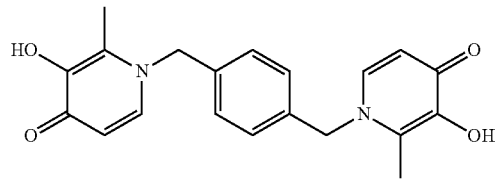 [SMILES: Cc1c(O)c(=O)ccn1Cc1ccc(Cn2ccc(=O)c(O)c2C)cc1]

or the pharmaceutically acceptable salt thereof or the resolved single isomer thereof.

One embodiment provides the following compound:

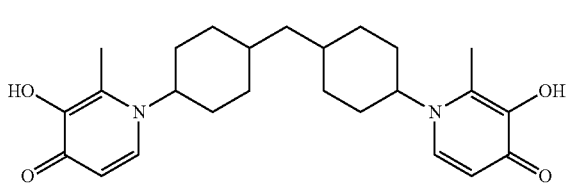 [SMILES: Cc1c(O)c(=O)ccn1C1CCC(CC2CCC(n3ccc(=O)c(O)c3C)CC2)CC1]

or the pharmaceutically acceptable salt thereof or the resolved single isomer thereof.

One embodiment provides the following compound:

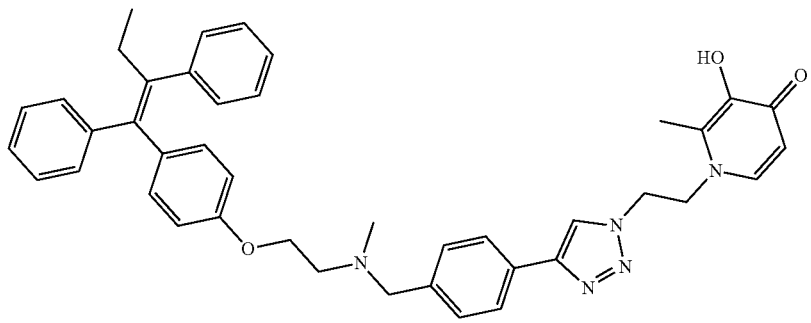 [SMILES: CC/C(=C(\c1ccccc1)c1ccc(OCCN(C)Cc2ccc(-c3cn(CCn4ccc(=O)c(O)c4C)nn3)cc2)cc1)c1ccccc1]

or the pharmaceutically acceptable salt thereof or the resolved single isomer thereof.

One embodiment provides the following compound:

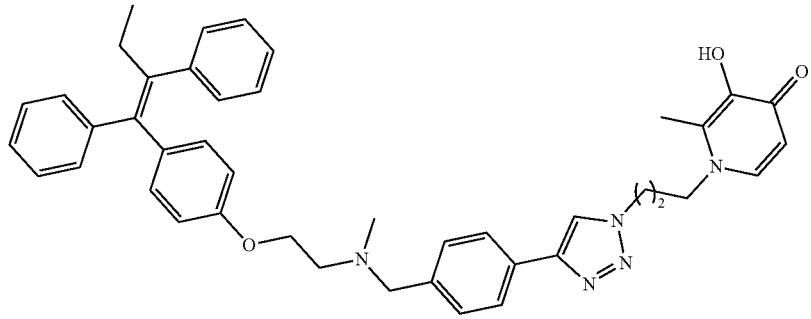

or the pharmaceutically acceptable salt thereof or the resolved single isomer thereof.

One embodiment provides the following compound:

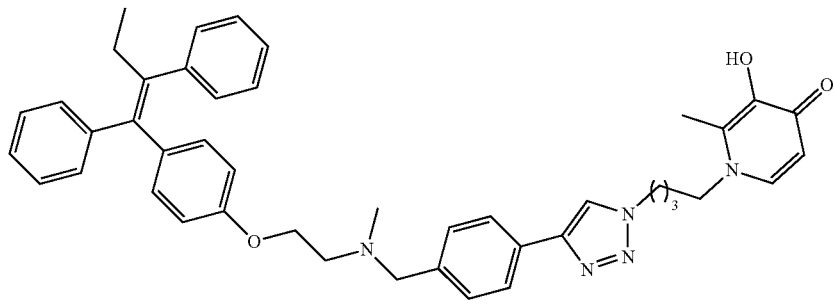

or the pharmaceutically acceptable salt thereof or the resolved single isomer thereof.

One embodiment provides the following compound:

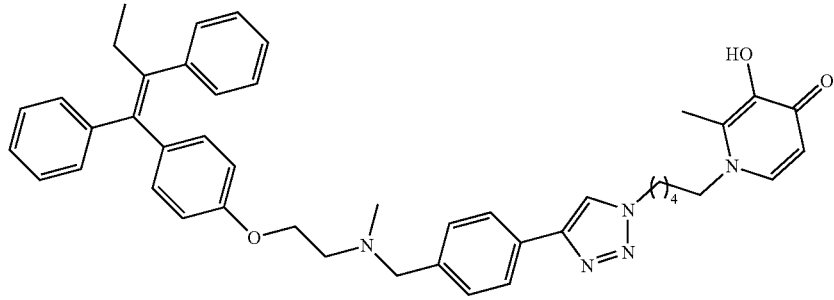

or the pharmaceutically acceptable salt thereof or the resolved single isomer thereof.

One embodiment provides the following compound:

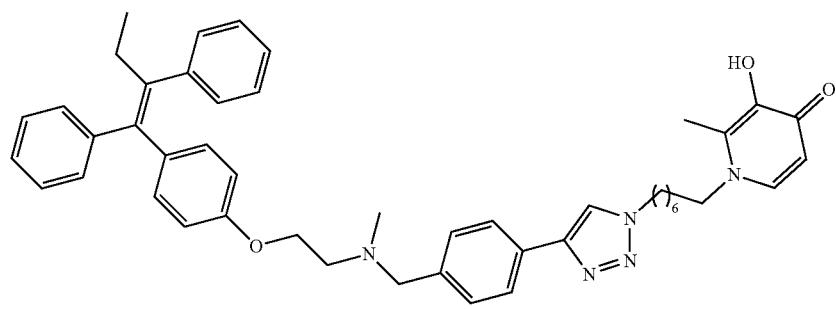

or the pharmaceutically acceptable salt thereof or the resolved single isomer thereof.

One embodiment provides the following compound:

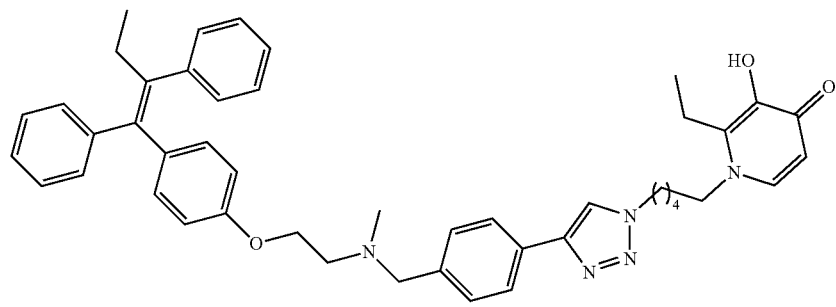

or the pharmaceutically acceptable salt thereof or the resolved single isomer thereof

III. Methods of Use

The disclosed compounds and pharmaceutical compositions can be used to inhibit proliferation of cells, for example cancer or tumor cells. One embodiment provides a method for inhibiting tumor growth in a subject in need thereof by administering an effective amount of one or more the disclosed DFP derivatives including but not limited to compounds 1a-1f, 2l-2w, 3a-3g, and 36a-36g or or the pharmaceutically acceptable salt thereof or the resolved single isomer thereof.

One embodiment provides a method of treatment including administering an effective amount of one or more compounds 1a-1f, 2l-2w, 3a-3g, and 36a-36g or the pharmaceutically acceptable salt thereof or the resolved single isomer thereof to a subject in need thereof to reduce tumor burden, inhibit tumor growth, or both. In some embodiment, the subject has or is suspected of having cancer. Exemplary cancers that can be treated with the disclosed compositions include but are not limited to breast cancer, prostate cancer, head and neck cancer, lung cancer, ovarian cancer, pancreatic cancer, liver cancer, esophageal cancer, stomach cancer, bone cancer, muscle cancer, or skin cancer.

EXAMPLES

Example 1: Characterization of Inhibitors

Compounds that were synthesized listed in the Tables below.

TABLE 1

KDM6A Activity Inhibition (%) of 1a-f and 2a-w at 1 μM and 10 μM.

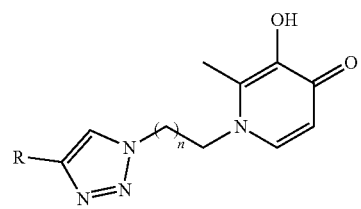

KDM6A (UTX) Inhibition (%)

| Compound | R | n | 1 (μM) | 10 (μM) |
|---|---|---|---|---|
| 1a | phenyl | 1 | 12 | 96 |
| 1b | phenyl | 2 | 6 | 100 |
| 1c | phenyl | 3 | 8 | 100 |

TABLE 1-continued

| | | | | |
|---|---|---|---|---|
| 1d | phenyl | 4 | 12 | 100 |
| 1e | phenyl | 5 | 12 | 98 |
| 1f | phenyl | 6 | 10 | 99 |
| 2a | 2-methylphenyl | 3 | 6 | 100 |
| 2c | 3-methylphenyl | 3 | 4 | 100 |
| 2e | 4-methylphenyl | 3 | 13 | 100 |
| 2h | 2-methoxyphenyl | 4 | 3 | 99 |
| 2i | 3-methoxyphenyl | 3 | 7 | 100 |
| 2j | 3-methoxyphenyl | 4 | 8 | 100 |
| 2l | 4-methoxyphenyl | 4 | 4 | 100 |
| 2m | 2-fluorophenyl | 4 | 16 | 100 |
| 2n | 3-fluorophenyl | 4 | 5 | 100 |
| 2o | 4-fluorophenyl | 4 | 10 | 100 |
| 2p | 2-CF3-phenyl | 4 | 15 | 99 |
| 2s | 2-pyridyl | 4 | 15 | 99 |
| 2t | 4-(pyridin-4-yl)phenyl | 4 | 8 | 99 |

TABLE 2

KDM6A Inhibition Activity of 3a-c at 1 µM and 10 µM.

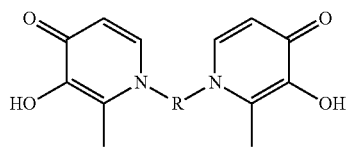

KDM6A (UTX) Inhibition (%)

| Compound | R | (1 µM) | (10 µM) |
|---|---|---|---|
| 3e | cyclohexyl-1,4-diyl | 5 | 100 |
| 3f | 1,4-bis(methylene)phenyl | 5 | 100 |
| 3g | bis(cyclohexyl)methane | 9 | 100 |

TABLE 3

KDM6A Inhibition Activity of 36a-g at 1 μM and 10 μM.

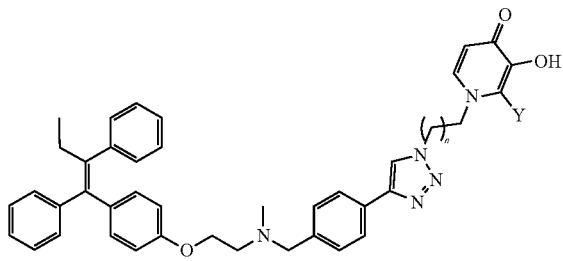

| Compound | Y | n | % inhibition (1 μM) | % inhibition (10 μM) |
|---|---|---|---|---|
| 36a | CH₃ | 1 | 9 | 100 |
| 36b | CH₃ | 2 | 22 | 100 |
| 36c | CH₃ | 3 | 11 | 99 |
| 36d | CH₃ | 4 |  | 100 |
| 36e | CH₃ | 5 | 91 | 100 |
| 36f | CH₃ | 6 | 10 | 100 |
| 36g | C₂H₅ | 4 |  |  |

TABLE 4

Antiproliferative Activity of Compounds 1a-f.

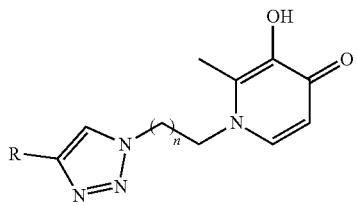

Antiproliferative Activity IC$_{50}$ (μM)

| Compound | n | MDA-MB-231 | MCF-7 | VERO |
|---|---|---|---|---|
| 1a | 1 | >50 | ND$^a$ | >100 |
| 1b | 2 | 25.1 | ND | >50 |
| 1c | 3 | 16.4 | ND | >50 |
| 1d | 4 | 12.5 | ND | >50 |
| 1e | 5 | 11.4 | ND | >35 |
| 1f | 6 | 10.5 | ND | 17.6 |
| DFP | — | 111.9 | 134.1 | 85.89 |

$^a$ND, not determinable

TABLE 5

Antiproliferative Activity of Compounds 2a-w.

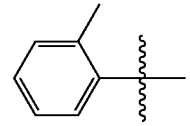

Anti-proliferative Activity IC$_{50}$ (μM)

| Compound | R | n | MDA-MB-231 | MCF-7 | VERO |
|---|---|---|---|---|---|
| 2a | 2-methylphenyl | 3 | 16.4 | ND$^a$ | 11.6 |
| 2b | 2-methylphenyl | 4 | 12.7 | ND | 1.8 |
| 2c | 3-methylphenyl | 3 | 10.9 | ND | 5.2 |
| 2d | 3-methylphenyl | 4 | 11.8 | ND | 3.6 |

TABLE 5-continued

Antiproliferative Activity of Compounds 2a-w.

[Structure: 3-hydroxy-2-methyl-1-[(CH2)n-triazole-R]-pyridin-4(1H)-one]

Anti-proliferative Activity IC$_{50}$ (μM)

| Compound | R | n | MDA-MB-231 | MCF-7 | VERO |
|---|---|---|---|---|---|
| 2e | 4-methylphenyl | 3 | 7.4 | ND | 4.1 |
| 2f | 4-methylphenyl | 4 | 15.7 | ND | 3.1 |
| 2g | 2-methoxyphenyl | 3 | 9.6 | ND | >50 |
| 2h | 2-methoxyphenyl | 4 | 19.1 | ND | >50 |
| 2i | 3-methoxyphenyl | 3 | 7.5 | ND | >50 |
| 2j | 3-methoxyphenyl | 4 | 10.6 | ND | >50 |
| 2k | 4-methoxyphenyl | 3 | 8.1 | ND | >50 |
| 2l | 4-methoxyphenyl | 4 | 9.6 | ND | >50 |
| 2m | 2-fluorophenyl | 4 | 18.3 | ND | 12.7 |

TABLE 5-continued

Antiproliferative Activity of Compounds 2a-w.

Anti-proliferative Activity IC$_{50}$ (μM)

| Compound | R | n | MDA-MB-231 | MCF-7 | VERO |
|---|---|---|---|---|---|
| 2n | 3-F-phenyl | 4 | 6.8 | ND | 22.9 |
| 2o | 4-F-phenyl | 4 | 3.6 | ND | 38.8 |
| 2p | 2-CF$_3$-phenyl | 4 | 18.8 | ND | 13.3 |
| 2q | 4-(dimethylamino)phenyl | 3 | 9.5 | ND | >50 |
| 2r | 4-(dimethylamino)phenyl | 4 | 12.5 | ND | >50 |
| 2s | 2-pyridyl | 4 | NI[b] | ND | NI |
| 2t | 4-(pyridin-4-yl)phenyl | 4 | 3.6 | ND | 29.2 |
| 2u | 4-(pyridin-4-yl)phenyl | 3 | 1.7 | ND | 66.9 |
| 2v | biphenyl | 3 | 2.5 | ND | 4.9 |

TABLE 5-continued

Antiproliferative Activity of Compounds 2a-w.

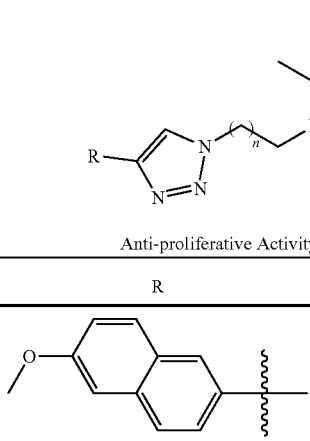

Anti-proliferative Activity IC$_{50}$ (μM)

| Compound | R | n | MDA-MB-231 | MCF-7 | VERO |
|---|---|---|---|---|---|
| 2x | (6-methoxynaphthalen-2-yl) | 5 | 1.2 | ND | 3.9 |

[a]ND, not determinable
[b]NI, no inhibition

TABLE 6

Antiproliperative Activity of Compounds 3a-c.

| Compound | R | MDB-MD-231 IC$_{50}$ (μM) | MCF-7 IC$_{50}$ (μM) | Vero IC$_{50}$ (μM) |
|---|---|---|---|---|
| 3e | cyclohexane-1,4-diyl | 36.9 | [a]ND | [b]NI |
| 3f | 1,4-phenylenebis(methylene) | 25.0 | ND | NI |
| 3g | methylenebis(cyclohexane-4,1-diyl) | 3.50 | ND | NI |

[b]NI (No inhibition)

TABLE 7

Antiproliferative Activity of Compounds 36a-g.

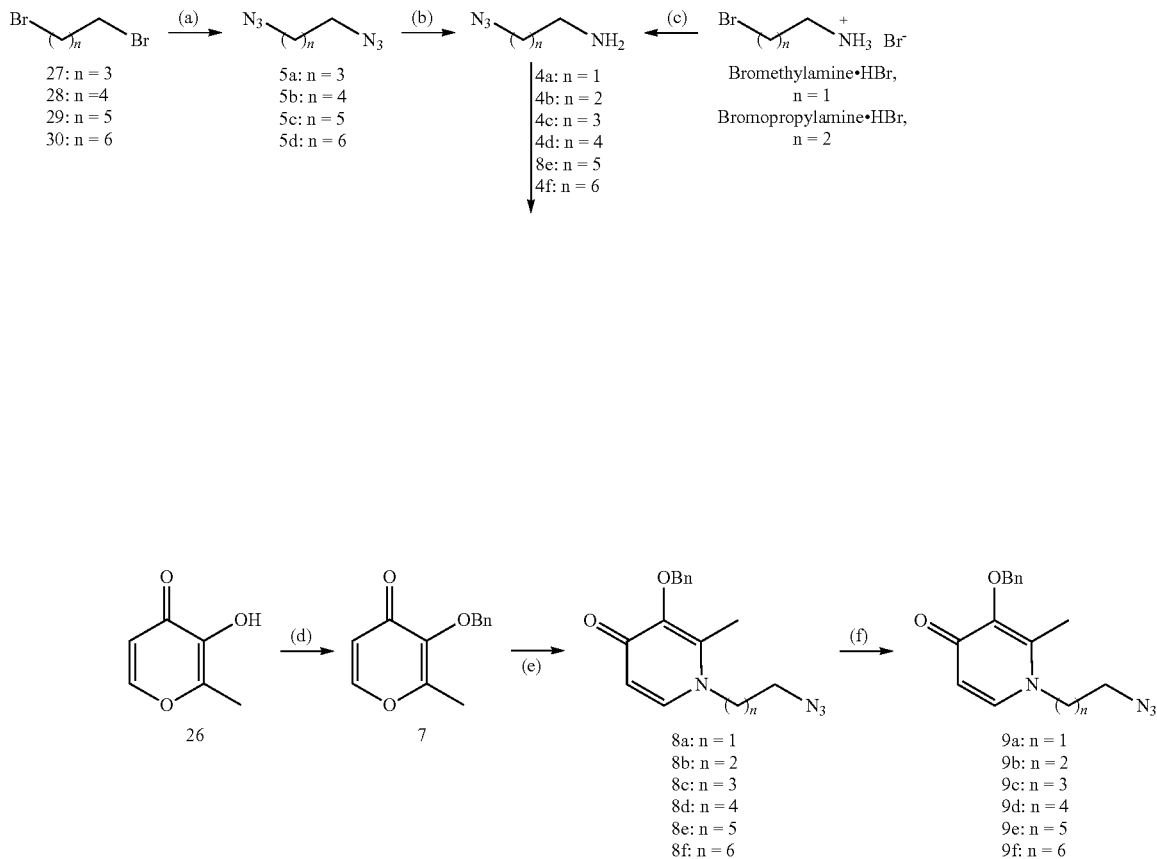

| Compound | Y | n | MDB-MB-231 IC$_{50}$ (μM) | MCF-7 IC$_{50}$ (μM) | Vero IC$_{50}$ (μM) |
|---|---|---|---|---|---|
| 36a | CH$_3$ | 1 | 1.6 | 1.4 | 3.5 |
| 36b | CH$_3$ | 2 | 1.5 | 1.9 | 3.9 |
| 36c | CH$_3$ | 3 | 0.7 | 0.5 | 2.3 |
| 36d | CH$_3$ | 4 | 0.8 | 0.4 | 2.8 |
| 36e | CH$_3$ | 5 | 0.7 | 0.4 | 2.5 |
| 36f | CH$_3$ | 6 | 0.9 | 2.7 | 4.0 |
| 36g | C$_2$H$_5$ | 4 | 0.6 | 0.3 | |

Cell viability assay: All cell lines were purchased form ATCC (Manassas, VA) and they were routinely cultured in different media recommended by the supplier. Prior to addition of 3-(hydroxy) pyridin-4(1H)-one compounds (the subject of this invention), cell lines were plated onto a 96 well plate (Techno Plastic Products AG, Trasadingen, Switzerland) using non-phenol red DMEM with cell density of 4500 cells/100 μL. After 24 h incubation at 37° C. under 5% CO$_2$, cells were treated with serially diluted 3-(hydroxy)-pyridin-4(1H)-one compounds with final DMSO concentration of 1% and incubated for additional 72 h. MTS (CellTiter 96 Aqueous One Solution Cell Proliferation Assays, Promega, Madison, WI) was added to each well 2.5 h prior to recording the absorbance at 490 nm.

Example II: Synthesis of Compounds 1a-1f and 2a-2w

Scheme 1: Synthesis of Azidoalkyl-3-hydroxypyridin-4-one.

Reagents and conditions: (a) NaN$_3$, DMF, 80° C., 20 h; (b) PPh$_3$, 5% HCl, EtOAC:Ether, 40 h; (c) (1) NaN$_3$, H$_2$O, 80° C., 12 h; (2) aq KOH; (d) benzyl chloride, K$_2$CO$_3$, DMF, 110° C., 3 h; (e) NaOH, EtOH:H$_2$O, 110° C. under pressure, 72 h; (f) conc. HCl, 4-6 h.

Scheme 2

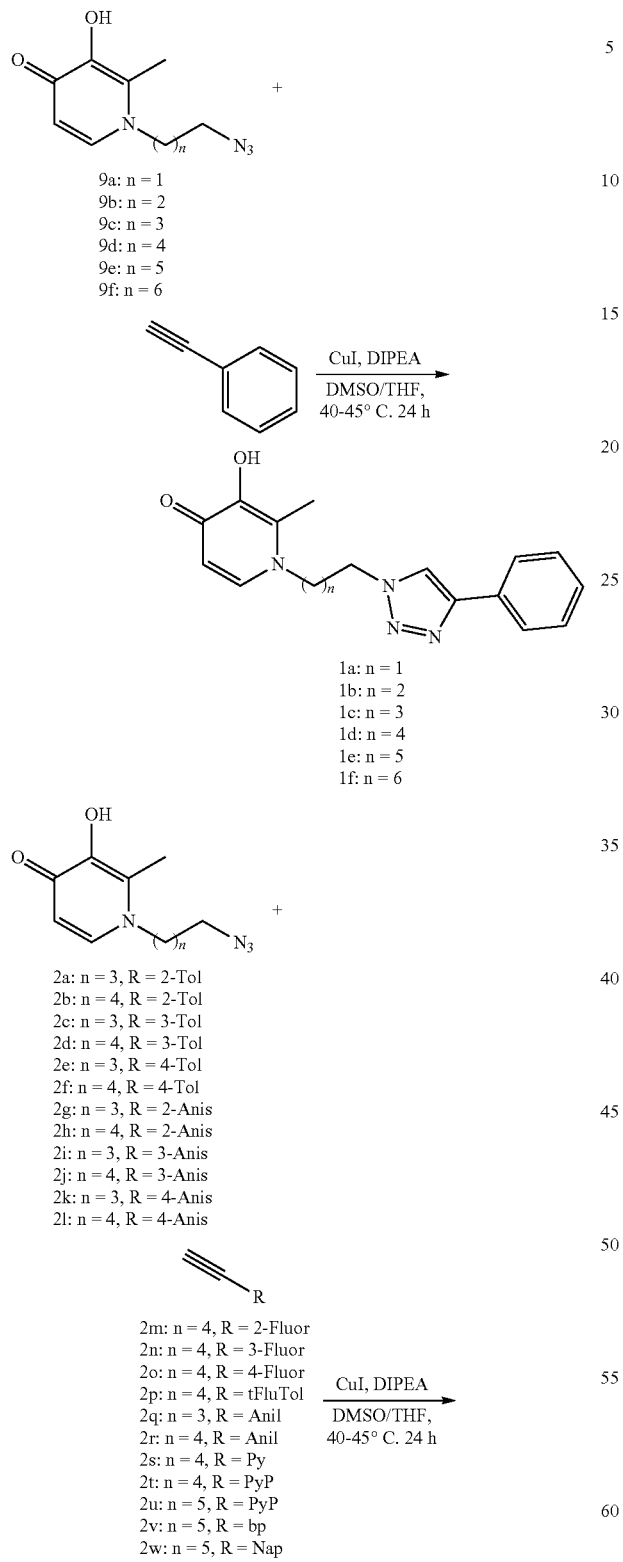

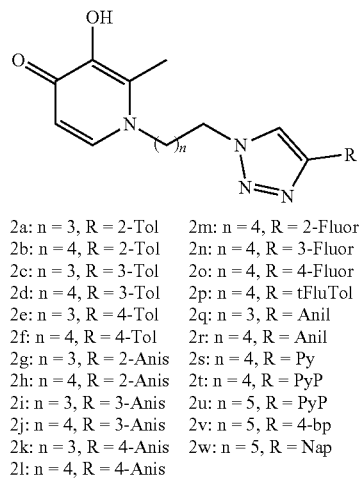

2a: n = 3, R = 2-Tol    2m: n = 4, R = 2-Fluor
2b: n = 4, R = 2-Tol    2n: n = 4, R = 3-Fluor
2c: n = 3, R = 3-Tol    2o: n = 4, R = 4-Fluor
2d: n = 4, R = 3-Tol    2p: n = 4, R = tFluTol
2e: n = 3, R = 4-Tol    2q: n = 3, R = Anil
2f: n = 4, R = 4-Tol    2r: n = 4, R = Anil
2g: n = 3, R = 2-Anis   2s: n = 4, R = Py
2h: n = 4, R = 2-Anis   2t: n = 4, R = PyP
2i: n = 3, R = 3-Anis   2u: n = 5, R = PyP
2j: n = 4, R = 3-Anis   2v: n = 5, R = 4-bp
2k: n = 3, R = 4-Anis   2w: n = 5, R = Nap
2l: n = 4, R = 4-Anis Synthesis of triazole containing KDM inhibitors (1a-f and 2a-w). Abbreviation: 2-Tol, 2-tolyl; 3-Tol, 3-tolyl; 4-Tol, 4-tolyl; 2-Anis, 2-anisolyl; 3-Anis 3-anisolyl; 4-Anis, 4-anisolyl; 2-Fluor, 2-fluoryl; 3-Fluor, 3-fluoryl; 4-Fluor, 4-fluoryl; tFluTol; α,α,α-trifluorotolyl; Anil, 4-anilyl; 4-Py, 4-pyridyl; PyP, 4-pyridylphenyl; 4-bp, 4-biphenyl; Nap, 6-methoxynapthyl.

Example III: Synthesis of Compounds 3a-c

Scheme 3

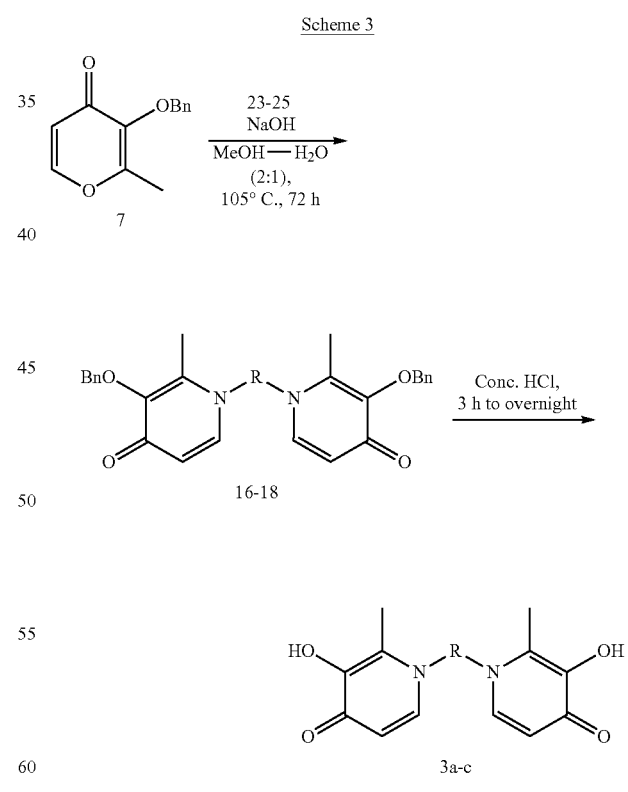

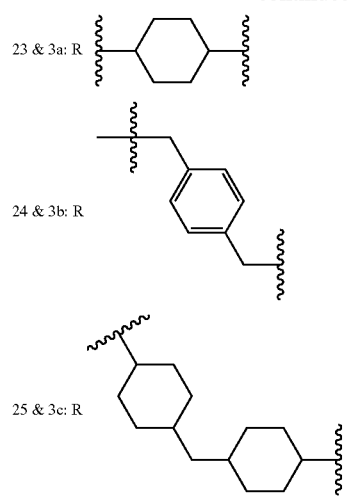
Example IV—Synthesis of Compounds 36a-36g
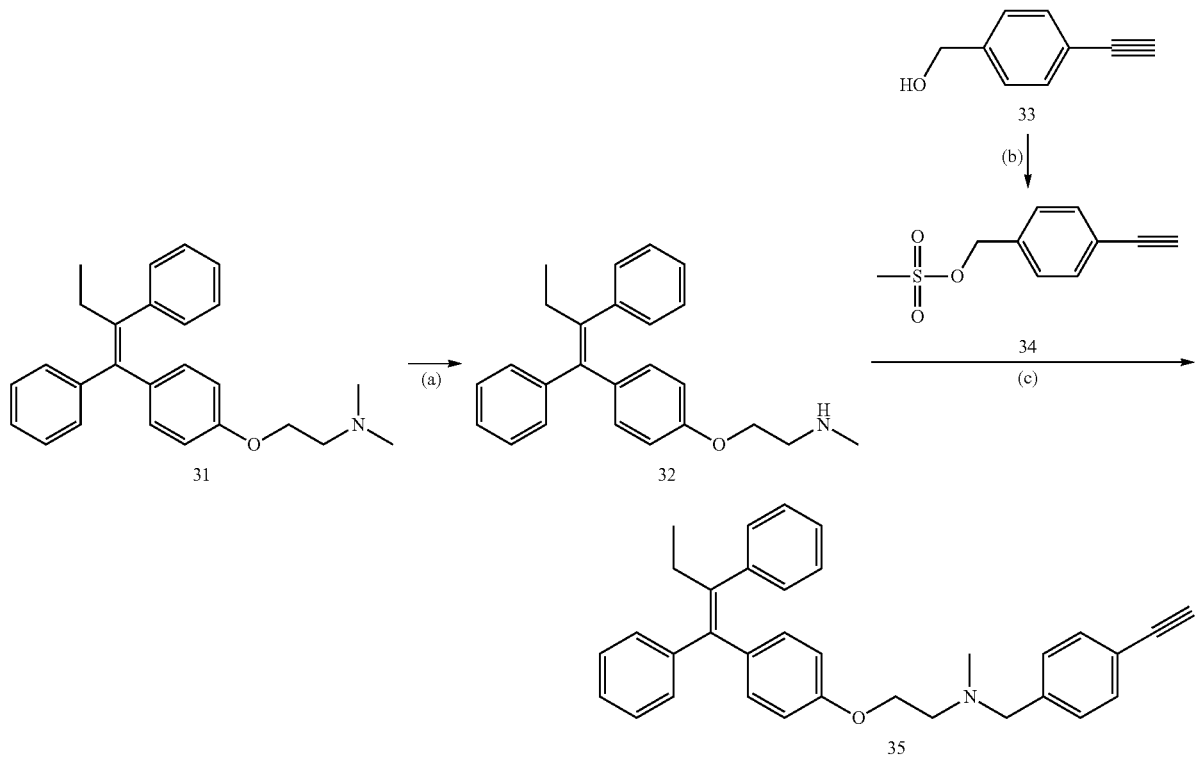
Scheme 4

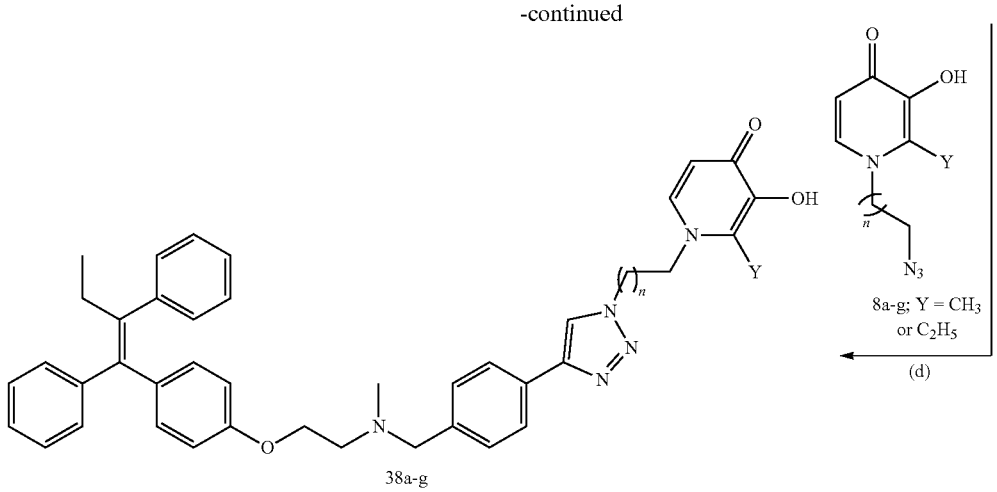

<sup>a</sup>Reagents and conditions: (a) (1)1-chloroethyl chloroformate, DCM, reflux, 24 h; (2) MeOH, reflux, 3 h; (b) methylsulfonyl chloride, Et$_3$N, DCM, -10° C., 40 min; (c) DIPEA, DMSO, 85° C., 4 h; (d) CuI, DIPEA, DMSO,, 24 h.

Example V: Specific Inhibitors

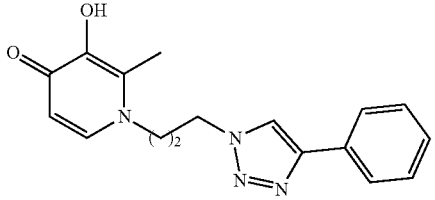

3-Hydroxy-2-methyl-1-(2-(4-phenyl-1H-1,2,3-triazol-1-yl)propyl)pyridin-4(1H)-one (1b). Diisopropylethylamine (DIPEA; 39 µL, 0.22 mmol) was added to a stirring solution of compound 9b (18 mg, 0.088 mmol) and Phenylacetylene (19 µL, 0.18 mmol) in mixture of dimethylsulfoxide (2 mL) and tetrahydrofuran (2 mL). Argon was bubbled through the solution for 15 min before and after the addition of Copper (I) iodide (CuI) (15 mg, 0.75 mmol). The reaction mixture was heated at 45° C. overnight. The reaction mixture was cooled to room temperature and was diluted with DCM (15 mL) and was sequentially washed with 4:1 mixture of NH$_4$Cl:NH$_4$OH soln. (15 mL), water (15 mL), and brine (10 mL), dried over anhydrous Na$_2$SO$_4$, filtered and concentrated in vacuo. The crude was purified by trituration with DCM-Et$_2$O (1:10) mixture to get the target compound 1b (8.7 mg, 32%) as off-white solid. $^1$H NMR (400 MHz, MeOH-d$_4$) δ 8.38 (s, 1H), 7.81 (d, J=7.4 Hz, 2H), 7.63 (d, J=7.0 Hz, 1H), 7.44 (t, J=7.5 Hz, 2H), 7.35 (t, J=7.3 Hz, 1H), 6.39 (d, J=7.0 Hz, 1H), 4.56 (t, J=6.4 Hz, 2H), 4.19-4.07 (m, 2H), 3.33-3.28 (m, 3H), 2.49-2.41 (m, 2H). $^{13}$C NMR (176 MHz, MeOD) δ 169.34, 147.82, 146.11, 137.48, 131.12, 130.27, 128.56, 128.01, 125.35, 121.04, 111.40, 50.92, 46.91, 30.41, 29.28, 10.39.

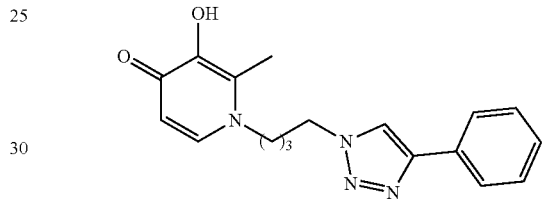

3-Hydroxy-2-methyl-1-(2-(4-phenyl-1H-1,2,3-triazol-1-yl)butyl)pyridin-4(1H)-one (1c). Phenylacetylene (25 µL, 0.22 mmol), compound 9c (25 mg, 0.11 annul) DIPEA (36 µL, 0.28 mmol), and CuI (16 mg, 0.084 mmol) was reacted in 1:1 DMSO:THF (2 mL) as described for 1b to obtain 1c as off-white solid (14 mg, 39%). $^1$H NMR (700 MHz, MeOH-d$_4$) δ 8.26 (s, 1H), 7.79 (d, J=7.6 Hz, 2H), 7.69 (dd, J=19.3, 16.0 Hz, 1H), 7.41 (t, J=7.5 Hz, 2H), 7.36-7.29 (m, 1H), 6.48 (s, 1H), 4.51-4.44 (m, 2H), 4.11 (s, 2H), 2.48-2.35 (m, 3H), 2.06-1.97 (m, 2H), 1.81 (s, 2H). $^{13}$C NMR (176 MHz, MeOH-d$_4$) δ 167.85, 154.12, 147.70, 137.52, 132.69, 130.32, 128.56, 127.96, 125.30, 120.83, 111.52, 49.26, 27.15, 26.57, 10.59.

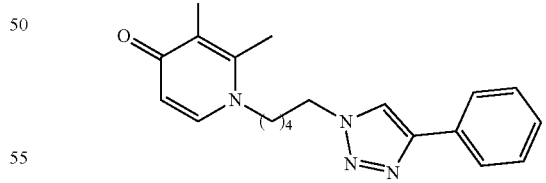

3-Hydroxy-2-methyl-1-(2-(4-phenyl-1H-1,2,3-triazol-1-yl)pentyl)pyridin-4(1H)-one (1d). Phenylacetylene (17 µL, 0.16 mmol) compound 9d (25 mg, 0.11 mmol), DIPEA (46 µL, 0.26 mmol), and CuI (15 mg, 0.080 mmol) was reacted in 1:1 DMSO:THF (2 mL) as described for 1b to obtain 1d as off-white solid (18 mg, 50%). $^1$H NMR (400 MHz, CDCl$_3$/10% MeOH-d$_4$) δ 7.79 (s, 1H), 7.72 (d, J=7.5 Hz, 2H), 7.44-7.27 (m, 5H), 6.45 (d, J=7.5 Hz, 1H), 4.36 (t, J=6.8 Hz, 2H), 3.88 (t, J=6.8 Hz, 2H), 2.34 (s, 3H), 1.99-1.85 (m, 2H), 1.74-1.70 (m, 2H), 1.36-1.31 (m, 2H). $^{13}$C NMR (176 MHz, MeOH-d$_4$) δ 162.73, 147.60, 137.52, 130.38, 128.56, 128.24, 127.94, 127.33, 125.30, 120.83, 106.36, 49.67, 48.13, 29.46, 29.19, 22.81, 12.95.

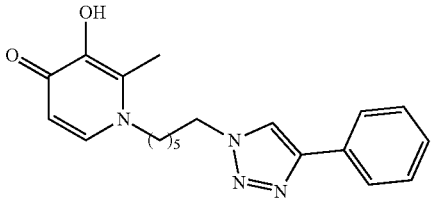

3-Hydroxy-2-methyl-1-(2-(4-phenyl-1H-1,2,3-triazol-1-yl)hexyl)pyridin-4(1H)-one (1e). Phenylacetylene (16 μL, 0.15 mmol), compound 9e (25 mg, 0.10 mmol), DIPEA (44 μL, 0.25 mmol), and CuI (14 mg, 0.075 mmol) was reacted in 1:1 DMSO:THF (2 mL) as described for 1b to obtain 1e as off-white solid (15 mg, 41%). $^1$H NMR (400 MHz, MeOH-d$_4$) δ 8.48 (s, 1H), 8.13 (d, J=6.7 Hz, 1H), 7.81 (d, J=8.3 Hz, 3H), 7.46 (t, J=7.5 Hz, 3H), 7.39 (t, J=7.2 Hz, 1H), 7.08 (d, J=6.7 Hz, 1H), 4.51 (t, J=6.8 Hz, 2H), 4.35 (t, J=7.1 Hz, 2H), 2.61 (s, 2H), 2.04-2.00 (m, 2H), 1.88-1.83 (m, 2H), 1.49-1.39 (m, 4H). $^{13}$C NMR (176 MHz, MeOH-d$_4$) δ 158.17, 146.90, 143.73, 141.89, 137.71, 129.24, 128.72, 128.49, 125.49, 121.59, 110.38, 56.40, 50.41, 29.67, 29.35, 2530, 25.20, 11.38.

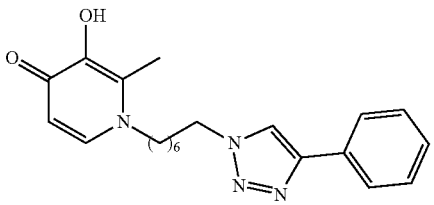

3-Hydroxy-2-methyl-1-(2-(4-phenyl-1H-1,2,3-triazol-1H-yl)heptyl)pyridin-4(1H)-one (1f). Phenylacetylene (16 μL, 0.14 mmol), compound 9f (25 mg, 0.095 mmol), DIPEA (41 μL, 0.24 mmol), and CuI (14 mg, 0.071 mmol) was reacted in 1:1 DMSO:THF (2 mL) as described for 1b to obtain 1e as off-white solid (11 mg, 32%). $^1$H NMR (700 MHz, MeOH-d$_4$) δ 8.27 (s, 1H), 7.79 (d, J=7.5 Hz, 2H), 7.42 (t, J=7.4 Hz, 2H), 7.33 (t, J=7.2 Hz, 1H), 6.68 (s, 2H), 4.44 (t, J=6.7 Hz, 2H), 4.14 (s, 2H), 2.48 (s, 2H), 1.98-1.91 (m, 2H), 1.77 (s, 2H), 1.47-1.32 (m, 6H). $^{13}$C NMR (176 MHz, MeOH-d$_4$) δ 165.05, 161.85, 147.54, 144.93, 137.50, 130.42, 128.55, 127.91, 125.28, 120.74, 110.81, 49.93, 49.02, 29.92, 29.56, 27.95, 25.76, 10.84.

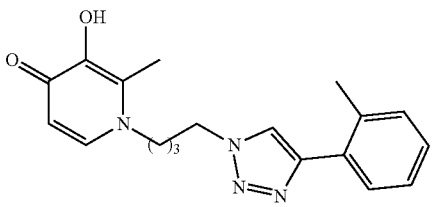

3-Hydroxy-2-methyl-1-(4-(4-(o-tolyl)-1H-1,2,3-triazol-1-yl)butyl)pyridin-4(1H)-one (2a), 2-ethynyltoluene (43 μL, 0.34 mmol), compound 9c (50 mg, 0.22 mmol), DIPEA (98 μL, 0.56 mmol), and CuI (32 mg, 0.17 mmol) was reacted in 1:1 DMSO:THF (4 mL) as described for 1b to obtain 2a as off-white solid (39 mg, 52%). $^1$H NMR (400 MHz, CDCl$_3$/10% MeOH-d$_4$) δ 7.71-7.56 (m, 2H), 7.25-7.22 (m, 1H), 7.20 (d, J=2.6 Hz, 3H), 6.32 (d, J=6.8 Hz, 1H), 4.40 (t, J=6.1 Hz, 2H), 3.89 (t, J=7.0 Hz, 2H), 2.36 (s, 3H), 2.31 (s, 3H), 1.98-1.94 (m, 2H), 1.75-1.70 (m, 2H). $^{13}$C NMR (101 MHz, CDCl$_3$) δ 169.47, 147.40, 146.27, 136.68, 135.49, 130.83, 129.64, 128.80, 128.21, 125.98, 121.80, 111.33, 52.96, 49.25, 29.54, 27.72, 26.91, 21.05, 11.62. HRMS (ESI) m/z Calcd. for C$_{19}$H$_{23}$O$_2$N$_4$ [M+H]$^+$: 339.1816, found 339.1813.

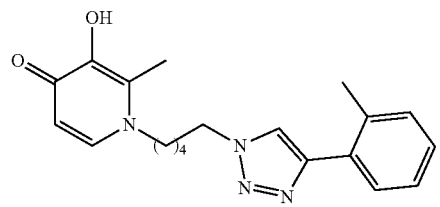

3-Hydroxy-2-methyl-1-(5-(4-(o-tolyl)-1H-1,2,3-triazol-1-yl)pentyl)pyridin-4(1H)-one (2b), 2-ethynyltoluene (40. μL, 0.32 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2b as off-white solid (41 mg, 54%). $^1$H NMR (700 MHz, DMSO-d$_6$) δ 8.34 (s, 1H), 8.22 (d, J=7.0 Hz, 1H), 7.69 (dd, J=7.1, 1.9 Hz, 1H), 7.31 (d, J=6.9 Hz, 1H), 7.29-7.23 (m, 3H), 4.41 (t, J=7.0 Hz, 2H), 4.31 (t, J=7.5 Hz, 2H), 2.52 (s, 3H), 2.42 (s, 3H), 1.96-1.90 (m, 2H), 1.78 (dt, J=15.4, 7.7 Hz, 2H), 1.31 (dt, J=15.3, 7.7 Hz, 2H). $^{13}$C NMR (176 MHz, CDCl$_3$/10% MeOH-d$_4$) δ 158.82, 146.06, 143.39, 142.15, 138.52, 135.35, 131.29, 130.62, 128.67, 128.18, 126.44, 123.63, 111.29, 56.21, 49.59, 29.51, 29.32, 23.05, 21.54, 12.95. HRMS (ESI) m/z Calcd. for C$_{20}$H$_{25}$O$_2$N$_4$ [M+H]$^+$: 353.1972, found 353.1971.

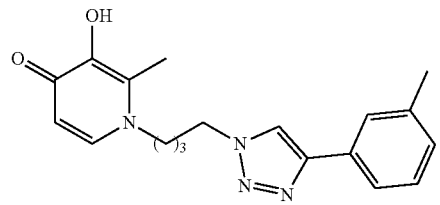

3-Hydroxy-2-methyl-1-(4-(4-(m-tolyl)-1H-1,2,3-triazol-1-yl)butyl)pyridin-4(1H)-one (2c). 3-ethynyltoluene (44 μL, 0.34 mmol), compound 9c (50 mg, 0.22 mmol), DIPEA (98 μL, 0.56 mmol), and CuI (32 mg, 0.17 mmol) was reacted in 1:1 DMSO:THF (4 mL) as described for 1b to obtain 2c as off-white solid (48 mg, 63%). $^1$H NMR (400 MHz, CDCl$_3$/10% MeOH-d$_4$) δ 7.76 (s, 1H), 7.56 (s, 1H), 7.49 (d, J=7.5 Hz, 1H), 7.28-7.19 (m, 3H), 7.10 (d, J=7.5 Hz, 1H), 6.32 (d, J=6.7 Hz, 1H), 4.38 (t, J=6.2 Hz, 2H), 3.88 (t, J=7.1 Hz, 2H), 2.33 (s, 3H), 2.31 (s, 2H), 1.99-1.93 (m, 2H), 1.74-1.69 (m, 2H). $^{13}$C NMR (101 MHz, CDCl$_3$/10% MeOH-d$_4$) δ 169.29, 148.07, 146.22, 138.51, 136.73, 130.05, 129.02, 128.69, 128.26, 126.26, 122.70, 119.91, 111.46, 53.05, 49.32, 29.52, 27.59, 26.83, 21.17, 11.59. HRMS (ESI) m/z Calcd. for C$_{19}$H$_{23}$O$_2$N$_4$ [M+H]$^+$: 339.1816, found 339.1812.

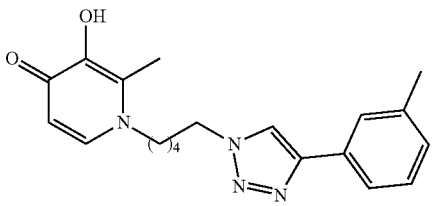

3-Hydroxy-2-methyl-1-(5-(4-(m-tolyl)-1H-1,2,3-triazol-1-yl)pentyl)pyridin-4(1H)-one (2d), 3-ethynyltoluene (55 μL, 0.42 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2d as off-white solid (32 mg, 43%). $^1$H NMR (400 MHz, CDCl$_3$) δ 7.77 (s, 1H), 7.56 (s, 1H), 7.50 (d, J=7.3 Hz, 1H), 7.34 (s, 1H), 7.23 (d, J=7.5 Hz, 1H), 7.09 (d, J=7.5 Hz, 1H), 6.46 (s, 1H), 4.35 (t, J=6.4 Hz, 2H), 3.85 (t, J=7.5 Hz, 2H), 2.32 (s, 6H), 1.95-1.89 (m, 2H), 1.73-1.66 (m, 2H), 1.35-1.31 (m, 2H). $^{13}$C NMR (176 MHz, DMSO-d$_6$) δ 167.97, 146.87, 145.63, 138.46, 138.12, 131.30, 130.41, 129.22, 128.87, 126.18, 122.79, 121.64, 110.88, 53.38, 49.77, 29.97, 29.54, 23.18, 21.51, 11.91. HRMS (ESI) m/z Calcd. for C$_{20}$H$_{25}$O$_2$N$_4$ [M+H]$^+$: 353.1972, found 353.1969.

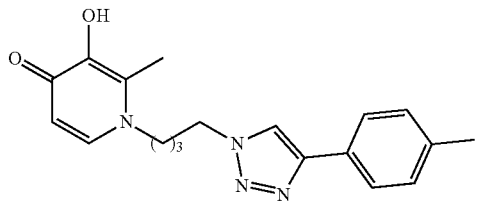

3-Hydroxy-2-methyl-1-(4-(4-(p-tolyl)-1H-1,2,3-triazol-1-yl)butyl)pyridin-4(1H)-one (2e). 4-ethynyltoluene (44 μL, 0.34 mmol), compound 9c (50 mg, 0.22 mmol), DIPEA (98 μL, 0.56 mmol), and CuI (32 mg, 0.17 mmol) was reacted in 1:1 DMSO:THF (4 mL) as described for 1b to obtain 2e as off-white solid (46 mg, 60%). $^1$H NMR (400 MHz, CDCl$_3$) δ 7.73 (s, 1H), 7.60 (d, J=8.0 Hz, 2H), 7.25-7.19 (m, 1H), 7.17 (d, J=7.8 Hz, 2H), 6.32 (d, J=7.1 Hz, 1H), 4.38 (t, J=6.5 Hz, 2H), 3.88 (t, J=7.4 Hz, 2H), 2.31 (s, 6H), 1.97-1.92 (m, 2H), 1.76-1.71 (m, 2H). $^{13}$C NMR (101 MHz, CDCl$_3$) δ 169.38, 148.04, 146.20, 138.13, 136.72, 129.44, 128.73, 127.44, 125.53, 119.52, 111.33, 52.97, 49.29, 29.51, 27.61, 26.82, 20.99, 11.55. HRMS (ESI) m/z Calcd. for C$_{19}$H$_{23}$O$_2$N$_4$ [M+H]$^+$: 339.1816, found 339.1813.

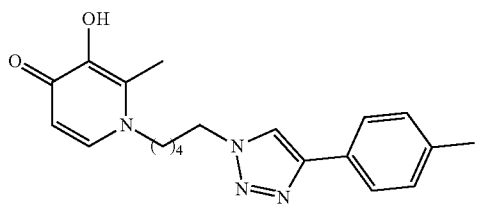

3-Hydroxy-2-methyl-1-(4 (4-(p-tolyl)-1H-1,2,3-triazol-1-yl)pentyl/pyridin-4(1H)-one (2f). 4-ethynyltoluene (55 μL, 0.42 mmol), compound 94 (50 mg, 0.21 mmol), DIPEA (92 μL, 0.53 mmol), and CuI (30 mg, 0.16 mmol) was reacted in 1:1 DMSO:THF (4 mL) as described for 1b to obtain 2f as off-white solid (48 mg, 65%). $^1$H NMR (400 MHz, CDCl$_3$/10% MeOH-d$_4$) δ 7.82 (s, 1H), 7.68 (d, J=7.8 Hz, 2H), 7.3 (s, 1H), 7.25 (d, J=7.6 Hz, 2H), 6.39 (d, 1H), 4.43 (t, J=6.4 Hz, 2H), 3.91 (t, J=7.4 Hz, 2H), 2.38 (s, 6H), 2.05-1.92 (m, 2H), 1.82-1.74 (m, 2H), 1.42-1.35 (m, 2H). $^{13}$C NMR (101 MHz, CDCl$_3$) δ 169.41, 147.94, 146.07, 138.06, 136.81, 129.44, 127.55, 125.52, 119.36, 111.39, 53.52, 49.72, 30.13, 29.55, 23.24, 21.04, 11.55. HRMS (ESI) m/z Calcd. for C$_{20}$H$_{25}$O$_2$N$_4$ [M+H]$^+$: 3511972, found 353.1970.

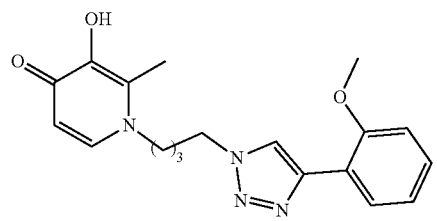

3-Hydroxy-1-(4-(4-(2-methoxyphenyl)-1H-1,2,3-triazol-1-yl)butyl)-2-methylpyridin-4(1H)-one (2g). 2-ethynylanisole (58 μL, 0.45 mmol), compound 9c (50 mg, 0.22 mmol), DIPEA (98 μL, 0.56 mmol), and CuI (32 mg, 0.17 mmol) was reacted in 1:1 DMSO:THF (4 mL) as described for 1b to obtain 2g as off-white solid (67 mg, 84%). $^1$H NMR (700 MHz, DMSO-d$_6$) δ 8.34 (s, 1H), 8.11 (dd, J=7.6, 1.6 Hz, 1H), 7.57 (d, J=6.7 Hz, 1H), 7.33-7.27 (m, 1H), 7.10 (d, J=8.2 Hz, 1H), 7.03 (t, J=7.4 Hz, 1H), 6.15 (d, J=6.7 Hz, 1H), 4.44 (t, J=6.9 Hz, 2H), 3.97 (t, J=7.2 Hz, 2H), 3.89 (s, 3H), 2.27 (s, 3H), 1.93-1.83 (m, 2H), 1.73-1.59 (m, 2H). $^{13}$C NMR (176 MHz, DMSO-d$_6$) δ 168.86, 155.88, 145.87, 142.26, 138.11, 129.32, 127.11, 124.30, 121.11, 119.76, 112.09, 111.00, 55.98, 52.79, 49.20, 27.68, 27.19, 11.84. HRMS (ESI) m/z Calcd. for C$_{19}$H$_{23}$O$_3$N$_4$ [M+H]$^+$: 355.1765, found 355.1762.

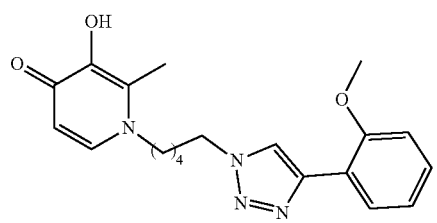

3-Hydroxy-1-(5-(4-(2-methoxyphenyl)-1H-1,2,3-triazol-1-yl)pentyl)-2-methylpyridin-4(1H)-one (2h), 2-ethynylanisole (55 μL, 0.42 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2h as off-white solid (40 mg, 51%). $^1$H NMR (400 MHz, CDCl$_3$/10% MeOH-d$_4$) δ 8.16 (d, J=7.7, 1H), 7.29-7.24 (m, 3H), 7.21 (d, J=6.8 Hz, 1H), 7.04-6.97 (m, 1H), 6.93 (d, J=8.3 Hz, 1H), 6.31 (d, J=7.1 Hz, 1H), 4.36 (t, J=6.8 Hz, 2H), 3.87 (s, 3H), 3.82 (t, J=7.6 Hz, 2H), 2.31 (s, 3H), 1.99-1.89 (m, 2H), 1.70 (dt, J=15.5, 7.9 Hz, 2H), 1.39-1.26 (m, 2H). $^{13}$C NMR (101 MHz, CDCl$_3$/10% MeOH-d$_4$) δ 169.14, 155.56, 146.07, 143.19, 136.75, 129.51, 129.14, 127.25, 123.18, 120.95, 118.77, 111.45, 110.81, 55.26, 53.75, 49.63, 30.14, 29.64, 29.57, 23.18, 11.67. HRMS (ESI) m/z Calcd. for C$_{20}$H$_{25}$O$_3$N$_4$ [M+H]$^+$: 369.1921, found 369.1918.

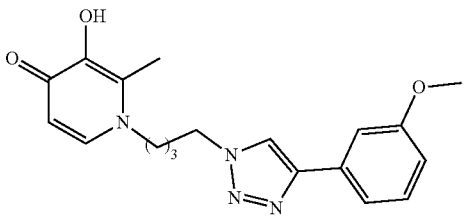

3-Hydroxy 1-(4-(4-(3-methoxyphenyl)-1H-1,2,3-triazol-1-yl)butyl)-2-methylpyridin-4(1H)-one (2i). 3-ethynylanisole (57 μL, 0.45 mmol), compound 9c (50 mg, 0.22 mmol), DIPEA (98 μL, 0.56 mmol), and CuI (32 mg, 0.17 mmol) was reacted in 1:1 DMSO:THF (4 mL) as described for 1b to obtain 2i as off-white solid (55 mg, 69%). $^1$H NMR (400 MHz, MeOH-d$_4$) δ 8.19-8.13 (m, 1H), 7.12 (t, J=5.7 Hz, 1H), 4.45-4.34 (m, 2H), 3.34 (dd, J=8.6, 4.8 Hz, 2H), 2.64 (d, J=3.8 Hz, 3H), 1.88 (dt, J=15.7, 7.8 Hz, 2H), 1.66 (dt, J=14.8, 6.9 Hz, 2H), 1.48 (ddd, J=15.6, 9.1, 6.0 Hz, 2H). $^{13}$C NMR (101 MHz, CDCl$_3$) δ 169.28, 160.07, 147.82, 146.31, 136.69, 131.51, 129.84, 129.01, 120.13, 118.07, 114.15, 111.37, 111.07, 55.24, 53.01, 49.34, 29.50, 27.61, 26.82, 11.56. HRMS (ESI) m/z Calcd. for $C_{19}H_{23}O_3N_4$ [M+H]$^+$: 355.1765, found 355.1765.

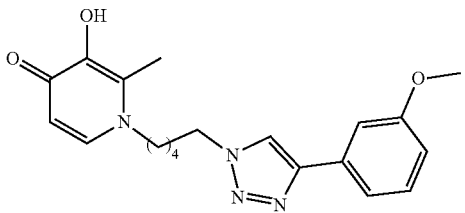

3-Hydroxy-1-(5-(4-(3-methoxyphenyl)-1H-1,2,3-triazol-1-yl)pentyl)-2-methylpyridin-4(1H)-one (2j). 3-ethynylanisole (54 μL, 0.42 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2j as off-white solid (50 mg, 64%). $^1$H NMR (400 MHz, CDCl$_3$) δ 7.73 (s, 1H), 7.45 (s, 1H), 7.39-7.31 (m, 2H), 7.18 (t, J=8.4 Hz, 1H), 6.93-6.84 (m, 1H), 6.36 (d, J=7.1 Hz, 1H), 4.42 (t, J=6.6 Hz, 2H), 3.87 (s, 3H), 3.83 (t, J=6.6 Hz, 2H), 2.37 (s, 3H), 2.06-1.94 (m, 2H), 1.80-1.74 (m, 2H), 1.45-1.38 (m, 2H). $^{13}$C NMR (101 MHz, CDCl$_3$) δ 168.45, 159.93, 147.65, 131.45, 129.92, 120.24, 117.99, 114.09, 110.80, 55.25, 53.80, 49.85, 29.63, 23.20, 11.77. HRMS (ESI) m/z Calcd. for $C_{20}H_{25}O_3N_4$ [M+H]$^+$: 369.1921, found 369.1918.

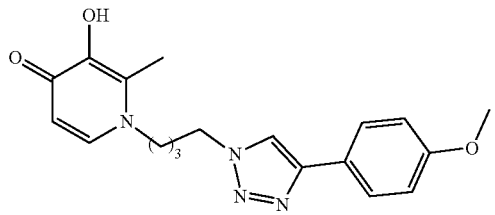

3-Hydroxy-1-(4-(4-(4-methoxyphenyl)-1H-1,2,3-triazol-1-yl)butyl)-2-methylpyridin-4(1H)-one (2k). 4-ethynylanisole (58 μL, 0.45 mmol), compound 9c (50 mg, 0.22 mmol), DIPEA (98 μL, 0.56 mmol), and CuI (32 mg, 0.17 mmol) was reacted in 1:1 DMSO:THF (4 mL) as described for 1b to obtain 2k as off-white solid (43 mg, 54%). $^1$H NMR (400 MHz, CDCl$_3$) δ 7.68 (d, J=16.0 Hz, 1H), 7.63 (d, J=8.0 Hz, 2H), 7.25-7.16 (m, 1H), 6.89 (d, J=7.9 Hz, 2H), 6.31 (d, J=7.9 Hz, 1H), 4.36 (t, J=6.9 Hz, 2H), 3.88 (t, J=6.3 Hz, 2H), 3.77 (s, 3H), 2.30 (s, 3H), 1.96-1.90 (m, 2H), 1.77-1.68 (m, 2H). $^{13}$C NMR (101 MHz, CDCl$_3$) δ 169.44, 159.64, 147.77, 146.18, 136.86, 129.84, 126.90, 122.72, 119.33, 114.25, 111.94, 77.45, 77.13, 76.82, 55.24, 53.17, 49.33, 29.59, 27.65, 26.86, 11.71. HRMS (ESI) m/z Calcd. for $C_{19}H_{23}O_3N_4$ [M+H]$^+$: 355.1765, found 355.1762.

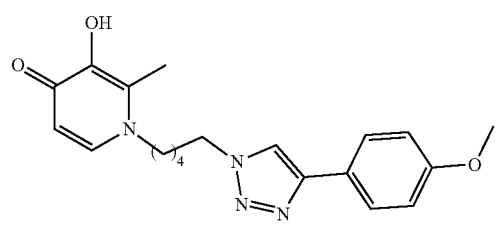

3-Hydroxy-1-(5-(4-(4-methoxyphenyl)-1H-1,2,3-triazol-1-yl)pentyl)-2-methylpyridin-4(1H)-one (2l). 4-ethynylanisole (55 μL, 0.42 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2l as off-white solid (37 mg, 47%). $^1$H NMR (700 MHz, DMSO-d$_6$) δ 8.39 (s, 1H), 7.74 (t, J=17.6 Hz, 2H), 7.50 (d, J=7.2 Hz, 1H), 6.99 (d, J=8.5 Hz, 2H), 6.06 (d, J=7.2 Hz, 1H), 4.36 (t, J=6.9 Hz, 2H), 3.89 (t, J=7.5 Hz, 2H), 3.77 (s, 3H), 2.26 (s, 3H), 1.92-1.84 (m, 2H), 1.66 (dt, J=15.1, 7.7 Hz, 2H), 1.33-1.24 (m, 2H). $^{13}$C NMR (176 MHz, DMSO) δ 169.34, 15947, 146.71, 137.88, 128.67, 126.95, 124.02, 120.75, 114.80, 110.72, 55.65, 53.01, 49.73, 30.07, 29.58, 23.21, 11.77. HRMS (ESI) m/z Calcd. for $C_{20}H_{25}O_3N_4$ [M+H]$^+$: 369.1921, found 369.1918.

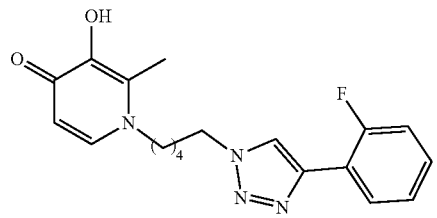

1-(5-(4-(2-Fluorophenyl)-1H-1,2,3-triazol-1-yl)pentyl)-3-hydroxy-2-methylpyridin-4(1H)-one (2m), 1-ethynyl-2-fluorobenzene (48 μL, 0.42 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2m as off-white solid (39 mg, 51%). $^1$H NMR (400 MHz, MeOH-d$_4$) δ 8.19-8.13 (m, 1H), 7.12 (t, J=5.7 Hz, 1H), 4.45-4.34 (m, 2H), 3.34 (dd, J=8.6, 4.8 Hz, 2H), 2.64 (d, J=3.8 Hz, 3H), 1.88 (dt, J=15.7, 7.8 Hz, 2H), 1.66 (dt, J=14.8, 6.9 Hz, 2H), 1.45 (ddd, J=15.6, 9.1, 6.0 Hz, 2H). $^{13}$C NMR (101 MHz, CDCl$_3$) δ 169.16, 160.36, 157.89, 146.08, 141.28, 136.75, 129.49, 127.48, 124.64, 122.90, 117.97, 115.77, 111.47, 53.74, 49.80, 30.13, 29.60, 23.18, 11.68. HRMS (ESI) m/z Calcd. for $C_{19}H_{22}O_2N_4F$ [M+H]$^+$: 357.1721, found 357.1718.

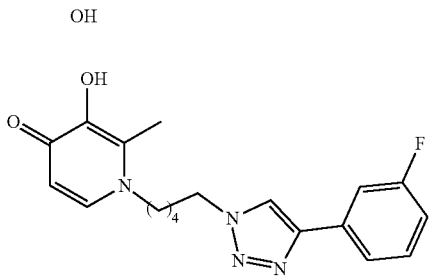

1-(5-(4-(3-Fluorophenyl)-1H-1,2,3-triazol-1-yl)pentyl)-3-hydroxy-2-methylpyridin-4(1H)-one (2n). 1-ethynyl-2-fluorobenzene (38 μL, 0.32 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2n as off-white solid (48 mg, 64%). $^1$H NMR (700 MHz, DMSO-$d_6$) δ 8.61 (d J=15.2 Hz, 1H), 7.66 (t, J=9.4 Hz, 1H), 7.64-7.54 (m, 2H), 7.48 (dt, J=14.2, 7.1 Hz, 1H), 7.13 (td, J=8.5, 2.4 Hz, 1H), 6.19 (d, J=6.9 Hz, 1H), 4.39 (t, J=7.0 Hz, 2H), 3.93 (1, J=7.6 Hz, 2H), 2.29 (s, 3H), 1.95-1.84 (m, 2H), 1.72-1.60 (m, 2H), 1.34-1.25 (m, 2H). $^{13}$C NMR (176 MHz, DMSO-$d_6$) δ 168.03, 163.77, 162.39, 145.69, 138.11, 133.77, 133.73, 131.48, 131.43, 130.24, 122.42, 121.63, 114.96, 114.84, 112.20, 112.07, 110.86, 53.34, 49.88, 29.96, 29.51, 23.16, 11.90. HRMS (ESI) m/z Calcd. for $C_{19}H_{22}O_2N_4F$ [M+H]$^+$: 357.1721, found 357.1718.

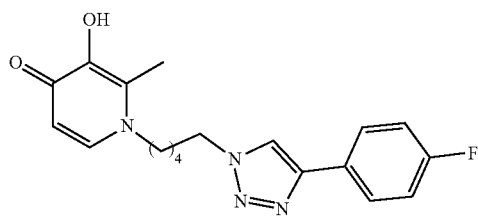

1-(5-(4-(4-Fluorophenyl)-1H-1,2,3-triazol-1-yl)pentyl)-3-hydroxy-2-methylpyridin-4(1H)-one (2o). 1-ethynyl-2-fluorobenzene (36 μL, 0.32 mmol), compound 9d (50 mg, 0.21 mmol), DIPEA (92 μL, 0.53 mmol), and CuI (30 mg, 0.16 mmol) was reacted in 1:1 DMSO-THF (4 mL) as described for 1b to obtain 2o as off-white solid (60 mg, 80%). $^1$H NMR (400 MHz, CDCl$_3$) δ 7.74 (s, 1H), 7.73 (d, J=9.4 Hz, 1H), 7.71-7.67 (m, 2H), 7.72-7.64 (m, 2H), 7.22 (d, J=7.2 Hz, 1H), 7.04 (t, J=8.7 Hz, 2H), 6.31 (d, J=7.2 Hz, 1H), 4.34 (t, J=6.9 Hz, 2H), 3.85-3.78 (m, 2H), 2.30 (s, 3H), 1.97-1.87 (m, 2H), 1.70 (dt, J=15.5, 7.8 Hz, 2H), 1.31 (dq, J=15.7, 7.9 Hz, 2H). $^{13}$C NMR (1.01 MHz, CDCl$_3$) δ 169.14, 163.78, 161.32, 146.82, 145.99, 136.78, 129.19, 127.37, 127.29, 126.67, 126.64, 119.71, 115.73, 115.52, 111.26, 53.53, 49.74, 29.96, 29.45, 23.14, 11.52. HRMS (ESI) m/z Calcd. for $C_{19}H_{22}O_2N_4F$ [M+H]$^+$: 357.1721, found 357.1718.

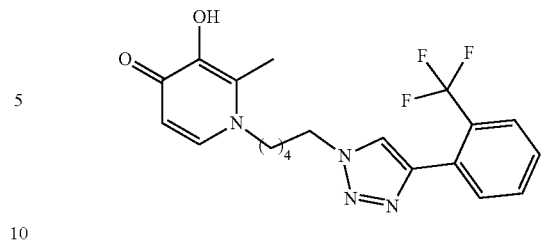

3-Hydroxy-2-methyl-1-(5-(4-(2-(trifluoromethyl)phenyl)-1H-1,2,3-triazol-1-yl)pentyl)pyridin-4(1H)-one (2p). 2-ethynyl-α,α,α-trifluorotoluene (44 μL, 0.32 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2p as off-white solid (70 mg, 82%). $^1$H NMR (700 MHz, DMSO-$d_6$) δ 8.27 (s, 1H), 7.89 (t, J=12.8 Hz, 1H), 7.83 (d, J=7.8 Hz, 1H), 7.78-7.70 (m, 2H), 7.61 (ddd, J=9.1, 6.4, 3.8 Hz, 1H), 6.73 (d, J=6.5 Hz, 1H), 4.44 (t, J=7.0 Hz, 2H), 4.16-4.08 (m, 2H), 2.41 (s, 3H), 1.95-1.85 (m, 2H), 1.73 (dt, J=15.3, 7.7 Hz, 2H), 1.29 (dt, J=15.3, 7.7 Hz, 2H). $^{13}$C NMR (176 MHz, DMSO-$d_6$) δ 163.42, 144.54, 143.70, 143.69, 13831, 136.23, 133.04, 132.24, 130.21, 130.20, 129.21, 129.20, 127.18, 127.01, 126.84, 126.74, 126.71, 126.68, 126.65, 125.28, 124.37, 124.35, 124.33, 124.31, 123.73, 122.17, 111.05, 54.79, 49.67, 29.59, 23.01, 12.39. HRMS (ESI) m/z Calcd. for $C_{20}H_{22}O_2N_4F_3$ [M+H]$^+$: 407.1689, found 407.1684.

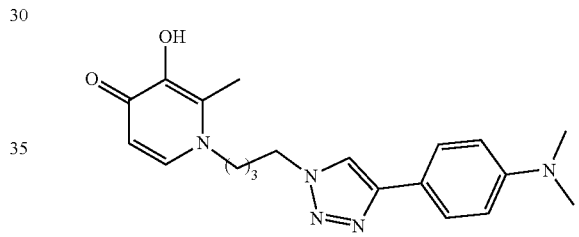

1-(4-(4-(4-(Dimethylamino)phenyl)-1H-1,2,3-triazol-1-yl)butyl)-3-hydroxy 2-methylpyridin-4(1H)-one (2q). 4-ethynyl-N,N-dimethylaniline (49 mg, 0.34 mmol), compound 9c (50 mg, 0.22 mmol), DIPEA (98 μL, 0.56 mmol), and CuI (32 mug, 0.17 mmol) was reacted in 1:1 DMSO:THF (4 mL) as described for 1b to obtain 2q as off-white solid (36 mg, 43%). $^1$H NMR (400 MHz, CDCl$_3$110% MeOH-$d_4$) δ 7.71 (s, 1H), 7.66 (d, J=8.4 Hz, 2H), 7.31 (d, J=6.7 Hz, 1H), 6.79 (d, J=8.3 Hz, 2H), 6.40 (d, J=6.8 Hz, 1H), 4.35 (t, J=6.9 Hz, 2H), 3.86 (t, J=7.4 Hz, 2H), 3.00 (s, 6H), 2.41 (s, 3H), 2.03-1.99 (m, 2H), 1.81-1.76 (m, 2H), 1.42-1.38 (m, 2H). $^{13}$C NMR (176 MHz, DMSO-$d_6$) δ 163.54, 150.50, 147.46, 144.60, 138.34, 136.25, 126.56, 119.95, 119.38, 112.92, 111.18, 54.39, 49.26, 40.52, 27.37, 26.94, 12.44. HRMS (ESI) m/z Calcd. for $C_{20}H_{26}O_2N_5$ [M+H]$^+$: 368.2081, found 368.2079.

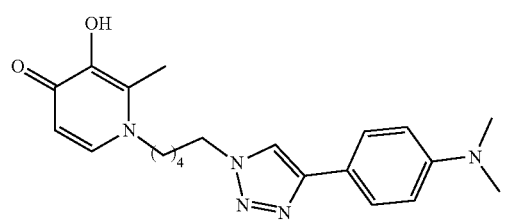

1-(5-(4-(4 (Dimethylamino)phenyl)-1H-1,2,3-triazol-1-yl)pentyl)-3-hydroxy-2-methylpyridin-4(1H)-one (2r). 4-ethynyl-N,N-dimethylaniline (34 mg, 0.23 mmol), compound 9d (50 mg, 0.21 mmol) DIPEA (92 μL, 0.53 mmol), and CuI (30 mg, 0.16 mmol) was reacted in 1:1 DMSO:THF (4 mL) as described for 1b to obtain 2r as off-white solid (44 mg, 54%). $^1$H NMR (400 MHz, MeOH-d$_4$) δ 8.19-8.13 (m, 1H), 7.12 (t, J=5.7 Hz, 1H), 4.45-4.34 (m, 2H), 3.34 (dd, J=8.6, 4.8 Hz, 2H), 2.64 (d, J=3.8 Hz, 3H), 1.88 (dt, J=15.7, 7.8 Hz, 2H), 1.66 (dt, J=14.8, 6.9 Hz, 2H), 1.48 (ddd, J=15.6, 9.1, 6.0 Hz, 2H). $^{13}$C NMR (176 MHz, DMSO-d$_6$) δ 158.95, 145.54, 143.46, 142.04, 138.50, 127.61, 127.39, 126.64, 125.02, 121.58, 121.25, 111.29, 56.17, 49.74, 49.64, 43.73, 29.47, 29.34, 23.06, 12.94. HRMS (ESI) m/z Calcd. for C$_{21}$H$_{28}$O$_2$N$_5$ [M+H]$^+$: 382.2238, found 382.2234.

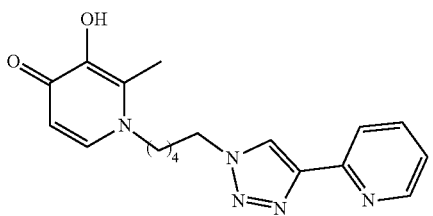

3-Hydroxy-2-methyl-1-(5-(4-(pyridin-2-yl)-1H-1,2,3 triazol-1-yl)pentyl)pyridin-4(1H-one (2s). 2-ethynylpyridine (32 μL, 0.32 mmol), compound 9d (50 mg, 0.21 mmol), DIPEA (92 μL, 0.53 mmol), and CuI (30 mg, 0.16 mmol) was reacted in 1:1 DMSO:THF (4 mL) as described for 1b to obtain 2s as brown solid (47 mg, 65%). $^1$H NMR (400 MHz, MeOH-d$_4$) δ 8.19, 8.13 (m, 1H), 7.12 (t, J=5.7 Hz, 1H), 4.45-4.34 (m, 2H), 3.34 (dd, J=8.6, 4.8 Hz, 2H), 2.64 (d, J=3.8 Hz, 3H), 1.88 (dt, J=15.7, 7.8 Hz, 2H), 1.66 (dt, J=14.8, 6.9 Hz, 2H), 1.48 (ddd, J=15.6, 9.1, 6.0 Hz, 2H). $^{13}$C NMR (101 MHz, CDCl$_3$) δ 166.92, 149.90, 148.85, 147.94, 145.76, 137.31, 136.80, 131.17, 122.89, 122.36, 120.38, 111.47, 77.15, 54.18, 49.85, 30.02, 29.47, 23.25, 12.01. HRMS (ESI) m/z Calcd. for 18$_1$H$_{22}$O$_2$N$_5$ [M+H]$^+$: 340.1768, found 340.1765.

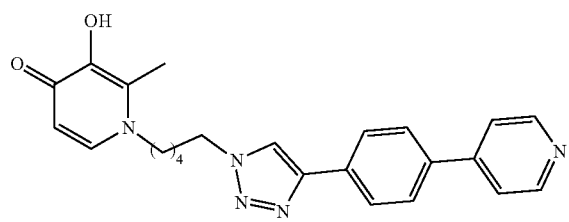

3-Hydroxy-2-methyl-1-(5-(4-(4-(pyridin-4-yl)phenyl)-1H-1,2,3-triazol-1-yl)pentyl)pyridin-4(1H)-one (2t). 4-(4ethynylphenyl)pyridine (32 mg, 0.18 mmol) compound 9d (35 mg, 0.15 mmol), DIPEA (65 μL, 0.37 mmol), and CuI (21 mg, 0.11 mmol) was reacted in 1:1 DMSO:THF (4 mL) as described for 1b to obtain 2t as off-white solid (28 mg, 45%). $^1$H NMR (400 MHz, CDCl$_3$/10% MeOH-d$_4$) δ 8.52 (dd, J=4.6, 1.5 Hz, 2H), 7.86 (d, J=8.1 Hz, 3H), 7.67 (d, J=8.3 Hz, 2H), 7.52 (dd, J=4.6, 1.6 Hz, 2H), 7.23 (d, J=7.3 Hz, 1H), 6.31 (d, J=7.2 Hz, 1H), 4.38 (t, J=6.8 Hz, 2H), 3.84 (t, J=7.5 Hz, 2H), 2.33 (d, J=6.6 Hz, 3H), 1.94 (dt, J=14.7, 7.4 Hz, 2H), 1.72 (dt, J=15.6, 7.9 Hz, 2H), 1.43-1.27 (m, 2H). $^{13}$C NMR (101 MHz, CDCl$_3$) δ 169.35, 149.77, 148.00, 147.08, 146.17, 137.52, 136.71, 131.25, 128.83, 127.39, 126.29, 121.44, 120.11, 111.34, 53.56, 49.84, 30.06, 29.55, 23.23, 11.60. HRMS (ESI) m/z Calcd. for C$_{24}$H$_{26}$O$_2$N$_5$ [M+H]$^+$: 416.2081, found 416.2074.

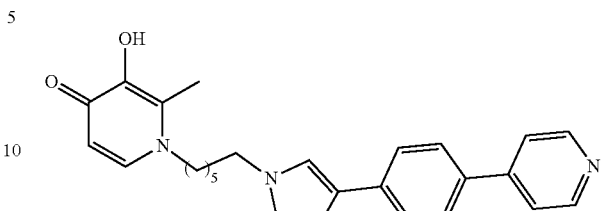

3-Hydroxy-2-methyl-1-(6-(4-(4-(pyridin-4-yl)hexyl)-1H-1,2,3-triazol-1-yl)hexyl)pyridin-4(1H)-one (2u). 4-(4ethynylphenyl)pyridine (22 mg, 0.12 mmol), compound 9e (30 mg, 0.12 mmol), DIPEA (52 μL, 0.30 mmol), and CuI (17 mg, 0.090 mmol) was reacted in 1:1 DMSO:THF (4 mL) as described for 1b to obtain 2u as off-white solid (26 mg, 51%). $^1$H NMR (700 MHz, DMSO-d$_6$) δ 8.93 (s, 2H), 8.76 (d, J=7.0 Hz, 1H), 8.37 (d, J=5.3 Hz, 2H), 8.23 (d, J=7.0 Hz, 1H), 8.13-8.03 (m, 4H), 7.33 (t, J=7.5 Hz, 1H), 4.41 (t, J=7.0 Hz, 2H), 4.30 (dd, J=19.0, 11.4 Hz, 2H), 2.52 (d, J=6.7 Hz, 3H), 1.89 (dt, J=13.8, 7.0 Hz, 2H), 1.73 (dt, J=15.0, 7.6 Hz, 2H), 1.37-1.31 (m, 4H). $^{13}$C NMR (176 MHz, DMSO-d$_6$) δ 158.99, 154.46, 145.71, 143.37, 141.98, 138.49, 134.34, 134.02, 129.06, 126.48, 123.82, 122.90, 111.31, 56.30, 50.02, 29.76, 25.82, 25.44, 12.95. HRMS (ESI) m/z Calcd. for C$_{25}$H$_{28}$O$_2$N$_5$ [M+H]$^+$: 4301238, found 430.2230.

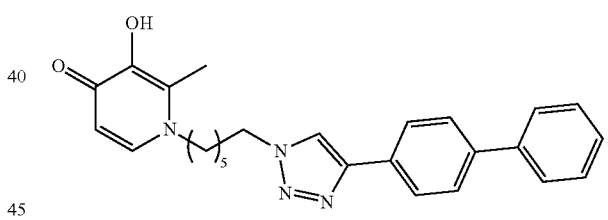

1-(6-(4-([1,1'-Biphenyl]-4-yl)-1H-1,2,3-triazol-1-yl)hexyl)-3-hydroxy-2-methylpyridin-4(1H)-one (2v). 4-ethynyl-1,1'-biphenyl (26 mg, 0.15 mmol), compound 9e (35 mg, 0.14 mmol), DIPEA (45 μL, 0.35 mmol), and CuI (20 mg, 0.10 mmol) was reacted in 1:1 DMSO:THF (4 mL) as described for 1b to obtain 2v as off-white solid (43 mg, 71%). $^1$H NMR (700 MHz, DMSO-d$_6$) δ 8.59 (s, 1H), 7.91 (t, J=8.1 Hz, 3H), 7.71 (dd, J=30.1, 8.0 Hz, 4H), 7.46 (t, J=7.5 Hz, 2H), 7.35 (dd, J=10.7, 4.0 Hz, 1H), 6.78 (t, J=14.1 Hz, 1H), 4.39 (dd, J=15.5, 8.5 Hz, 2H), 4.13 (dd, J=25.4, 18.1 Hz, 2H), 2.38 (d, J=33.9 Hz, 3H), 1.88 (dd, J=10.7, 3.8 Hz, 2H), 1.73-1.64 (m, 2H), 1.38-1.29 (m, 4H). $^{13}$C NMR (176 MHz, DMSO-d$_6$) δ 163.31, 146.44, 144.50, 140.10, 139.88, 138.31, 136.40, 130.50, 129.41, 127.97, 127.56, 126.96, 126.14, 121.78, 111.08, 54.96, 49.92, 30.07, 29.82, 25.86, 25.52, 12.45. HRMS (ESI) m/z Calcd. for C$_{26}$H$_{29}$O$_2$N$_4$ [M+H]$^+$: 429.2285, found 429.2277.

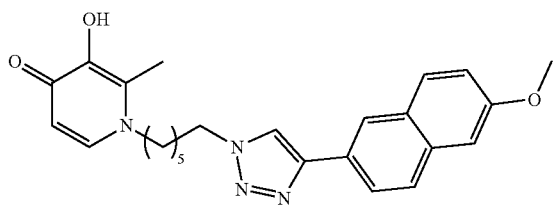

3-Hydroxy-1-(6-(4-(6-methoxynaphthalen-2-yl)-1H-1,2,3-triazol-1-yl)hexyl)-2-methylpyridin-4(1H)-one (2w). 2-ethynyl-6-methoxynaphthalene (27 mg, 0.15 mmol), compound 9e (35 mg. 0.14 mmol), DIPEA (45 μL, 0.35 mmol), and CuI (20 mg, 0.11 mmol) was reacted in 1:1 DMSO:THF (4 mL) as described for 1b to obtain 2w as off-white solid (32 mg, 53%). $^1$H NMR (700 MHz, DMSO-$d_6$) 8.58 (s, 1H), 8.28 (s, 1H), 7.91 (d, J=8.4 Hz, 1H), 7.85 (dd, J=8.5, 5.9 Hz, 2H), 7.55 (dd, J=23.4, 8.2 Hz, 1H), 7.30 (dd, J=19.9, 5.5 Hz, 1H), 7.17 (dd, J=8.9, 2.5 Hz, 1H), 6.12 (dd, J=22.5, 7.2 Hz, 1H), 4.39 (t, J=7.0 Hz, 2H), 3.91-3.88 (m, 2H), 3.87 (s, 3H), 2.27 (d, J=7.7 Hz, 3H), 1.95-1.82 (m, 2H), 1.68-1.55 (m, 2H), 1.36-1.25 (m, 4H), $^{13}$C NMR (176 MHz, DMSO-$d_6$) δ 168.99, 157.94, 147.00, 145.86, 138.05, 134.34, 129.94, 129.06, 127.78, 126.66, 124.62, 123.84, 121.55, 119.52, 110.82, 106.65, 55.73, 53.20, 49.93, 30.45, 29.87, 25.92, 25.61, 11.80. HRMS (ESI) m/z Calcd. for $C_{25}H_{29}O_3N_4$ $[M+H]^+$: 433.2234, found 433.2226.

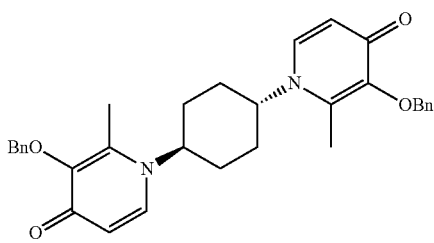

1,1'-((1r, 4r)-Cyclohexane-1,4-diyl)bis(3-(benzyloxy)-2-methylpyridin-4(1H)-one) (16). 3-Benzyloxy-2-methyl-4 pyrone 7 (139 mg, 0.64 mmol), trans-1,4-diaminocyclohexane 23 (38 mg, 0.32 mmol), and sodium hydroxide (6.40 mg, 0.16 mmol) in methanol-$H_2O$ (2:1, 3 mL) mixture was heated in a sealed tube at 105° C. for 72 h. The mixture was then cooled to room temperature and the product was extracted with DCM (50 mL) and then the organic layer was washed with water (2×10 mL) and brine (10 mL), dried over anhydrous $Na_2SO_4$, filtered and concentrated in vacuo. The crude was purified by preparative chromatography (eluent 15% MeOH in $CHCl_3$ containing 1% $Et_3N$) to give the title compound 16 (24 mg, 14%) as white solid after purification by preparative chromatography (eluent 10% MeOH in DCM containing 0.5% $NH_4OH$ soln.). $^1$H NMR (400 MHz, $CDCl_3$) δ 7.37 (dq, J=6.7, 2.5 Hz, 2H), 7.35-7.26 (m, 4H), 6.45 (dd, J=7.7, 2.1 Hz, 1H), 5.18 (d, J=2.2 Hz, 2H), 3.97 (s, 1H), 2.14 (s, 3H), 2.06 (d, J=8.2 Hz, 2H), 1.91-1.76 (m, 2H). HRMS (ESI) m/z Calcd. for $C_{32}H_{35}O_4N_2$ $[M+H]^+$: 511.2591, found 511.2579.

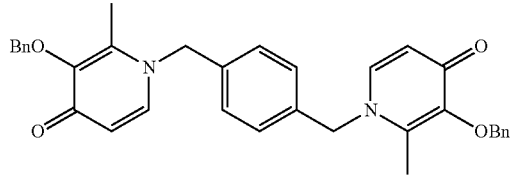 [SMILES: Cc1c(OCc2ccccc2)c(=O)ccn1Cc1ccc(Cn2ccc(=O)c(OCc3ccccc3)c2C)cc1]

1,1'-(1,4-Phenylenebis(methylene))bis(3-(benzyloxy)-2-methylpyridin-4(1H)-one) (17). 3-Benzyloxy-2-methyl-4 pyrone 7 (115 mg, 0.53 mmol) p-xylenediamine 24 (24 mg, 0.18 mmol) and sodium hydroxide (3.6 mg, 0.09 mmol) in methanol-$H_2O$ (2:1, 3 mL) mixture were subjected to the same reaction condition as described for the synthesis of 16, afforded 17 (29 mg, 30%) as white solid after purification by preparative chromatography (eluent 10% MeOH in DCM containing 0.5% $NH_4OH$ soln.). $^1$H NMR (400 MHz, $CDCl_3$) δ 7.37 (dd, J=7.5, 2.0 Hz, 2H), 7.30-7.17 (m, 4H), 6.83 (d, J=1.1 Hz, 2H), 6.51-6.42 (m, 1H), 5.25 (s, 2H), 4.93 (s, 2H), 1.94 (s, 3H). HRMS (ESI) m/z Calcd. for $C_{34}H_{33}O_4N_2$ $[M+H]^+$: 533.2435, found 533.2422.

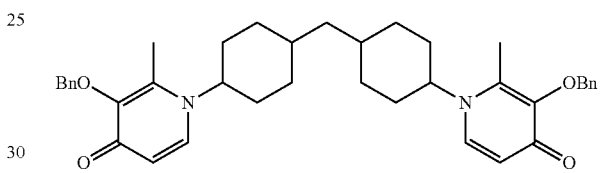

1,1'-(Methylenebis(cyclohexane-4,1-diyl))bis(3-(benzyloxy)-2-methylpyridin-4(1H)-one) (18). 3-Benzyloxy-2-methyl-4-pyrone 7 (106 mg, 0.49 mmol), 4,4'-methylenebis(cyclohexylamine) 25 (109 mg, 0.49 mmol), and sodium hydroxide (20 mg, 0.49 mmol) in methanol-$H_2O$ (2:1.3 mL) mixture were subjected to the same reaction condition as described for the synthesis of 16, afforded 18 (37 mg, 12%) as white solid after purification by preparative chromatography (eluent 10% MeOH in DCM containing 0.5% $NH_4OH$ soln.). $^1$H NMR (400 MHz, $CDCl_3$) δ 7.43-7.36 (m, 2H), 7.36-7.26 (m, 4H), 6.44 (dd, J=7.8, 5.4 Hz, 1H), 5.20 (s, 2H), 3.81 (s, 1H), 2.11 (s, 3H), 1.89 (d, J=11.9 Hz, 3H), 1.81-1.50 (m, 7H). HRMS (ESI) m/z Calcd. for $C_{39}H_{47}O_4N_2$ $[M+H]^+$: 607.3530, found 607.3519.

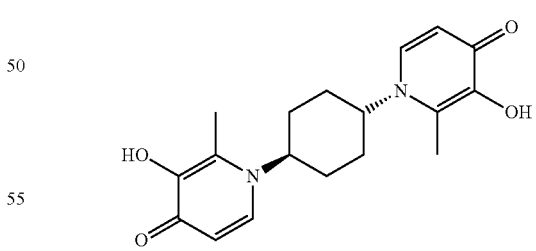

1,1'-((1r, 4r)-Cyclohexane-1,4-diyl)bis(3-hydroxy-2-methylpyridin-4(1H)-one) (3a). Compound 16 (24 mg, 0.05 mmol) was suspended in 2 mL of conc. HCl solution and the suspension was stirred at mom temperature for 3 h. The solution became homogenous eventually and TLC indicated the complete disappearance of the starting material. The excess HCl solution was removed under vacuum and the residue was lyophilized to get title compound 3a (8.32 mg, 52%) as off-white solid. $^1$H NMR (500 MHz, MeOH-$d_4$) δ

8.26 (d, J=7.2 Hz, 1H), 7.14 (d, J=7.1 Hz, 1H), 2.68 (s, 3H), 2.32-2.12 (m, 4H). $^{13}$C NMR (126 MHz, MeOH-d$_4$) δ 160.2, 144.9, 142.8, 135.40, 112.1, 32.0. HRMS (ESI) m/z Calcd. for C$_{15}$H$_{23}$O$_4$N$_2$ [M+H]$^+$: 331.1652, found 331.1642.

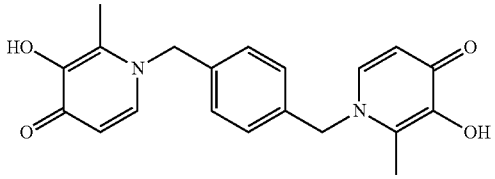 [SMILES: Cc1c(O)c(=O)ccn1Cc1ccc(Cn2ccc(=O)c(O)c2C)cc1]

1,1'-(1,4-Phenylenebis(methylene))bis(3-hydroxy-2-methylpyridin-4(1H)-one) (3b). Following the same reaction protocol as described for the synthesis of 3a, conc. HCl (2 mL) treatment (overnight instead of 3 h) of compound 17 (29 mg, 0.05 mmol) gave the title compound 3b (13 mg, 68%) as off-white solid. $^1$H NMR (500 MHz, MeOH-d$_4$) δ 8.16 (d, J=7.0 Hz, 1H), 7.30-7.11 (m, 2H), 7.07 (d, J=6.9 Hz, 1H), 5.55 (s, 2H), 2.38 (s, 3H). $^{13}$C NMR (126 MHz, MeOH-d$_4$) δ 160.5, 145.6, 143.4, 140.0, 136.1, 129.0, 111.8, 60.4, 13.1. FIRMS (ESI) m/z Calcd for C$_{20}$H$_{21}$O$_4$N$_2$ [M+H]$^+$: 353.1496, found 353.1493.

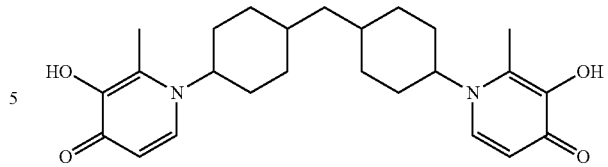

1,1'-(Methylenebis(cyclohexane-4,1-diyl))bis(3-hydroxy-2-methylpyridin-4(1H)-one) (3g). Following the same reaction protocol as described for the synthesis of 3a, conc. HCl (4 mL) treatment (overnight Mead of 3 h) of compound 18 (37 mg, 0.06 mmol) gave the title compound 3c (15 mg, 57%) as off-white solid. $^1$H NMR (500 MHz, MeOH-d$_3$) δ 8.40-8.15 (m, 1H), 7.07 (d, J=5.8 Hz, 1H), 4.46 (d, J=12.7 Hz, 1H), 2.59 (d, J=2.3 Hz, 3H), 2.10-1.62 (m, 7H), 1.60-1.39 (m, 1H), 1.17 (d, J=10.3 Hz, 2H). $^{13}$C NMR (126 MHz, MeOH-d$_4$) δ 159.2, 144.7, 111.9, 65.3, 34.5, 33.7, 33.1, 30.2, 28.7, 12.6. HRMS (ESI) m/z Calcd. for C$_{25}$H$_{33}$O$_4$N$_2$ [M+H]$^+$: 427.2591, found 427.2587.

General Synthesis of Compounds 36a-g

The reaction of mesylate 34 and desmethyltamoxifen 32 under standard conditions furnished alkyne tamoxifen compound 35. Subsequent CuI catalyzed Huigsen cyclization between benzyl protected azido maltol compounds 8a-f and alkyne 35 afforded the requisite compound 36a-f.

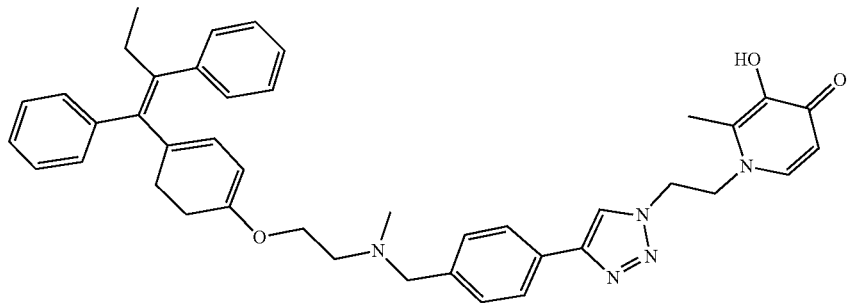

36a $^1$H NMR (400 MHz, CD$_3$OD) δ 8.24 (s, 1H), 7.75 (d, J=8.0 Hz, 2H), 7.53 (d, J=7.2 Hz, 1H), 7.43-7.01 (m, 13H), 6.79-6.69 (m, 2H), 6.61-6.49 (m, 2H), 6.36 (d, J=7.1 Hz, 1H), 4.45 (t, J=6.7 Hz, 2H), 3.99 (dd, J=11.1, 5.7 Hz, 4H), 3.62 (s, 2H), 2.76 (t, J=5.5 Hz, 2H), 2.43 (dd, J=12.7, 5.3 Hz, 2H), 2.40 (s, 3H), 2.30 (s, 3H), 2.09-1.93 (m, 2H), 1.78 (s, 2H), 1.39 (s, 2H), 0.89 (t, J=7.4 Hz, 3H).

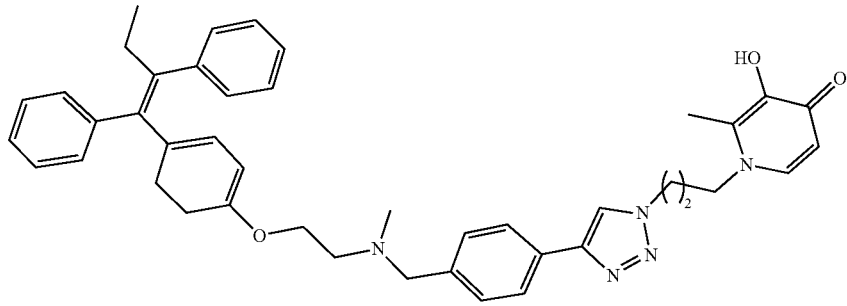

36b

¹H NMR (400 MHz, CD₃OD) δ 8.37 (s, 1H), 7.77 (d, J=8.2 Hz, 2H), 7.62 (d, J=6.7 Hz, 1H), 7.45-7.03 (m, 13H), 6.74 (d, J=8.9 Hz, 2H), 6.55 (d, J=8.9 Hz, 2H), 6.38 (d, J=7.1 Hz, 1H), 4.55 (s, 2H), 4.18-4.11 (m, 2H), 4.00 (t, J=5.5 Hz, 2H), 3.63 (s, 2H), 2.77 (t, J=5.6 Hz, 2H), 2.44 (q, J=7.5 Hz, 4H), 2.38 (s, 3H), 2.31 (s, 3H), 1.35 (d, J=6.6 Hz, 2H), 0.89 (t, J=7.4 Hz, 3H).
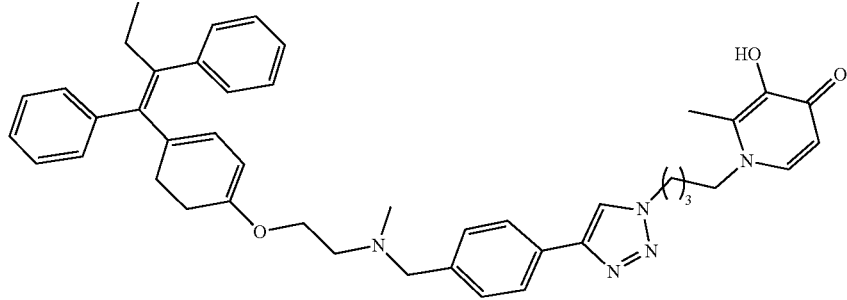
36c
¹H NMR (400 MHz, CD₃OD) δ 8.28 (s, 1H), 7.79-7.69 (m, 2H), 7.57 (dd, J=14.5, 6.0 Hz, 1H), 7.40-6.99 (m, 12H), 6.73 (d, J=8.7 Hz, 2H), 6.53 (d, J=8.7 Hz, 2H), 6.36 (t, J=9.0 Hz, 1H), 4.46 (s, 2H), 4.03 (s, 2H), 3.95 (t, J=5.2 Hz, 2H), 3.60 (s, 2H), 2.74 (t, J=5.1 Hz, 2H), 2.42 (q, J=7.4 Hz, 2H), 2.36 (s, 3H), 2.28 (s, 3H), 1.94 (d, J=25.4 Hz, 2H), 1.74 (s, 2H), 0.87 (t, J=7.4 Hz, 3H).
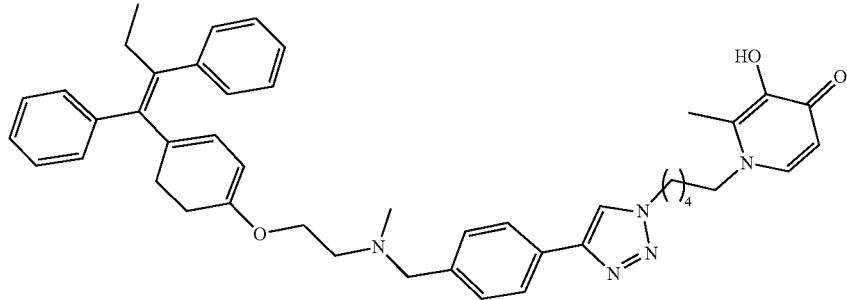
36d
¹H NMR (400 MHz, CD₃OD) δ 8.24 (s, 1H), 7.75 (d, J=8.0 Hz, 2H), 7.53 (d, J=7.2 Hz, 1H), 7.43-7.01 (m, 13H), 6.79-6.69 (m, 2H), 6.61-6.49 (m, 2H), 6.36 (d, J=7.1 Hz, 1H), 4.45 (t, J=6.7 Hz, 2H), 3.99 (dd, J=11.1, 5.7 Hz, 4H), 3.62 (s, 2H), 2.76 (t, J=5.5 Hz, 2H), 2.43 (dd, J=12.7, 5.3 Hz, 2H), 2.40 (s, 3H), 2.30 (s, 3H), 2.09-1.93 (m, 2H), 1.78 (s, 2H), 1.39 (s, 2H), 0.89 (t, J=7.4 Hz, 3H). ESI m/z [M+H]⁺ 708.4.
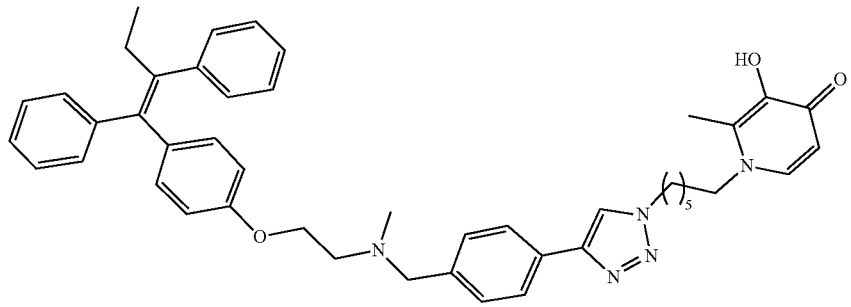
36e ¹H NMR (400 MHz, CD₃OD) δ 8.24 (s, 1H), 7.75 (d, J=8.0 Hz, 2H), 7.53 (d, J=7.2 Hz, 1H), 7.43-7.01 (m, 13H), 6.79-6.69 (m, 2H), 6.61-6.49 (m, 2H), 6.36 (d, J=7.1 Hz, 1H), 4.45 (t, J=6.7 Hz, 2H), 3.99 (dd, J=11.1, 5.7 Hz, 4H), 3.62 (s, 2H), 2.76 (t, J=5.5 Hz, 2H), 2.43 (dd, J=12.7, 5.3 Hz, 2H), 2.40 (s, 3H), 2.30 (s, 3H), 2.09-1.93 (m, 2H), 1.78 (s, 2H), 1.39 (s, 2H), 0.89 (t, J=7.4 Hz, 3H). ESI m/z [M+H]⁺ 722.5.

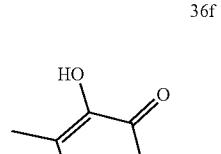

36f

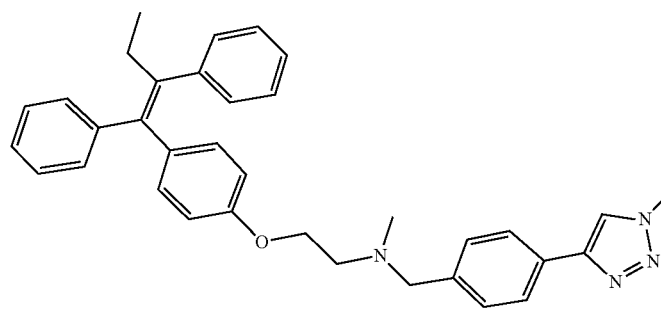

1H NMR (400 MHz, CD3OD) δ 8.31 (s, 1H), 7.77 (d, J=7.8 Hz, 2H), 7.57 (d, J=7.3 Hz, 1H), 7.46-7.01 (m, 13H), 6.74 (d, J=8.7 Hz, 2H), 6.55 (d, J=8.7 Hz, 2H), 6.35 (d, J=7.0 Hz, 1H), 4.44 (t, J=6.6 Hz, 2H), 4.00 (d, J=5.1 Hz, 4H), 2.78 (t, J=5.3 Hz, 2H), 2.43 (q, J=7.4 Hz, 2H), 2.38 (s, 3H), 2.32 (s, 3H), 1.95 (s, 2H), 1.70 (s, 2H), 1.37 (s, 7H), 0.89 (t, J=7.4 Hz, 4H).

36g

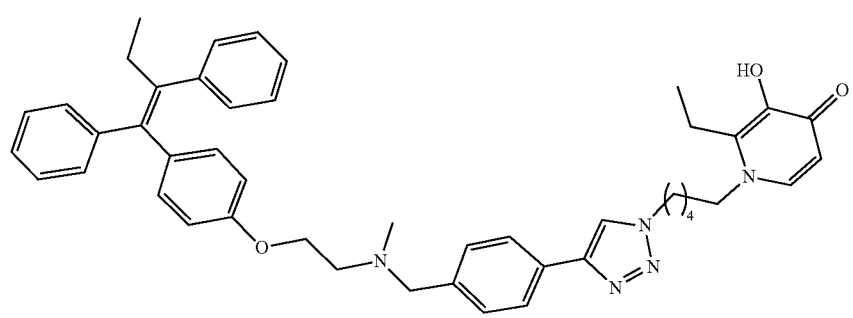

¹H NMR (400 MHz, CDCl₃) 11.86 (s, 1H), 11.66 (d, J=7.8 Hz, 2H), 11.33-10.93 (m, 14H), 10.67 (d, J=8.7 Hz, 2H), 10.45 (d, J=8.8 Hz, 2H), 10.30 (d, J=6.9 Hz, 1H), 7.90 (t, J=5.5 Hz, 2H), 7.83 (t, J=7.5 Hz, 2H), 7.56 (s, 2H), 6.70 (dd, J=15.5, 6.6 Hz, 4H), 6.34 (q, J=7.4 Hz, 2H), 6.23 (s, 3H), 5.99-5.85 (m, 2H), 5.72 (s, 2H), 5.32 (s, 2H), 5.15 (s, 2H), 5.12 (d, J=7.4 Hz, 3H), 4.81 (t, J=7.4 Hz, 3H), 13C NMR (101 MHz, cdcl3) δ 169.71, 156.62, 147.77, 145.84, 143.77, 142.36, 141.32, 138.16, 136.70, 135.57, 133.49, 131.86, 129.67, 129.43, 128.09, 127.86, 126.51, 126.00, 125.56, 119.58, 113.32, 111.43, 65.79, 62.17, 55.70, 53.11, 49.83, 42.72, 31.03, 29.83, 29.70, 29.01, 23.40, 19.32, 13.62, 12.84.

Example VI: DFP Binds to Fe2+ Ion at the Active Site of KDM6A

Figures 3A, 3B:
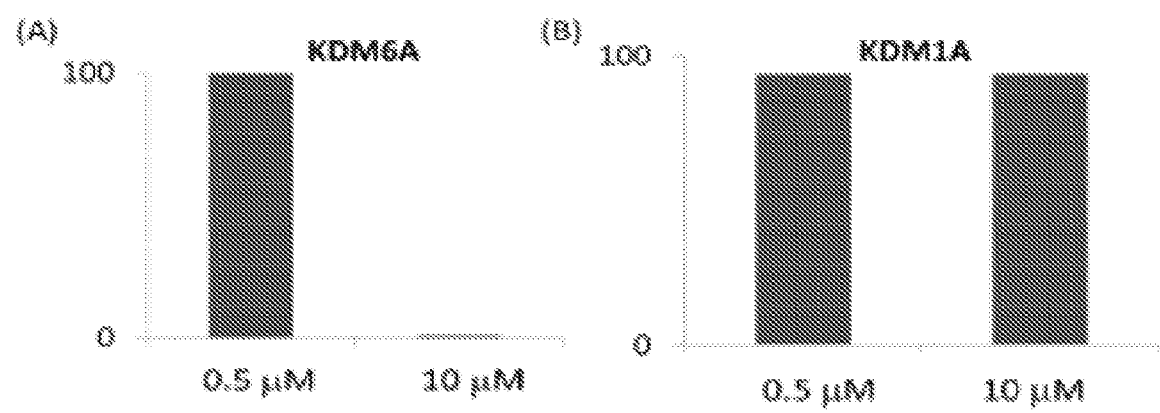
FIGS. 3A and 3B are bar graphs showing DFP inhibits KDM6A (3A) while inactive against Flavin-dependent KDM1A (3B).

DFP was interrogate with KDM6A, a representative KDM which regulates gene expression programs associated with BCa proliferation and invasion. This docking analysis built on our previous studies where we used the molecular docking program AutoDock 4.2 to successfully identify from this library 3-hydroxypyridin-2-thione as a non-hydroxamate zinc binding group that is compatible with HDAC inhibition Analyses of the molecular docking outputs revealed that DFP adopts docked poses in which it strongly chelate Fe2+ at the active site of KDM6A. In addition to iron chelation, the interaction is further stabilized by H-bonding between the oxygen moieties of DFP and two key residues within the enzymes active sites: phenolic group of Tyr 1135 and OH group of Ser 1154. The N-1 position of the DFP is oriented toward the exit channel of the active site (FIG. 2a), an orientation that should permit modifications which may enhance KDM binding affinity. Subsequent molecular dockings with KDMs 2A, 7A, and 7B revealed that DFP adopted docked poses and maintained similar interaction as the ones in KDM6A (FIGS. 2b-d) while devoid of interaction with KDM5A (FIG. S2) and Flavin-dependent KDM1A Example VII: DFP Binds to a Subset of KDMs To test the validity of our in silico predictions, we first investigated the effects of DFP on activities of KDM1A and KDM6A at two concentrations—0.5 and 10 μM. We observed that DFP showed a concentration dependent inhibition of KDM6A, resulting in >95% reduction in the enzyme activity at 10 μM. In contrast. DFP has no effect on the activity of KDM1A at both concentrations (FIG. 3). Subsequently, we determined the effects of DFP on the enzymatic activities of seventeen recombinant human KDMs using a cell-free enzymatic assay. We observed that DPP inhibits the demethylase activities of six KDMs—2A, 2B, 5C, 6A, 7A and 7B—at low micromolar IC₅₀s while considerably less active or inactive against eleven KDMs—1A, 3A, 3B, 4A-E, 5A, 5B and 6B

Example VIII: DFP Potently Inhibits H3K27 Demethylation

Figures 4A, 4B:
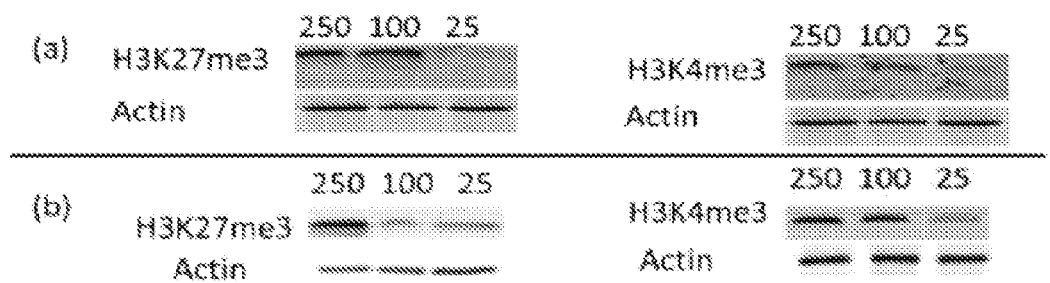
FIGS. 4A and 4B are autoradiographs showing DFP elicits dose-dependent inhibition of H3K4me and H3K27me in MCF-7 (4A) and MDA-MB-231 cells (4B).
Figure 5A:
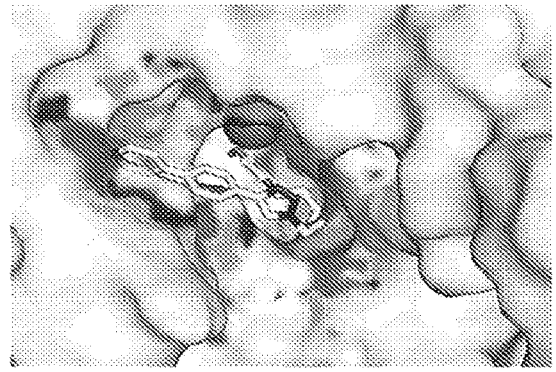
FIGS. 5A-5D are illustrations of docked poses of representative DFP derivatives.
Figure 5B:
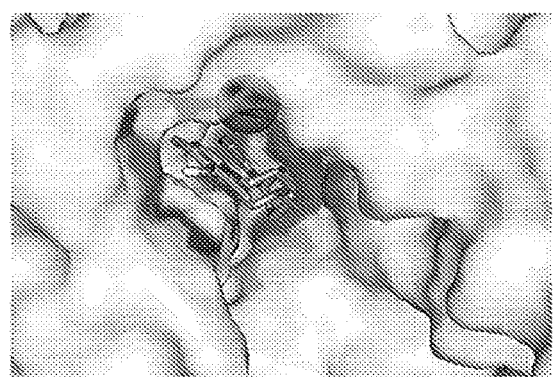
Figure 5C:
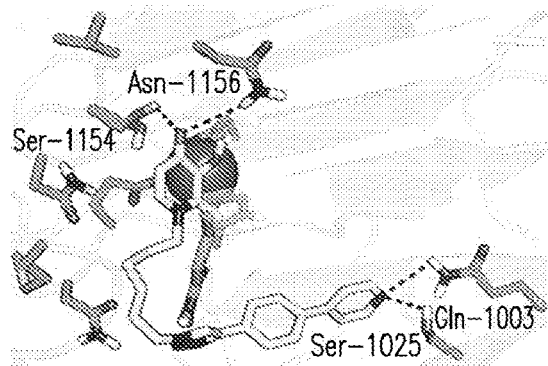
Figure 5D:
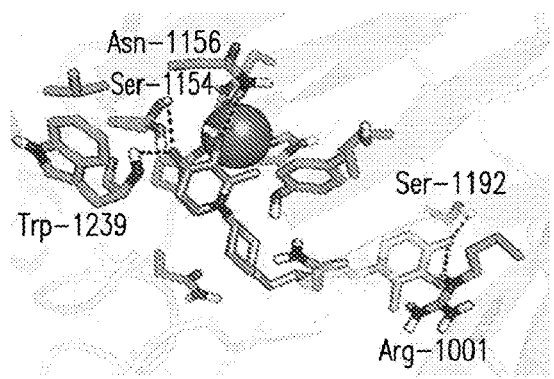

To confirm if the KDM inhibition activities displayed by DFP in the cell-free assay translated to intracellular effect, we performed Western blot analyses on cell lysates from MCF-7 and MDA-MB-231 cells treated with various concentration of DFP. We probed for the levels of H3K4me3 and H3K27me3, two chromatin posttranslational marks that are subject to demethylation by several KDM subfamilies, including KDM 2B [26], 5C [27] and 6A [28] which are inhibited by DFP in our cell-free assay. We observed that DFP induced a dose-dependent upregulation of H3K4me3 and H3K27me3 levels in these cells (FIG. 4). This observation strongly suggests that DIP potently inhibits H3K4me3 and H3K27me3 demethylation intracellularly.

Example IX

Structure Activity Relationship (SAR) Studies. Our docking analysis revealed that the N-1 moiety of DFP is presented toward an exit channel, away from the active sites of several KDMs (FIG. 2). To explore if interaction within this channel will result in enhancement of potency, we designated three distinct structural classes of DFP analogs (Classes I (unsubstituted aryl 1a-f), II (substituted aryl 2a-w) and III (bisDFP 3a-g), building from the N-1 position. Molecular docking analysis revealed that representatives of these compounds optimally occupied the channel while maintaining $Fe^{2+}$ chelation

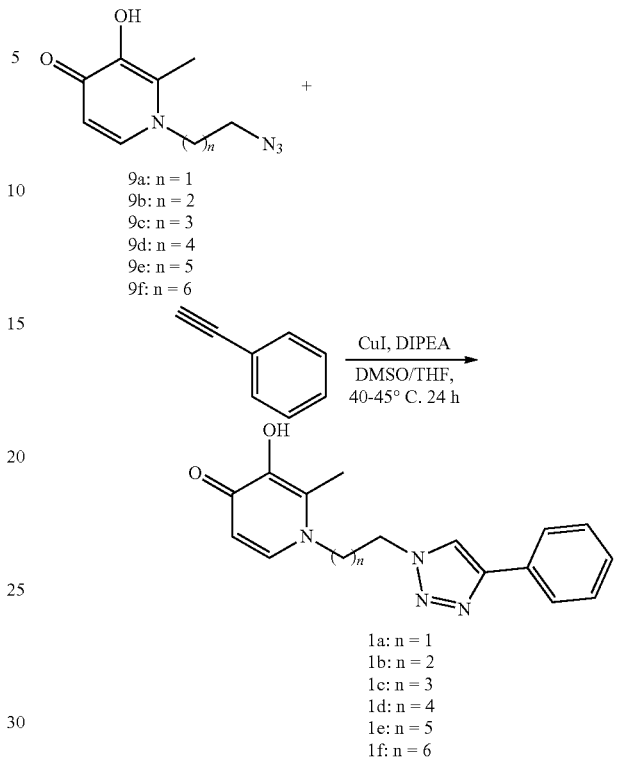

Scheme 3: Synthesis of BisDFT KDM inhibitors (3a-g)

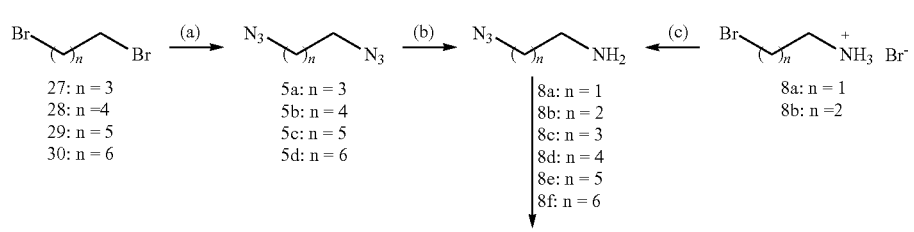

Scheme 1: Synthesis of Azidoalkyl-3-hydroxypyridin-4-one.

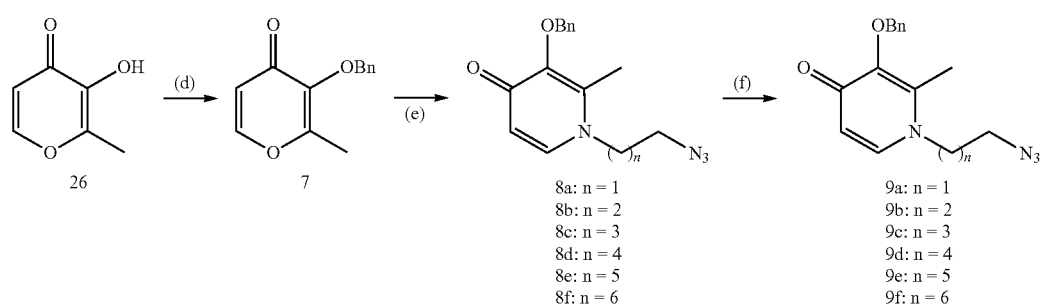

Reagents and conditions: (a) $NaN_3$, DMF, 80° C., 20 h; (b) $PPh_3$, 5% HCl, EtOAC:Ether, 40 h; (c) (1) $NaN_3$, $H_2O$, 80° C., 12 h; (2) aq KOH; (d) benzyl chloride, $K_2CO_3$, DMF, 110° C., 3 h; (e) NaOH, EtOH:$H_2O$, 110° C. under pressure, 72 h; (f) conc. HCl, 4-6 h.

-continued

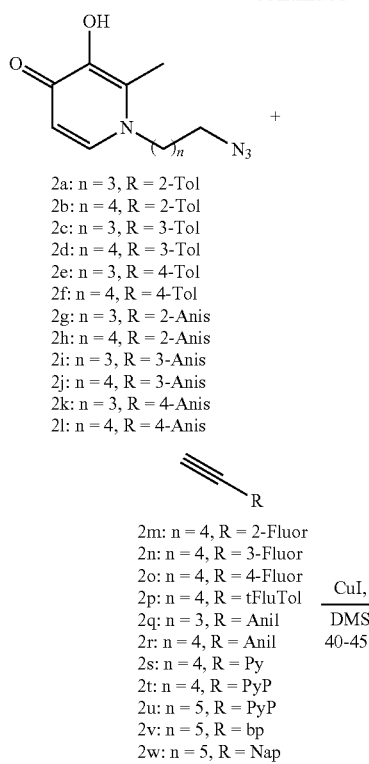

2a: n = 3, R = 2-Tol
2b: n = 4, R = 2-Tol
2c: n = 3, R = 3-Tol
2d: n = 4, R = 3-Tol
2e: n = 3, R = 4-Tol
2f: n = 4, R = 4-Tol
2g: n = 3, R = 2-Anis
2h: n = 4, R = 2-Anis
2i: n = 3, R = 3-Anis
2j: n = 4, R = 3-Anis
2k: n = 3, R = 4-Anis
2l: n = 4, R = 4-Anis 2m: n = 4, R = 2-Fluor
2n: n = 4, R = 3-Fluor
2o: n = 4, R = 4-Fluor
2p: n = 4, R = tFluTol
2q: n = 3, R = Anil
2r: n = 4, R = Anil
2s: n = 4, R = Py
2t: n = 4, R = PyP
2u: n = 5, R = PyP
2v: n = 5, R = bp
2w: n = 5, R = Nap CuI, DIPEA
DMSO/THF,
40-45° C. 24 h

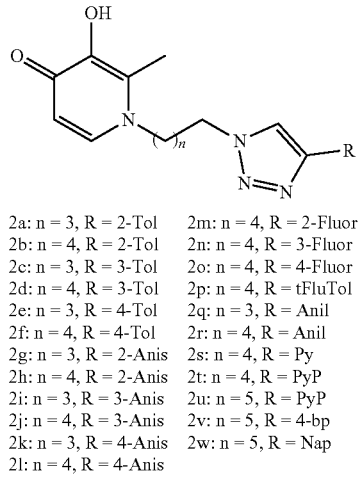

2a: n = 3, R = 2-Tol
2b: n = 4, R = 2-Tol
2c: n = 3, R = 3-Tol
2d: n = 4, R = 3-Tol
2e: n = 3, R = 4-Tol
2f: n = 4, R = 4-Tol
2g: n = 3, R = 2-Anis
2h: n = 4, R = 2-Anis
2i: n = 3, R = 3-Anis
2j: n = 4, R = 3-Anis
2k: n = 3, R = 4-Anis
2l: n = 4, R = 4-Anis 2m: n = 4, R = 2-Fluor
2n: n = 4, R = 3-Fluor
2o: n = 4, R = 4-Fluor
2p: n = 4, R = tFluTol
2q: n = 3, R = Anil
2r: n = 4, R = Anil
2s: n = 4, R = Py
2t: n = 4, R = PyP
2u: n = 5, R = PyP
2v: n = 5, R = 4-bp
2w: n = 5, R = Nap

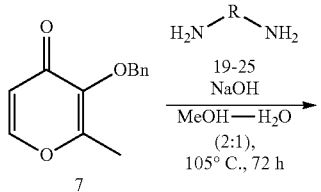

19-25
NaOH
MeOH—H₂O
(2:1),
105° C., 72 h

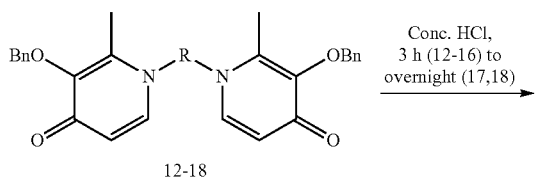

Conc. HCl,
3 h (12-16) to
overnight (17,18)

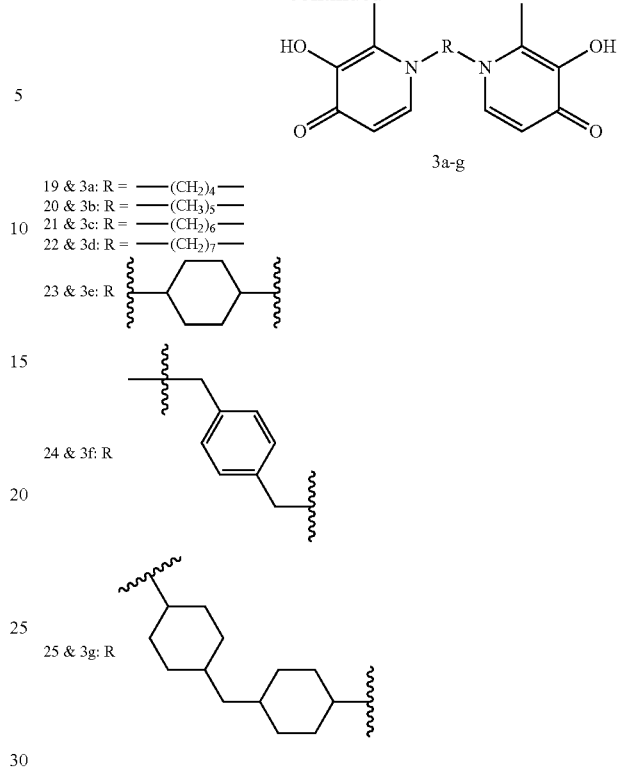

3a-g

19 & 3a: R = —(CH₂)₄—
20 & 3b: R = —(CH₃)₅—
21 & 3c: R = —(CH₂)₆—
22 & 3d: R = —(CH₂)₇—

23 & 3e: R

24 & 3f: R

25 & 3g: R

To preliminarily profile the bioactivity of these compounds, we adopted a streamlined approach which involved screening against KDM6A at two concentrations and evaluating antiproliferative activity against three representative cell lines—MCF-7 (ER(+) BCa), MDA-MB-231 (TNBC BCa) and Vero (a non-transformed cell line as control). Similar to DFP, these compounds caused concentration dependent inhibition of KDM6A, resulting in 96-100% reduction in the enzyme activity at 10 μM (Tables 2-3). Subsequently, we observed that a subset of compounds from each class displayed tumor-selective cytotoxic against the BCa cell lines tested, with potency enhancement as high as 93-fold relative to DFP (Tables 4-6). Intriguingly, these compounds are preferentially more cytotoxic to the TNBC cell line MD4 MB-231. Encouraged by these positive attributes, we determined the $IC_{50}$ of representative potent members of each class—1d, 2j, 2u and 3g against KDM6A. We found that they inhibited KDM6A with low micromolar $IC_{50}$ (FIG. 6). Relative to DFP however, the KDM6A inhibition potencies of these lead compounds are enhanced by 1.3 to-fold and this does not completely explain the observed ~31-93-fold enhancement of the cytotoxicity of the best compounds in this series to MDA MB-231 (Tables 5-6). This may be due to several factors including reduced tendency of 1d, 2j, 2u and 3g, relative to DFP, to form tridentate complex with intracellularly free iron in ferric state ($Fe^{3+}$) [29], the difference in their preference for KDM subfamily, or their improved cell penetration. We then performed Western blot analyses on cell lysates from MDA-MB-231 cells treated with various concentrations of 1d and 2u to probe if the KDM inhibition activities in the cell-free assay translate to intracellular effect. We observed that 1d and 2u induced a dose-dependent upregulation of H3K4me3 and H3K27me3 levels at concentrations that are 10-times lower than those of DFP (FIG. 6b). This observation may indicate that 1d and 2u have better cell penetration properties than DFP, an attribute which may partly explain the enhanced antiproliterative activities of these DFP-based KDM inhibitors.

(a)

KDM6A Activity inhibition (%) of 1a-f and 2a-w at 1 μM and 10 μM.

KDM6A (UTX) Inhibition (%)

| Compound | R | n | 1 (μM) | 10 (μM) |
|---|---|---|---|---|
| 1a | phenyl | 1 | 12 | 96 |
| 1b | phenyl | 2 | 6 | 100 |
| 1c | phenyl | 3 | 8 | 100 |
| 1d | phenyl | 4 | 12 | 100 |
| 1e | phenyl | 5 | 12 | 98 |
| 1f | phenyl | 6 | 10 | 99 |
| 2a | 2-methylphenyl | 3 | 6 | 100 |
| 2c | 3-methylphenyl | 3 | 4 | 100 |
| 2e | 4-methylphenyl | 3 | 13 | 100 |

-continued

KDM6A (UTX) Inhibition (%)

| Compound | R | n | 1 (μM) | 10 (μM) |
|---|---|---|---|---|
| 2h | 2-methoxyphenyl | 4 | 3 | 99 |
| 2i | 3-methoxyphenyl | 3 | 7 | 100 |
| 2j | 3-methoxyphenyl | 4 | 8 | 100 |
| 2l | 4-methoxyphenyl | 4 | 4 | 100 |
| 2m | 2-fluorophenyl | 4 | 16 | 100 |
| 2n | 3-fluorophenyl | 4 | 5 | 100 |
| 2o | 4-fluorophenyl | 4 | 10 | 100 |
| 2p | 2-trifluoromethylphenyl | 4 | 15 | 99 |
| 2s | 2-pyridyl | 4 | 15 | 99 |

-continued

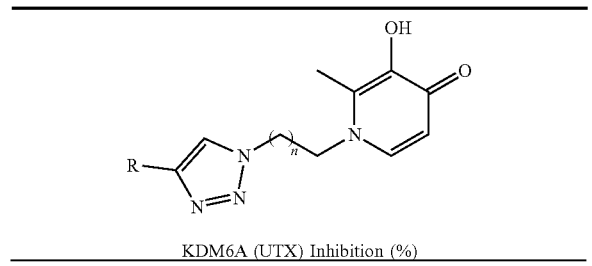

KDM6A (UTX) Inhibition (%)

| Compound | R | n | 1 (μM) | 10 (μM) |
|---|---|---|---|---|
| 2t | ![pyridinyl-phenyl] | 4 | 8 | 99 |

Antiproliferative Activity of Compounds 1a-f and DFP.

[Structure: bis-pyridinone linked by R]

KDM6A (UTX) Inhibition (%)

| Compound | R | n | 1 (μM) | 10 (μM) |
|---|---|---|---|---|
| 3a | (CH2)2 linker | | 4 | 100 |
| 3b | (CH2)3 linker | | 1 | 99 |
| 3c | (CH2)4 linker | | 2 | 100 |
| 3d | (CH2)5 linker | | 3 | 100 |
| 3e | cyclohexyl linker | | 5 | 100 |
| 3f | p-xylylene linker | | 4 | 100 |
| 3g | bis-cyclohexyl-methylene linker | | 9 | 100 |

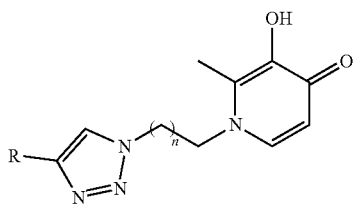

Anti-proliferative Activity IC$_{50}$ (μM)

| Compound | R | n | MDA-MD-231 | MCF-7 | VERO |
|---|---|---|---|---|---|
| 2a | o-tolyl | 3 | 16.4 | ND$^a$ | 11.6 |
| 2b | o-tolyl | 4 | 12.7 | ND | 5.8 |

-continued
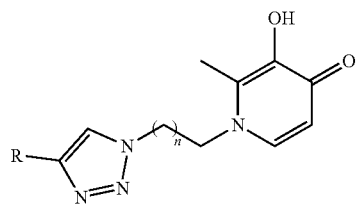
Anti-proliferative Activity IC$_{50}$ (μM)
| Compound | R | n | MDA-MD-231 | MCF-7 | VERO |
|---|---|---|---|---|---|
| 2c | 3-methylphenyl | 3 | 10.9 | ND | 5.2 |
| 2d | 3-methylphenyl | 4 | 11.8 | ND | 3.6 |
| 2e | 4-methylphenyl | 3 | 7.4 | ND | 4.1 |
| 2f | 4-methylphenyl | 4 | 15.7 | ND | 3.1 |
| 2g | 2-methoxyphenyl | 3 | 9.6 | ND | >50 |
| 2h | 2-methoxyphenyl | 4 | 19.1 | ND | >50 |
| 2i | 3-methoxyphenyl | 3 | 7.5 | ND | >50 |
| 2j | 3-methoxyphenyl | 4 | 19.6 | ND | >50 |
| 2k | 4-methoxyphenyl | 3 | 8.1 | ND | >50 |

-continued
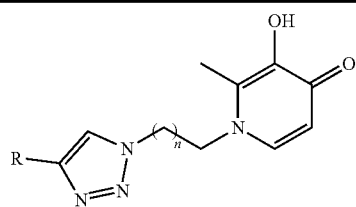
Anti-proliferative Activity IC$_{50}$ (μM)
| Compound | R | n | MDA-MD-231 | MCF-7 | VERO |
|---|---|---|---|---|---|
| 2l | 4-methoxyphenyl | 4 | 9.6 | ND | >50 |
| 2m | 2-fluorophenyl | 4 | 18.3 | ND | 12.7 |
| 2n | 3-fluorophenyl | 4 | 6.8 | ND | 22.9 |
| 2o | 4-fluorophenyl | 4 | 3.6 | ND | 38.8 |
| 2p | 2-trifluoromethylphenyl | 4 | 18.8 | ND | 13.3 |
| 2q | 4-(dimethylamino)phenyl | 3 | 9.5 | ND | >50 |
| 2r | 4-(dimethylamino)phenyl | 4 | 12.5 | ND | >50 |
| 2s | 2-pyridyl | 4 | NI[b] | ND | >50 |
| 2t | 4-(4-pyridyl)phenyl | 4 | 3.6 | ND | 29.2 |

-continued
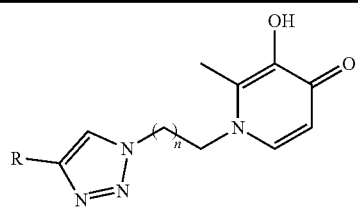
Anti-proliferative Activity IC$_{50}$ (μM)
| Compound | R | n | MDA-MD-231 | MCF-7 | VERO |
|---|---|---|---|---|---|
| 2u | 4-pyridyl-phenyl | 5 | 1.7 | ND | 66.9 |
| 2v | biphenyl | 5 | 2.5 | ND | 4.9 |
| 2w | 6-methoxy-naphthyl | 5 | 1.2 | ND | 3.9 |
[a]ND, not determinable  
[b]NI, no inhibition
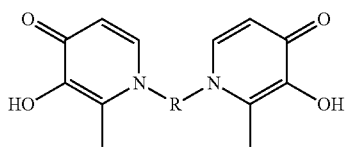
Anti-proliferative Activity IC$_{50}$ (μM)
| Compound | R | MDA-MB-231 | MCF-7 | VERO |
|---|---|---|---|---|
| 3a | -(CH$_2$)$_2$- | NI[a] | NI | NI |
| 3b | -(CH$_2$)$_3$- | NI | NI | NI |
| 3c | -(CH$_2$)$_4$- | NI | NI | NI |
| 3d | -(CH$_2$)$_5$- | NI | NI | NI |
| 3e | cyclohexyl | 36.9 | ND[b] | NI |

-continued

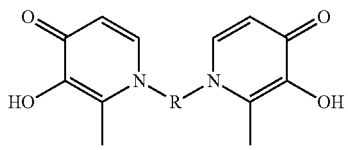

Anti-proliferative Activity IC$_{50}$ (μM)

| Compound | R | MDA-MB-231 | MCF-7 | VERO |
|---|---|---|---|---|
| 3f | (p-xylylene linker) | 25.0 | ND | NI |
| 3g | (dicyclohexylmethane linker) | 3.50 | ND | >50 |

[a]NI, no inhibition
[b]ND, not determinable

Example X

DFP-based KDM inhibitors slow HP1-stimulated heterochromatin gene repression: To elucidate the effect of DFP-based KDM inhibitors have on chromatin dynamics, we profiled them in an intracellular assay which measures heterochromatin formation speed. The chromatin assay (CiA) leverages chemical induced proximity (CIO) to recruit heterochromatin protein 1 (HP1) to a modified Oct4 locus. This reporter system inserts tandem arrays of Gal4 and zinc finger DNA binding domains in the promoter of one allele of Oct4, where the gene is replaced by a nuclear eGFP reporter. Protein fusions of Gal4-FKBP and FRB-HP1 allow for direct chemical recruitment of HP1 to the CiA:Octr reporter locus upon addition of the chemical inducer of proximity (CIP)-rapamycin. After CIP-rapamycin addition, JP1 is recruited to the reporter locus and brings histone methyltransferase enzymes to the chromatin reporter resulting in the repressive H3K9me3 mark being deposited. H3K9me3 deposition leads to heterochromatin formation and gene silencing (FIG. 7A) [30]. Others have shown that H3K4me3 marked nucleosomes impede H3K9 methyltransferases [31]. Thus, we postulate that the active H3K4me3 mark must be removed by KDM enzymes as part of the transformation from euchromatin to heterochromatin. Inhibition of KDMs, specifically those targeting H3K4me3, would result in a decrease in H3K9me3 accumulation, which would be measured in our assay as an increase in % GFP (+) cells.

To determine the effect of DFP-based KDM inhibitors on HP1-mediated gene repression, we treated CIA:Oct4 embryonic stem (ES) cells with doses of representative compounds ranging from 10,000 μM-250 nM for 4.8 h with and without CIP-rapamycin recruiting HP1 (FIG. 7B). For this experiment, we chose representative compounds which displayed potent tumor-selective cytotoxic from each class (2j, 2t, 2v, 2w and 3g), one representative compound which displayed considerably weaker cell cytotoxicity (1a) and DFP. We observed that compounds 2v and 2w were the most potent inhibitors of heterochromatin formation reaching max inhibition at 1 μM. Compound 3g reached maximum inhibition at 2.5 μM while 2t only reached maximum inhibition of gene repression at 10 μM, 2j had a 20% increase in GFP expression. Compound 1a and DFP were weak inhibitors of heterochromatin formation.

recruitment of HP1 by CIP-rapamycin addition leads to gene silencing. Dose response curves of DFP derivatives oiler 48 h with C) and without D) HP1 recruitment at, 10000, 5000, 2500, 1000, 500, 250, and 0 nM concentrations. Flow cytometry was used to determine the % GFP (+) cells following treatment. n=6

Discussion

DFP, a hydroxypyridinone-derived iron chelator currently in clinical use for iron chelation therapy, elicits antiproliferative activities through mechanisms not clearly understood. The depletion of intracellular iron caused by DFP and the indirect inhibition of DNA synthesis through inactivation of RNR; and reduction of intracellular $Zn^{2+}$pool, have been suggested to be key contributing factors to the DFP-induced apoptosis [3-9, 14]. Hydroxypyridinones, including DFP, form complexes having metal ions to ligand stoichiometry that is dependent on the identity of the chelated metal ion [29] The diversity of DFP-metal ion complexes and its small flat aromatic structure could enable DFP gain access to the active sites of several intracellular metalloenzymes. We have shown in our previous studies that the thiophilicity of zinc enhances the chelation of $Zn^{2+}$ ion at the active site of HDAC6 and HDAC8 to 3-hydroxypyridin-2-thione relative to the closely related hydroxypyridin-2-one, resulting in inhibition of these HDAC isoforms [15, 16]. Subfamily of $Fe^{2+}$-dependent KDMs have active site architecture which resembles HDACs' and may prefer chelation to DFP because of the low thiophilicity of iron.

In the first half of this study, we have used a combination of in silico molecular docking, cell-free and cell based-assays to investigate the interaction of DFP with KDMs. As shown in FIG. 2, we found that DFP gained access to and formed a bidentate chelate with the $Fe^{2+}$ at the active site of a subset of KDMs. The DFP-KDM interaction is further stabilized by H-bonding between the oxygen moieties of DFP and key residues within the enzymes active sites. This in silico observation implicates DFP as a potential inhibitor of the demethylase activity of these KDMs. Subsequent cell-free assay, monitoring KDM enzymatic activity, confirms our in silico prediction. We observed that DFP inhibits six KDMs—2A, 2B, 5C, 6A, 7A and 7B—at low micromolar $IC_{50}$s. We also found DFP was considerably less active or inactive against eleven KDMs—1A, 3A, 3B, 4A-E, 5A, 5B and 6B. Results from Western blot analyses (FIG. 4) revealed that DFP caused a dose dependent elevation of H3K4me3 and H3K27me3 levels in MCF-7 cells. This provided evidence for the intracellular KDM inhibition activities of DFP. It is plausible that DFP derives part of its antiproliferative properties from a convergence of KDM inhibition and metal ion chelation-induced perturbation of some intracellular pathways vital to tumor cell growth. DFP elicits KDM inhibition activities at concentrations that are between 7- and 70-fold lower than the iron binding equivalence concentrations at which it inhibits RNR activities and/or reduces labile intracellular zinc ion pool [8, 9, 14]. Thus, it is highly likely that DFP derives its anti-proliferative activity largely from the inhibition of a sub-set of KDMs identified in this study.

The initial in silico docking study on DFP revealed structure-based insights for the optimization of DFP. These in silico observations provided a foundation for the SAR study that furnished several novel DFP-based KDM inhibitors which are preferentially more cytotoxic to the TNBC cell line MDA-MB-231. Several members of KDM sub-families have been implicated in the epigenetic reprogramming which sustains BCas regardless of hormone expression status [23, 24, 32-36]. The basis for the TNBC cell line selectivity of these DFP-based compounds is not completely clear from this study. Yet we further found that representative compounds 2j, 2t, 2v, 2w and 3g, which displayed potent tumor-selective cytotoxic, have intracellular KDM inhibition activities in an orthogonal assay which measures heterochromatin gene repression velocity following HP1 recruitment to the CiA:Oct4 locus. Here these compounds, significantly inhibited heterochromatin firing at a relevant mammalian locus. We hypothesize this occurs from pan KDM inhibition including H3K4me3 which impeded H3k9me3 deposition and gene silencing. This data is in agreement with our cell-free and cell-based assays.

In conclusion, our study has furnished a new insight into the mechanism of the anti-proliferative activities of DFP as we revealed that DFP is a pan-selective KDM inhibitor. The docked poses adopted by DFP at KDM active sites also permitted modifications which enabled identification of new DFP-based anti-proliferative agents which displayed selective cytotoxicity against a TNBC cell line and caused a delay in heterochromatin gene repression. Taken together our study has identified a new chemical scaffold capable of inhibiting KDM enzymes, globally changing histone modification profiles, and with specific anti-tumor activities.

Materials and Methods

Maltol and the phenylacetylene derivatives were purchased from Sigma Aldrich. Anhydrous solvents and other reagents were purchased either from Sigma or Acros and were used without further purification. Analtech silica gel plates (60 F254) were utilized for purification. Silica gel (200-400 mesh) was used in column chromatography. TLC plates were visualized using UV light, anisaldehyde, and/or iodine stains. NMR spectra were obtained on a Varian-Gemini 400 MHz and Broker Ascend™ (500 and 700 MHz) magnetic resonance spectrometer. $^1$H NMR spectra were recorded in parts per million (ppm) relative to the residual peaks of $CHCl_3$ (7.24 ppm) in $CDCl_3$ or $CHD_2OD$ (4.78 ppm) in $CD_3OD$ or DMSO-$d_5$ (2.49 ppm) in DMSO-$d_6$. MestReNova (version 11.0) was used to process the original "fid" fibs. High-resolution mass spectra were gathered with the assistance of the Georgia Institute of Technology mass spectrometry facility (Atlanta, GA). Bisazidoalkanes, benzylmaltol, and azidopropyl-hydroxy-methylpyridin-4(1H)-one were synthesized according to literature protocols [37, 38].

Molecular Docking Analysis

Prior to docking analysis with the appropriate macromolecule (KDM structure) in PyRx, energy minimization of the ligand and merging of non-polar hydrogens were performed in Chem3D 15.1 and Autodock Vina [25], respectively. After the removal of the heteroatoms, preparations of the macromolecules were performed directly in PyRx where the docking runs were achieved within a 25 Å cube surrounding the active site. Upon the completion of the runs, the results were reported as nine outputs, ranked in accordance to their binding affinity. For molecular interaction analysis, the macromolecule, along with the best fit outputs from PyRx were loaded onto PyMOL where the docked orientations along with molecular interactions were assessed.

KDM Cell-Free Assay

This experiment was done through a contractual agreement with BPS Bioscience, San Diego, CA.

Western Blot Analysis for H3 Methylation

The MCF-7 cells cultured in non-phenol red DMEM with 10% charcoal stripped FBS (Atlanta Biologicals, GA). Prior to treatment with the appropriated agents, the cells ($10^6$ cells per well) were plated in a 6-well plate (Techno Plastic Products AG, Trasadingen, Switzerland). After 24 hours incubation at 37° C. under a 5% $CO_2$ atmosphere, the initial media was aspirated and the cells were treated with the drug in triplicate with a final concentration of 1% DMSO. Subsequent to treatment, the cells were incubated under the same condition for 72 hours and lysed in the RIPA lysis buffer (10 mM Tris-Cl (pH 8.0), 1 mM EDTA, 1% Triton X-100, 0.1% sodium deoxycholate, 0.1% SDS, 140 mM NaCl, and 1 mM PMSF). Cell lysates were centrifuged at 14,000 rpm at 4° C. for 10 minutes, and the supernatant was transferred to a new tube, mixed with SDS loading dye (100 mM Trig-Cl (pH 6.8), 4% (w/v) sodium dodecyl sulfate, 0.2% bromophenol blue, 200 mM dithiothreitol), followed by heating at 100° C. for 5 minutes Samples were analyzed for the expression levels of H3K4me3 and H3K27me3 by Western Blotting using an anti-H3K4me3 antibody (Millipore, 07-473) and an anti-H3K27me3 antibody (Millipore, 07-449), respectively. Western blotting of cell lysates with an anti-β-ACTIN antibody (Sigma-Aldrich, A5316) was included as a loading control Cell lysates in SDS loading dye as described above were loaded onto 15% Acrylamide Gels for SDS Polyacrylamide Gel Electrophoresis (SDS-PAGE), followed by transferring the proteins to nitrocellulose membranes (Bio-Rad, Cat #162-0115) using a BioRad Trans-Blot® Electrophoretic Transfer Cell according to the manufacturers manual. The membranes were subsequently incubated for one hour with blocking buffer (Odyssey® Blocking Buffer (PBS), Cat #927-40000), followed by incubation with the primary antibodies for one hour at room temperature. The membranes were washed and incubated for one hour in room temperature in blocking buffer with secondary antibodies and washed. The images of the Western blots were scanned by LI-COR's Odyssey® (LI-COR) and the signal intensities were quantified using Image Studio™ software (LI-COR).

Mouse Embryonic Stem Cell Lines and Culturing

Mouse embryonic stem cells were adapted to be grown feeder free on gelatin coated plates in DMEM supplemented with 4.5 g/L glucose, 15% FBS, L-glutamate, sodium pyruvate, HEPES buffer, NEAR, 2-mercaptoethanol, LIF, and penicillin/streptomycin (ES Media) at 37° C. supplemented with 5% $CO_2$. ES media was aspirated and replaced daily.

The CiA:Oct4 recruitment system in mouse embryonic stem cells contains Gal4 and Zinc finger DNA binding arrays and a downstream nuclear eGFP gene in place of a single Oct4 allele as previously described [30]. The CiA: Oct4 N118/N163 cell line containing viral integrations of N118 and N163 plasmids (N118-nLV EF-1α-Gal-FKBPx1-HA-PGK-Blast, N163-nLV EF-1α-HP1α (CS)-Frbx2(Frb+FrbWobb)-V5-PGK-Puro) was used for inhibition of HP1-mediated heterochromatin studies. All plasmids are freely available on addgene.

HP1-Recruitment Assay Dose Curve

Day 0, CiA:Oct4 N118/163 cells were grown in ES media and seeded at a density of 10,000 cells per well (100,000 cells/ml) into gelatin coated 96 well plates. Day 1, culture media was aspirated and replaced with 100 μl ES media containing +/−6 nM rapamycin, 10 μM, 5 μM, 2.5 μM, 1 μM, 500 nM, and 250 nM concentrations of compound or DMSO were added using a TTP Labtech Mosquito HTS liquid handler. Days 2-4, fresh ES media+/−rapamycin and compound were added as in Day 1.

Day 3 and 5, cells were washed with PBS and trypsinized using 0.25% trypsin-EDTA. Trypsin was quenched with serum. Cells were resuspended by pipetting in preparation for flow cytometry analysis.

Flow Cytometry and Cell Sorting

Flow cytometry data was acquired using the Intellicyt iQue Screener and analyzed with FlowJo software. Cell populations were gated based on forward and side scatter height. Single cell populations were gated using forward scatter area by forward scatter height. Autofluorescent cells were excluded and the remaining cells were gated into GFP (−) and GFP (+) populations based on DMSO control samples. Histograms demonstrate representative samples while dose curve scatter plots contain all biological replicates (n=6).

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A compound according to Formula I:

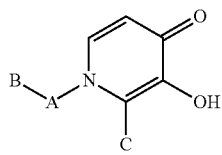

Formula I wherein
A is —$(CH_2)_n$—, wherein n is from 2-8;
B is AR-AR';
AR' is a linking group connecting AR and A, and AR' is selected from the group consisting of

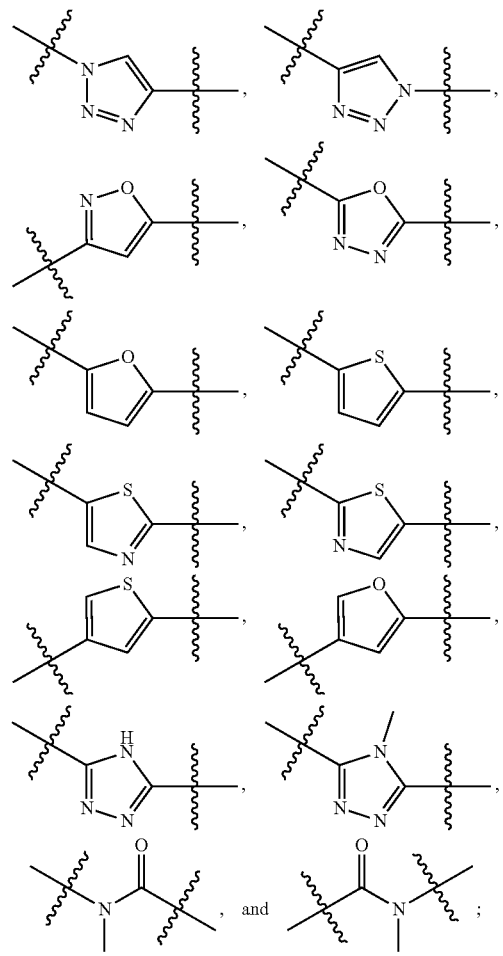

AR is aryl, 6-membered aromatic, heterocyclic, fused aromatic, fused heterocyclic, biaromatic, or a biheterocyclic ring system, wherein the aryl, 6-membered aromatic, heterocyclic, fused aromatic, fused heterocyclic, biaromatic or biheterocyclic ring system is optionally substituted by halogen-, alkyl-, alkoxy-, haloalkyl-, alkylamino-, aryl-, heteroaryl-, alkenyl-, alkynyl- or X;

X is:

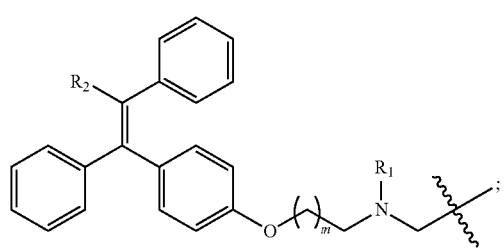

$R_1$ is H or $C_1$-$C_6$ alkyl;

$R_2$ is halogen, alkyl or aryl;

m is from 1-5; and

Y is alkyl or aryl, or a hydrate thereof, or a solvate thereof, or a pharmaceutically acceptable salt thereof.

2. The compound of claim 1, wherein the compound is (Z)-1-(2-(4-(4-(((2-(4-(1,2-diphenylbut-1-en-1-yl)phenoxy)ethyl)(methyl)amino)methyl)phenyl)-1H-1,2,3-triazol-1-yl)ethyl)-3-hydroxy-2-methylpyridin-4 (1H)-one or a hydrate thereof, or a solvate thereof, or a pharmaceutically acceptable salt thereof.

3. The compound of claim 1, wherein the compound is (Z)-1-(3-(4-(4-(((2-(4-(1,2-diphenylbut-1-en-1-yl)phenoxy)ethyl)(methyl)amino)methyl)phenyl)-1H-1,2,3-triazol-1-yl)propyl)-3-hydroxy-2-methylpyridin-4 (1H)-one, or a hydrate thereof, or a solvate thereof, or a pharmaceutically acceptable salt thereof.

4. The compound of claim 1, wherein the compound is (Z)-1-(4-(4-(4-(((2-(4-(1,2-diphenylbut-1-en-1-yl)phenoxy)ethyl)(methyl)amino)methyl)phenyl)-1H-1,2,3-triazol-1-yl)butyl)-3-hydroxy-2-methylpyridin-4 (1H)-one, or a hydrate thereof, or a solvate thereof, or a pharmaceutically acceptable salt thereof.

5. The compound of claim 1, wherein the compound is (Z)-1-(5-(4-(4-(((2-(4-(1,2-diphenylbut-1-en-1-yl)phenoxy)ethyl)(methyl)amino)methyl)phenyl)-1H-1,2,3-triazol-1-yl)pentyl)-3-hydroxy-2-methylpyridin-4 (1H)-one, or a hydrate thereof, or a solvate thereof, or a pharmaceutically acceptable salt.

6. The compound of claim 1, wherein the compound is (Z)-1-(6-(4-(4-(((2-(4-(1,2-diphenylbut-1-en-1-yl)phenoxy)ethyl)(methyl)amino)methyl)phenyl)-1H-1,2,3-triazol-1-yl)hexyl)-3-hydroxy-2-methylpyridin-4 (1H)-one, or a hydrate thereof, or a solvate thereof, or a pharmaceutically acceptable salt thereof.

7. The compound of claim 1, wherein the compound is (Z)-1-(7-(4-(4-(((2-(4-(1,2-diphenylbut-1-en-1-yl)phenoxy)ethyl)(methyl)amino)methyl)phenyl)-1H-1,2,3-triazol-1-yl)heptyl)-3-hydroxy-2-methylpyridin-4 (1H)-one, or a hydrate thereof, or a solvate thereof, or a pharmaceutically acceptable salt thereof.

8. The compound of claim 1, wherein the compound is (Z)-1-(5-(4-(4-(((2-(4-(1,2-diphenylbut-1-en-1-yl)phenoxy)ethyl)(methyl)amino)methyl)phenyl)-1H-1,2,3-triazol-1-yl)pentyl)-2-ethyl-3-hydroxypyridin-4 (1H)-one, or a hydrate thereof, or a solvate thereof, or a pharmaceutically acceptable salt.

9. A pharmaceutical composition comprising a compound according to claim 1.

10. The pharmaceutical composition of claim 9, further comprising a pharmaceutically acceptable carrier.

11. The pharmaceutical composition of claim 9, further comprising a pharmaceutically acceptable excipient.

12. A method of treatment comprising:

administering a compound in an amount effective to inhibit histone lysine demethylase activity in a subject in need thereof;

wherein the compound comprises:

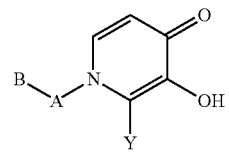

Formula I wherein

A is —$(CH_2)_n$—, wherein n is from 2-8;

B is AR-AR';

AR' is a linking group connecting AR and A, and AR' is selected from the group consisting of

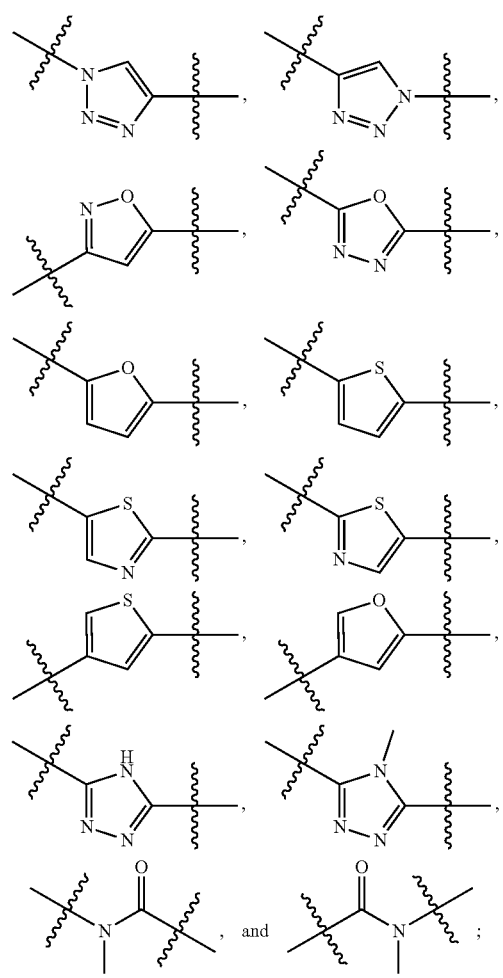

AR is aryl, 6-membered aromatic, heterocyclic, fused aromatic, fused heterocyclic, biaromatic, or a biheterocyclic ring system, wherein the aryl, 6-membered aromatic, heterocyclic, fused aromatic, fused heterocyclic, biaromatic or biheterocyclic ring system is optionally substituted by halogen-, alkyl-, alkoxy-, haloalkyl-, alkylamino-, aryl-, heteroaryl-, alkenyl-, alkynyl- or X;

X is:

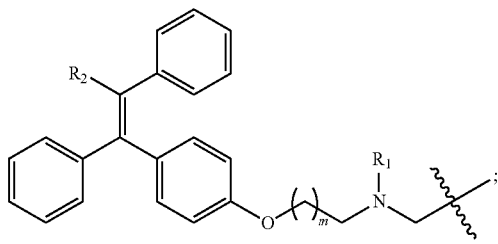

R₁ is H or $C_1$-$C_6$ alkyl;
R₂ is halogen, alkyl or aryl;
m is from 1-5; and
Y is an alkyl or aryl, or a hydrate thereof, or a solvate thereof, or a pharmaceutically acceptable salt thereof.

13. The method of claim 12, wherein the subject has cancer.

14. The method of claim 13, wherein the subject has breast cancer or prostate cancer.

15. A method of reducing tumor burden in a subject in need thereof comprising administering an effective amount of a compound according to claim 1 to inhibit lysine demethylase in the subject.

16. A method of reducing or inhibiting cancer cell proliferation in a subject in need thereof, comprising administering an effective amount of a compound according to claim 1 to reduce or inhibit cancer cell proliferation in the subject.

17. A method of reducing or inhibiting cancer cell proliferation in a subject in need thereof, comprising administering an effective amount of a pharmaceutical composition according to claim 9 to reduce or inhibit cancer cell proliferation in the subject.

18. The method of claim 12, further comprising administering a chemotherapeutic agent to the subject.

19. The method of claim 12, wherein the compound is selected from the group consisting of:
(Z)-1-(2-(4-(4-(((2-(4-(1,2-diphenylbut-1-en-1-yl)phenoxy)ethyl)(methyl)amino)methyl)phenyl)-1H-1,2,3-triazol-1-yl)ethyl)-3-hydroxy-2-methylpyridin-4 (1H)-one;
(Z)-1-(3-(4-(4-(((2-(4-(1,2-diphenylbut-1-en-1-yl)phenoxy)ethyl)(methyl)amino)methyl)phenyl)-1H-1,2,3-triazol-1-yl)propyl)-3-hydroxy-2-methylpyridin-4 (1H)-one;
(Z)-1-(4-(4-(4-(((2-(4-(1,2-diphenylbut-1-en-1-yl)phenoxy)ethyl)(methyl)amino)methyl)phenyl)-1H-1,2,3-triazol-1-yl)butyl)-3-hydroxy-2-methylpyridin-4 (1H)-one;
(Z)-1-(5-(4-(4-(((2-(4-(1,2-diphenylbut-1-en-1-yl)phenoxy)ethyl)(methyl)amino)methyl)phenyl)-1H-1,2,3-triazol-1-yl)pentyl)-3-hydroxy-2-methylpyridin-4 (1H)-one;
(Z)-1-(6-(4-(4-(((2-(4-(1,2-diphenylbut-1-en-1-yl)phenoxy)ethyl)(methyl)amino)methyl)phenyl)-1H-1,2,3-triazol-1-yl)hexyl)-3-hydroxy-2-methylpyridin-4 (1H)-one;
(Z)-1-(7-(4-(4-(((2-(4-(1,2-diphenylbut-1-en-1-yl)phenoxy)ethyl)(methyl)amino)methyl)phenyl)-1H-1,2,3-triazol-1-yl) heptyl)-3-hydroxy-2-methylpyridin-4 (1H)-one; and
(Z)-1-(5-(4-(4-(((2-(4-(1,2-diphenylbut-1-en-1-yl)phenoxy)ethyl)(methyl)amino)methyl)phenyl)-1H-1,2,3-triazol-1-yl)pentyl)-2-ethyl-3-hydroxypyridin-4 (1H)-one, or a hydrate thereof, or a solvate thereof, or a pharmaceutically acceptable salt thereof.

20. The compound of claim 1, wherein
R₁ is H, methyl, or ethyl;
R₂ is Cl, methyl, ethyl, phenyl or pyridyl; and
Y is methyl, ethyl, phenyl or pyridyl.

21. The compound of claim 1, which is a hydrate, a solvate or a resolved single isomer of the compound of Formula I.

* * * * *